US008715635B2

(12) United States Patent
Keinan

(10) Patent No.: US 8,715,635 B2
(45) Date of Patent: May 6, 2014

(54) FRICTIONLESS MOLECULAR ROTARY MOTORS

(75) Inventor: Ehud Keinan, Timrat (IL)

(73) Assignee: Technion Research & Development Foundation Limited, Haifa (IL)

( * ) Notice: Subject to any disclaimer, the term of this patent is extended or adjusted under 35 U.S.C. 154(b) by 816 days.

(21) Appl. No.: 12/526,046

(22) PCT Filed: Feb. 6, 2008

(86) PCT No.: PCT/IL2008/000167
§ 371 (c)(1),
(2), (4) Date: Aug. 6, 2009

(87) PCT Pub. No.: WO2008/096360
PCT Pub. Date: Aug. 14, 2008

(65) Prior Publication Data
US 2010/0016610 A1 Jan. 21, 2010

Related U.S. Application Data

(60) Provisional application No. 60/899,655, filed on Feb. 6, 2007.

(51) Int. Cl.
*A61K 31/74* (2006.01)
(52) U.S. Cl.
USPC .................. 424/78.17; 424/78.18; 424/78.19; 424/78.22; 424/78.23; 424/78.29; 424/78.3; 424/78.31; 424/78.32
(58) Field of Classification Search
None
See application file for complete search history.

(56) References Cited

U.S. PATENT DOCUMENTS

| 7,163,658 | B2 | 1/2007 | Bension |
| 2005/0032081 | A1 | 2/2005 | Ju et al. |
| 2006/0154254 | A1 | 7/2006 | Kim et al. |
| 2006/0292570 | A1* | 12/2006 | Keinan ............................. 435/6 |

FOREIGN PATENT DOCUMENTS

| WO | WO 2005/0031316 | 1/2005 |
| WO | WO 2005/023816 | 3/2005 |

OTHER PUBLICATIONS http://en.wikipedia.org/wiki/Conjugated_system printed from online source on Jul. 25, 2013.*

Balzani et al. "Artificial Molecular Machines", Angewandte Chemie, International Edition, XP002488299, 39: 3348-3391, 2000.
Buschmann et al. "The Complex Formation of α,ω-Dicarboxylic Acids and α,ω-Diols With Cucurbituril and α-Cyclodextrin. The First Step to the Formation of Rotaxanes and Polyrotaxanes of the Polyester Type", Acta Chimica Slovenica, Slovensko Kemijsko Drustvo, XP002488298, 46(3): 405-411, 1999. Table 1.
Lagona et al. "The Cucurbit[n] Uril Family", Angewandte Chemie, International Edition, XP001232746, 44(31): 4844-4870, Aug. 5, 2005. Figs.5, 6, Table 5, Compounds 16, 42, 43.
Lu et al. "Interaction Between Cucurbit[6]Uril and Bispyridinecarboxamide", Journal of Inclusion Phenomena and Macrocyclic Chemistry, XP019528610, 59(1-2): 81-90, Mar. 21, 2007. p. 83, r-h Col., Last §, Fig.1, p. 88, 1-h Col., § 1-2.
Meschke "Mono-, Oligo- und Polyrotaxane mit Cucurbituril und gemischte Polyrotaxane mit Cucurbituril und Alpha-Cyclodextrin mittels Selbstorganisation", Thesis, Doctoral Dissertation Accepted by University of Duisburg, Germany, Department of Chemistry, XP002488300, p. 47-69, Sep. 16, 1998. Chap.5, Figs.5.1, 5.7. Abstract in English!.
Meschke et al. "Synthesis of Mono-, Oligo- and Polyamide-Cucurbituril Rotaxanes", Macromolecular: Rapid Communications, XP000738939, 19: 59-63, Jan. 1, 1998. Scheme 1.
Miljanić et al. "Rotaxanes and Catenanes by Click Chemistry", QSAR & Combinatorial Science, 11-12: 1165-1174, 2007.
Kim et al. "New Cucurbituril Homologues: Syntheses, Isolation, Characterization, and X-Ray Crystal Structures of Cucurbit[n] Uril (n = 5, 7, and 8)", Journal of the American Chemical Society, XP002174906, 122(3): 540-541, Jan. 1, 2000. Fig.2.
Lagona et al. "The Cucurbit[n]Uril Family", Angewandte Chemie, International Edition, XP001232746, 44(31): 4844-4870, Aug. 5, 2005. Figs.5, 6, Table 5, Compounds 16, 42, 43.
Meschke "Mono-, Oligo- und Polyrotaxane mit Cucurbituril und gemischte Polyrotaxane mit Cucurbituril und Alpha-Cyclodextrin mittels Selbstorganisation", Thesis, Doctoral Dissertation Accepted by University of Duisburg, Germany, Department of Chemistry, XP002488300, p. 47-69, Sep. 16, 1998. Chap.5, Figs.5.1, 5.7. Abstract in English.
Miljanić et al. "Rotaxanes and Catenanes by Click Chemistry", QSAR & Combinatorial Science, 11-12: 1165-1174, 2007.
Mock "Cucurbituril", Comprehensive Supra-Molecular Chemistry, XP001205146, p. 477-493, Jan. 1, 1996. p. 481, Fig.3, Table 1.
Sindelar et al. "Switching a Molecular Shuttle On and Off: Simple, PH-Controlled Pseudorotaxanes Based on Cucurbit[7]Uril", Chemical Communications, p. 2185- 2187, 2006.
Tian et al. "Recent Progress on Switchable Rotaxanes", Chemical Society Reviews, 35: 361-374, 2006.

* cited by examiner

*Primary Examiner* — James Rogers

(57) ABSTRACT

A rotaxane consisting of a cucurbituril and an uncharged guest molecule, having low or null affinity therebetween is provided as well as processes for providing the same. Various uses as energy converters ("frictionless" molecular motors), biochips and biosensors using the same are also provided.

7 Claims, 7 Drawing Sheets

FRICTIONLESS MOLECULAR ROTARY MOTORS

RELATED APPLICATIONS

This application is a National Phase of PCT Patent Application No. PCT/IL2008/000167 having International filing date of Feb. 6, 2008, which claims the benefit of U.S. Provisional Patent Application No. 60/899,655 filed on Feb. 6, 2007. The contents of the above applications are all incorporated herein by reference.

FIELD AND BACKGROUND OF THE INVENTION

The present invention, in some embodiments thereof, relates to the design, construction and uses of molecular nano-motors and, more particularly, but not exclusively, to molecular rotary motors based on a rotaxane architecture which includes a cucurbit[n]uril and an uncharged guest molecule having low or null affinity therebetween.

Nanotechnology is a broad term used to describe the field of applied science and technology dealing with the control of matter on the atomic and molecular scale, typically from 1 nm to 100 nm, and the fabrication of devices in this order of magnitude. Nanotechnology stems from the fields of supramolecular chemistry, biology, applied physics, materials science, mechanical and electrical engineering, colloidal science, device physics, and others. The shift from standard mechanics to nano-scale mechanics is non-trivial since the physical, chemical, and biological properties of materials may differ fundamentally at the nanoscale level from the bulk properties of the materials, leading to unexpected results because of variations on the quantum mechanical properties of atomic interactions.

Molecular motors, as used in the context of the present invention, are nano-scaled structures that are likely to prove especially valuable in the emerging field of nanotechnology. The overall significance of nano-scaled motors to nanotechnology is comparable to the impact of the engine in modern society. The ability to harness and utilize, to both construct and deconstruct, these motors has the potential to expand and revolutionize the field of nanotechnology.

Biological proteinous molecular motors precedents [1], such as bacterial flagellar motor [2], F1-ATPase (ATP synthase)[3-5], kinesin, myosin [6] and helicase [7], which interconvert chemical energy and coordinated mechanical motion, transport and manipulate cellular components.

Synthetic molecular motors, which are not based on proteins, have been theorized and hypothesized in the past decades [8-12]. Most of the reported efforts to synthesize molecular rotary motors, including bevel gears, propellers, a three-propeller system, and molecular turnstiles [13-27] have exploited intramolecular interactions with one molecular fragment rotating with respect to the rest of the molecule around one or two single bonds [28-33].

One of the most challenging design elements of molecular rotary motors is their requirement of a unidirectional motion. Attempts to meet this challenge have resulted in various stepwise (non-continuous), unidirectional moving devices [34, 35], including light-driven [36-38], chemically driven [8, 39, 40], and electrically driven machines [22, 24, 41, 26, 27].

A synthetic chemically driven rotary molecular motor was reported by Kelly et al. in 1999 [39], which provided a system based on a three-bladed triptycene rotor and a [4]helicene molecule, which was capable of performing a unidirectional 120° rotation. The molecular motor of Kelly et al. is an elegant example of how chemical energy can be used to induce controlled, unidirectional rotational motion, a process which resembles the consumption of ATP in organisms in order to fuel numerous processes. However, it does suffer from lack of repeatability of the sequence of events that leads to 120° rotation, and attempts to overcome this limitation have not been successful hitherto.

Fering a et al. reported in 1999 [36] the creation of a unidirectional molecular rotor. Their 360° molecular motor system consists of a bis-helicene connected by an alkene double bond displaying axial chirality and having two stereocenters, wherein one cycle of unidirectional rotation takes four reaction steps. This system was characterized by low speed due to the long reaction time needed to complete one rotation in these systems, which does not compare to rotation speeds displayed by motor proteins in biological systems. Fering a et al. continued to improve the speed of these light-driven unidirectional molecular motors and provided faster system with a fluorene lower half, exhibiting a half-life of the thermal helix inversion of 0.005 seconds [42, 43]. The Fering a principle has been incorporated into a prototype nanocar [44], based on an helicene-derived engine with an oligophenylene ethynylene chassis and four carborane wheels and is expected to be able to move on a solid surface with scanning tunneling microscopy monitoring, although this has not been observed to date.

An alternative approach to such machines exploits the rotaxane's mechanically-interlocked molecular architecture, which consists of a macrocyclic molecule threaded by a linear "dumbbell shaped molecule" guest molecule that is terminated by two bulky stopper moieties [45-48]. Rotaxanes can exhibit three types of motion: rotation of a wheel around an axle (or a rotator inside a stator, which depends on the frame of reference), shuttling of the wheel along the axle in a piston-like motion, and a pivoting motion, where the angle between the axle and the main axis of the host changes. The shuttling motion has been studied in great detail both experimentally and theoretically [49]. A similar motion of circumrotation in catenanes was also investigated [35]. External stimuli, such as light, thermal energy, or electrochemical energy have been used to control the motion, including the threading/unthreading motion of pseudo rotaxanes [50-54]. An external electric field has been shown to induce the rotation of a rotaxane wheel around its axle, demonstrating that rotaxanes could interconvert different types of energy and therefore may potentially be used as energy converters [41].

SUMMARY OF THE INVENTION

The present invention provides rotaxanes based on a cucurbit[n]uril host and a guest molecule, which exhibit low affinity to one another, and possibly even repel one another. This unique configuration is afforded by employing a novel synthetic approach for preparing cucurbit[n]uril-based rotaxanes having an uncharged guest molecule threaded inside the cucurbit[n]uril. The present rotaxanes, referred to herein as "frictionless" molecular rotors, can be attached to a solid support and be used in a variety of applications, such as energy converters (motors), biochips and biosensor.

Hence, according to an aspect of some embodiments of the present invention there is provided a rotaxane which includes a host molecule and a guest molecule, the host molecule being a cucurbit[n]uril (CB[n]), and the guest molecule having the general Formula I:

U—$B_1$-$L_1$-$[A]_m$-$L_2$-$B_2$—Y    Formula I wherein:

n is an integer that ranges from 5 to 20;

$B_1$ and $B_2$ are each independently an uncharged stopper moiety;

$L_1$ and $L_2$ are each independently an uncharged linking moiety or absent;

$[A]_m$ is an uncharged threading moiety;

m is an integer that ranges from 1 to 50;

U and Y are each independently selected from the group consisting of an anchoring group, an effector moiety, a detectible moiety, a biomolecule, or absent.

According to some embodiments of the invention, n ranges from 5 to 8.

According to other embodiments of the invention, A is selected from the group consisting of a 1,2-ethyn-di-yl, a substituted or unsubstituted aryl, a substituted or unsubstituted heteroaryl, substituted or unsubstituted cyclobuta-1,3-diene-1,3-di-yl, substituted or unsubstituted pentalene-2,5-di-yl, substituted or unsubstituted benzene-1,4-di-yl, substituted or unsubstituted pyrene-2,7-di-yl, C-substituted or unsubstituted pyridine-2,5-di-yl, C-substituted or unsubstituted pyrimidine-2,5-di-yl, C-substituted or unsubstituted pyrazine-3,6-di-yl and 1,2,4,5-tetrazine-3,6-diyl.

According to other embodiments of the invention, the stopper moiety is selected from the group consisting of a branched alkyl moiety, a branched cycloalkyl moiety, a branched heteroalicyclic moiety, a branched polyaryl moiety, a branched polyheteroaryl moiety, an adamantly moiety, a branched organophosphorous, a branched organoboron, a branched organosilicon and a branched carboranes.

According to other embodiments of the invention, the linking moiety is selected from the group consisting of alkyl, alkenyl, alkynyl, cycloalkyl, heteroalicyclic, aryl, heteroaryl, ether, thioether, amide, ester, carbamate, thioamide, thiocarbamate, imine, aza, organophosphorous, organoboron and organosilicon.

According to other embodiments of the invention, the effector moiety is selected from the group consisting of a charged moiety, a metal ion complex moiety, a magnetic moiety and a light absorbing moiety.

According to other embodiments of the invention, the cucurbit[n]uril further includes one or more functionality attached thereto selected from the group consisting of an anchoring group, an effector moiety, a detectible moiety and a biomolecule.

According to another aspect of some embodiments of the present invention there is provided a composition-of-matter which includes the rotaxane presented herein attached to a solid support.

According to yet another aspect of some embodiments of the present invention there is provided a composition-of-matter which includes a plurality of the rotaxane presented herein attached to a solid support.

According to an aspect of some embodiments of the present invention there is provided a composition-of-matter which includes a plurality of the rotaxane presented herein attached to one another.

According to other embodiments of the invention, the rotaxane is attached via the anchoring group on the guest molecule.

According to other embodiments of the invention, the rotaxane is attached via the anchoring group on the host molecule.

According to other embodiments of the invention, the rotaxane and/or the compositions presented herein are capable of converting energy from one form to another.

According to another aspect of some embodiments of the present invention there is provided a process of preparing the rotaxane presented herein, which is effected by:

providing a complex which includes a host molecule and a guest molecule, the host molecule being a cucurbit[n]uril (CB[n]), and the guest molecule having a general formula selected from the group consisting of Formula II or Formula III:

U—$B_1$-$L'_1$-$[A]_m$-$L'_2$-$B_2$—Y            Formula II

U—$B_1$-$L_1$-$[A]_m$-$L'_2$-$B_2$—Y            Formula III wherein:

n is an integer that ranges from 5 to 20;

$[A]_m$ is an uncharged threading moiety;

m is an integer that ranges from 1 to 50;

$L'_1$ and $L'_2$ are each independently an affinity moiety or one of $L'_1$ and $L'_2$ is absent and at least one of $L'_1$ and $L'_2$ independently includes a positively charged group;

$L_1$ is an uncharged linking moiety or absent;

$B_1$ and $B_2$ are each independently an uncharged stopper moiety;

U and Y are each independently selected from the group consisting of an anchoring group, an effector moiety, a detectible moiety, a biomolecule, or absent; and substantially neutralizing the positively charged group to thereby obtain the present rotaxane.

According to other embodiments of the invention, the process further includes, prior to the neutralization:

contacting the cucurbit[n]uril with a compound having a general formula selected from the group consisting of Formula IV, Formula V or Formula VI:

$R_1$-$L'1$-$[A]_m$-$L'_2$-$R_2$            Formula IV

U—$B_1$-$L'_1$-$[A]_m$-$L'_2$-$R_2$            Formula V

U—$B_1$-$L_1$-$[A]_m$-$L'2$-$R2$            Formula VI wherein:

n is an integer that ranges from 5 to 20;

$[A]_m$ is an uncharged threading moiety;

m is an integer that ranges from 1 to 50;

$L'_1$ and $L'_2$ are each independently an affinity moiety or one of $L'_1$ and $L'_2$ is absent and at least one of $L'_1$ and $L'_2$ independently includes a positively charged group;

$R_1$ and $R_2$ are each independently a reactive group;

$L_1$ is an uncharged linking moiety or absent;

$B_1$ is an uncharged stopper moiety;

U is selected from the group consisting of an anchoring group, an effector moiety, a detectible moiety, a biomolecule, or absent;

thereby forming a complex between the cucurbit[n]uril and the compound having a general formula selected from the group consisting of Formula IV, Formula V or Formula VI via at least one of the affinity moiety; and contacting the complex with a compound having the general Formula VII and/or a compound having the general Formula VIII:

U—$B_1$—$R_4$            Formula VII

$R_3$—$B_2$—Y            Formula VIII wherein:

$R_3$ and $R_4$ are each independently a reactive group;

$B_1$ and $B_2$ are each independently an uncharged stopper moiety; and

U and Y are each independently selected from the group consisting of an anchoring group, an effector moiety, a detectible moiety, a biomolecule, or absent;

thereby forming a guest molecule within the cucurbit[n]uril, the guest molecule is having a general formula selected from the group consisting of Formula II or Formula III.

According to yet another aspect of the present invention, there is provided a process of preparing the rotaxane presented herein, which is effected by:

contacting the cucurbit[n]uril with a compound having the general Formula VI:

$$U-B_1-L_1-[A]_m-L'_2-R_2 \quad \text{Formula IX}$$

wherein:

n is an integer that ranges from 5 to 20;

$[A]_m$ is an uncharged threading moiety;

m is an integer that ranges from 1 to 50;

$L'_2$ is an affinity moiety which includes a positively charged group;

$R_2$ is a reactive group;

$L_1$ is an uncharged linking moiety or absent;

$B_1$ is an uncharged stopper moiety;

U is selected from the group consisting of an anchoring group, an effector moiety, a detectible moiety, a biomolecule, or absent;

thereby forming a complex between the cucurbit[n]uril and the compound having the general Formula IV via the affinity moiety; and contacting the complex with a compound having the general Formula X:

$$R_3-B_2-Y \quad \text{Formula X}$$

wherein:

$R_3$ is a reactive group;

$B_2$ is an uncharged stopper moiety; and

Y is selected from the group consisting of an anchoring group, an effector moiety, a detectible moiety, a biomolecule, or absent;

thereby substantially neutralizing the positively charged group and forming the present rotaxane.

According to some embodiments of the invention, R3 is an affinity moiety.

According to other embodiments of the invention, the cucurbit[n]uril is attached to a solid support prior to the preparation process of the present rotaxane.

According to other embodiments of the invention, any one of U or Y is attached to a solid support prior to the preparation process of the present rotaxane.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF THE PREFERRED EMBODIMENTS

Figure 1A:
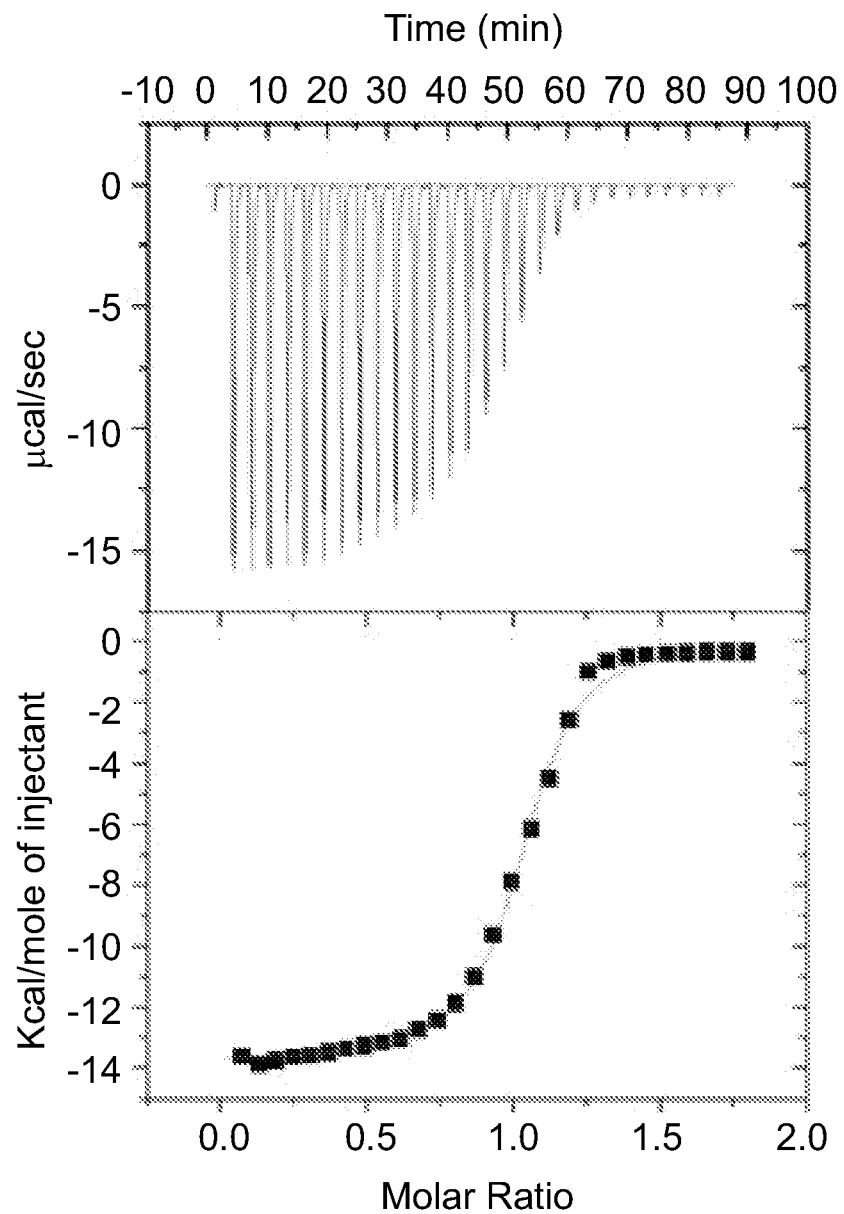
FIG. 1 presents the isothermal titration calorimetry (ITC) curves obtained for Compound 1 (0.4 mM in water) titrated with several exemplary positively charged guest molecules at 30° C., wherein FIG. 1A was obtained by titrating a solution of Compound 3' (3.33 mM), FIG. 1B was obtained by titrating a solution of Compound 4' (6 mM), FIG. 1C was obtained by titrating a solution of Compound 6' (3.3 mM) and FIG. 1D was obtained by titrating a solution of Compound 7' (5.0 mM).

The present invention, in some embodiments thereof, relates to the design, construction and uses of molecular nano-motors and, more particularly, but not exclusively, to molecular rotary motors based on a rotaxane architecture which includes a cucurbit[n]uril and an uncharged guest molecule having low or null affinity therebetween.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Although machine-like synthetic molecular devices available today are far from being optimal, the importance of constructing synthetic molecular machines is evidenced by the fact that molecular machines exist in all living system. Biological molecular machines are categorized in two types according their motion: rotary and linear motors. The rotary motors are perhaps the most fascinating and studied natural machines. Inspired by the physical shape of the biological rotary motors and of the macroscopic rotary motors, this invention is directed at the rational design and synthesis of low-friction rotaxane-type devices. The architecture of these machines can be described as a rod, or a threading moiety (guest) inside a wheel or a rotatable bead (host) and a thread that is capped with two end-blockers or stopper moieties. In order to produce useful work, many design elements should be considered while contemplating a molecular rotary motor. Some of the most challenging design elements are controllable unidirectional motion, repetitive motion and high speed of rotation.

As presented hereinabove, in the past decade several unidirectional rotors, such as rotaxane-type molecular motors, have been reported, however these rotors involve high-energy barriers for rotation, resulting in a slow or even stepwise motion. The relatively ignored but fundamentally challenging design element, namely the need for high-speed rotation, requires a low energy barrier for rotation, which can be related metaphorically to the macroscopic term "friction" in order to describe rotation that involves very low energy barriers. Hence the term used herein to describe this design element is "frictionless" molecular motor.

Most of the reported rotating molecular vanes and blades discussed hereinabove required much energy for their motion because they were comprised a molecular fragment that was connected to the rest of the molecule by two single bonds, around which the fragment rotated. The present inventor has envisioned that synthetic building blocks may be used for constructing a frictionless rotary motion. While conceiving the present invention, it was suggested by the present inventor that in order to achieve minimal "friction" in a rotaxane-type molecular motor, the rotator-stator couple should repel one another. It was further hypothesized that a stator-rotator couple, based on rotaxane-type architecture, with a macrocyclic cucurbituril host serving as a molecular stator, whereas a stator is a borrowed term which refers to the stationary part of a rotary electrical motor.

Since the late 1960s, a branch of chemistry, called supramolecular chemistry, emerged and expanded rapidly. Host-guest complexation study has attracted several attentions to understand the substrate-receptor complexation processes which occur with biological molecules on a smaller scale. A complementary in molecular shape or surface of both binding partners provides the foundation of all recognition process. The non-specific association based on Van der Waals or hydrophobic forces can become more specific and stronger by Hydrogen bonding or electrostatic interactions. Organic host molecules, which can be considered as molecular containers with interior cavities, large enough to accommodate guest molecules, are among the most fascinating and challenging topics of supramolecular chemistry. Cryptands, Cyclophanes, Cyclodextrines, Calixarenes, Cavitands, Carcerands are known organic host molecules and Cucurbiturils (CBs) or Cucurbit[n]uril (CB[n]) is an interesting addition to this family.

Cucurbiturils (also referred to herein interchangeably in the singular form as CB, CB[n] or cucurbit[n]uril) are macrocyclic cavitand compounds which are known since 1905 [55-60], and were characterized by Mock and co-workers in 1981 [61]. CBs are formed typically by reacting a number of glycoluril units and formaldehyde units under acidic conditions. For example, Cucurbit[6]uril, also known and referred to herein as CB[6] (See, Compound 1 in Scheme 1 below), is typically prepared by reacting six glycoluril molecules, (See, Compound 2 in Scheme 1 below) and twelve formaldehyde units, in the presence of a concentrated acid, as is illustrated in Scheme 1 Scheme 1.

Scheme 1

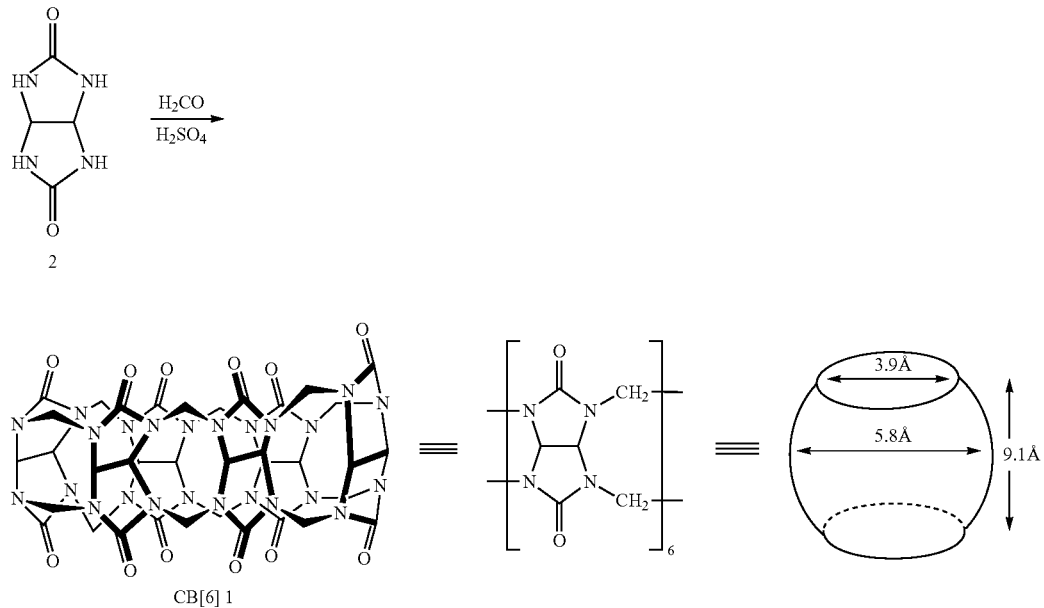

Cucurbiturils, either substituted or unsubstituted, are typically characterized by a hydrophobic cavity that is accessible through two identical, polar, carbonyl-fringed portals. These structural and chemical features renders the CB[n] cavitands ideal host molecules for neutral molecules [62, 63] and essentially cations of any metal such as alkali-metals, alkaline-earths, transition-metals, and lanthanides [64-68] and, in particular, protons and cations that can form hydrogen bonding, such as ammonium cations [69].

The solubility of the CB[n] family is relatively low, reaching less than 1 mM at pH=7 in water. Like urea itself, however, the carbonyl groups lining the portals of CB[n] are weak bases, and the $pK_a$ value of the conjugate acid of CB[6] is 3.02. Although the $pK_a$ values of CB[5], CB[7], and CB[8] have not been measured, they are likely to be similar to that of CB[6]. Accordingly, the solubility of CB[5]-CB[8] increases dramatically in concentrated aqueous acid. For example, 61 mM for CB[6] in $HCO_2H/H_2O$ (1:1), about 60 mM for CB[5], about 700 mM for CB[7], and about 1.5 mM for CB[8] in 3M HCl.

CB[6] (Compound 1) forms exceptionally stable host-guest complexes with protonated amines and, in particular, with doubly protonated diaminoalkanes, such as 1,4-diaminobutane, 1,5-diaminopentane and 1,6-diaminohexane with affinity between these two conjugates of $K_a=10^6-10^5$ M. One such suitable guest molecule for Compound 1 is the diammonium cation 1,6-diaminohexane, (Compound 3' [69]). Three modes of attractive interaction contribute to the strong binding interaction between Compound 1 and Compound 3' in water, namely charge-dipole interaction between the ammonium group and the CB portal, hydrogen bonding between the same, and hydrophobic interaction between the hydrocarbon chain and the interior of Compound 1.

While further conceiving the present invention, it was suggested that an uncharged rigid and linear guest molecule threaded into a CB (and thus serving as a molecular rotator), can afford an efficient frictionless stator-rotator rotary motion. It was hypothesized that, in contrast to the observations with Compound 3', an uncharged guest molecule, such as a polyalkyne (polyyne), would exhibit very low binding interactions, or even repulsive interactions with the interior and oculi of Compound 1. Without being bound by any particular theory, this repulsive interaction is attributed to the high electron density of both polyalkyne and the CB interior [70]. Furthermore, the 48 non-bonding electrons of the carbonyl oxygens at the CB portals and the filled π-orbitals of the 12 urea groups are expected to repel the π-electrons of the polyyne-like guest molecule. Accordingly, it was predicted that if a polyyne-like rod could be inserted into the cavity of Compound 1, the repulsive interaction would keep the polyyne-like rod "floating" at the center of the cavity in exact alignment with the 6-fold symmetry axis of Compound 1.

While further conceiving the general design of low-friction rotary motors based on cucurbit[6]uril, and considering the requirement of low-friction and the general architecture of a rotaxane that has two stopper moieties [71, 72], a second mode of repulsive interaction between the two molecular partners was contemplated, one that minimizes the friction between the CB portals and the bulky stoppers at the ends of the uncharged guest. It was hypothesized that this requirement could be achieved by the design and selection of uncharged stopper groups, or a bulky stopper moieties selected so as to exhibit a strong dipole moment that opposes the dipole moment of the CB portal. Such repulsive interactions would maintain the two stopper moieties floating at a maximal distance from the CB portals, reminiscent of a magnet floating over the pole of an opposite magnetic field.

While reducing the present invention to practice, molecular mechanics calculations using model systems have shown that the notion of repulsive interaction between cucurbituril component and the polyyne-like component capped with two bulky groups is well founded, which was further confirmed experimentally by microcalorimetry and X-ray crystallography using several synthetic host-guest complexes Cucurbit[n]uril-based rotaxanes and pseudorotaxanes are well know in the art [71, 58, 73-75], and some have been suggested as tools in a variety of applications such as in U.S. Pat. No. 7,163,658, which teaches rapid sequencing of polymers and nucleic acids using the same, and in U.S. Patent Application No. 20060154254 and WO 05003136, which teach biochips using cucurbit[n]urils-based rotaxanes and rotaxane-bonded solid substrate (all of which are incorporated herein by reference as if fully set-forth herein). However, all the cucurbit[n]uril-based rotaxanes and pseudorotaxanes taught in the art are based on charged guest molecules, and more specifically positively charged guest molecules, which exhibit high affinity to the cucurbituril host, a factor which negates the concept presented herein, of a "low friction" rotaxane, having little or no attraction, and even repulsive interactions between the host and the guest.

While further reducing the present invention to practice, it was found that in order to provide a rotaxane based on a cucurbit[n]uril and an uncharged guest molecule, a new synthetic approach for preparing cucurbit[n]uril-based rotaxanes must be developed since the fundamental factor which forms such rotaxanes, namely the affinity between the cucurbit[n]uril and the commonly used (doubly) positively charged guest molecules, is eliminated and even negated when attempting to use uncharged guest molecules.

Hence, according to one aspect of the present invention, there is provided a process for preparing a rotaxane which includes a host molecule and guest molecule having low, null or negative affinity to the host molecule, namely a rotaxane wherein the host and the guest components do not exhibit attraction interaction (affinity) or a low affinity therebetween, or even exhibit repulsive interaction therebetween.

According to this aspect of the present invention, the host molecule is a cucurbit[n]uril (CB[n], cucurbit[n]uril), wherein n is an integer that ranges from 5 to 20, namely CB[5], CB[6], CB[7], CB[8] and the likes up to CB[20], and the uncharged guest molecule is a compound having the general Formula I:

$$U-B_1-L_1-[A]_m-L_2-B_2-Y \qquad \text{Formula I}$$

wherein:

$B_1$ and $B_2$ are each independently an uncharged stopper moiety;

$L_1$ and $L_2$ are each independently an uncharged linking moiety or absent;

[A], is an uncharged threading moiety;

m, representing the length of the threading moiety, is an integer that ranges from 1 to 50; and U and Y are each independently selected from the group consisting of an anchoring group, an effector moiety, a detectible moiety, a biomolecule, or absent.

The term "rotaxane", as used herein and presented hereinabove, refers to a mechanically-interlocked molecular complex consisting of a macrocyclic host molecule that is threaded through by a guest molecule, which is capped at each end thereof by bulky moieties. The guest molecule of a rotaxane complex is oftentimes described as having a "dumbbell" shape, which comprises two stopper moieties connected by a threading moiety.

According to some embodiments of the present invention, the rotaxane is a cucurbit[n]uril-based rotaxane, wherein n is 5, 6, 7 or 8.

The phrase "repulsive interaction", as used herein, refers to intermolecular interaction based on short-range repulsive intermolecular forces, such as van der Waal's forces, Born or Pauli interactions, which include momentary attraction/repulsion between molecules and individual atoms. Short-range repulsive interactions differ from covalent and long-range interactions, such as ionic bonding, in that they are not stable, but are caused by momentary polarization of outer electronic shells of the interacting counter parts. In the context of the present embodiments, repulsive interactions are based on the lack of long-range attractive forces such as electrostatic interactions present between opposite electrostatic charges or partial charges (such as ionic interactions, dipole-dipole interactions and hydrogen bonding), and magnetic interactions (such as between opposite magnetic dipoles).

The term "uncharged" refers to a molecular species or a sub-molecular moiety having a neutral net charge at a pH that ranges from 6-8, or a net positive or negative charge of less than 0.5 electron charge unit at a pH that ranges from 6-8.

The term "neutral" refers to any molecular species or sub-molecular moieties which exist in an uncharged form at a pH that range from 6-8. As used herein, this term excludes cases of neutral zwitterionic molecular species or sub-molecular moieties which contain both a positive and a negative charge that counter each other so as to attribute a neutral overall charge to the molecule or moiety.

As used herein, the phrase "moiety" describes a part of a chemical entity or compound, which typically has certain functionality or distinguishing features.

The term "stopper moiety", as used herein, refers to a chemical moiety which is larger (bulkier) than the internal diameter of the ring or oculi of the macrocyclic host molecule, and therefore prevents the disassociation or unthreading of a rotaxane-complex components, by not being able to pass through the ring or oculi without significant distortion or breakage of one or more covalent bonds in either one of the stopper moiety, the host molecule or both. Specifically, in the context of a rotaxane, the bulkiness of the stopper moiety is reflected in the projection of the maximal diameter of the stopper moiety on a plane that is normal to the longitudinal-axis of the threading moiety, which is larger than the internal diameter of the ring or oculi of the macrocyclic host molecule.

According to some embodiments of the present invention the stopper moiety is selected from the group consisting of a branched alkyl moiety, a branched cycloalkyl moiety, a branched heteroalicyclic moiety, a branched polyaryl moiety, a branched polyheteroaryl moiety, an adamantly moiety, a branched organophosphorous, a branched organoboron, a branched organosilicon and a branched carboranes.

The term "branched" as used in the context of the stopper moiety, refers to chemical moieties which are characterized by a large cross-section relative to the oculi of the cucurbituril, based on a center atom or heteroatom, which carries more than one and preferably more than two substituents, and therefore is termed branched.

As used herein, the term "alkyl" describes an aliphatic hydrocarbon including straight chain and branched chain groups. According to some embodiments of the present invention, the alkyl group has 1 to 10 carbon atoms. An alkyl having 1 to 4 carbon atoms is typically referred to as a low-alkyl. Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms. The alkyl can be substituted or unsubstituted.

The term "alkyl", as used herein, also encompasses cyclic saturated or unsaturated hydrocarbon, hence this term further encompasses cycloalkyl, alkenyl and alkynyl.

The term "alkenyl" describes an unsaturated alkyl, as defined herein, having at least two carbon atoms and at least one carbon-carbon double bond. The alkenyl may be substituted or unsubstituted by one or more substituents, as described herein.

The term "alkynyl", as defined herein, is an unsaturated alkyl having at least two carbon atoms and at least one carbon-carbon triple bond. The alkynyl may be substituted or unsubstituted by one or more substituents, as described herein.

As used herein, the term "cycloalkyl" refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane.

The term "heteroalicyclic" refers to a monocyclic or fused ring group having in the ring(s) one or more atoms such as nitrogen, oxygen and sulfur. The rings may also have one or more double bonds. However, the rings do not have a completely conjugated pi-electron system.

The term "aryl" refers to an all-carbon monocyclic or fused-ring polycyclic (i.e., rings which share adjacent pairs of carbon atoms) group having a completely conjugated pi-electron system. Examples, without limitation, of aryl groups are butadiene, phenyl, naphthalenyl and anthracenyl.

The term "heteroaryl" includes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

The term "organophosphorus", as used herein, encompasses all groups which contain a phosphorus atom, P, such as phosphine ($PR_3$), phosphine oxide ($OPR_3$), phosphinite ($P(OR)R_2$), phosphonite ($P(OR)_2R$), phosphite ($P(OR)_3$), phosphinate ($OP(OR)R_2$), phosphonate ($OP(OR)_2R$) and phosphate ($OP(OR)_3$), wherein each R is independently hydrogen, alkyl, cycloalkyl, heteroalicyclic, aryl and heteroaryl.

The terms "organoboron" or "organoborane", as used herein, encompass all groups which contain a boron atom, B, such as alkylborane ($BR_3$), borinic esters ($R_2BOR$), boronic esters ($RB(OR)_2$) and borates $RB(OR)_3$, wherein R is as defined hereinabove. This term includes the family of carboranes, which are bulky and typically polyhedral clusters composed of boron and carbon atoms.

The terms "organosilicon", "organosilyl" and "organosilane", as used herein, encompass all groups which contain a silicon atom, Si, substituted with —R or —OR, wherein R is as defined hereinabove.

In the context of a stopper moiety, the above moieties and groups are substituted such that the overall cross-section of the resulting moiety is larger than the oculi of the CB. Hence, a branched alkyl moiety, as well as a branched cycloalkyl moiety, a branched heteroalicyclic moiety, a branched polyaryl moiety, and a branched polyheteroaryl moiety, may all be based on a center atom, heteroatom, aryl or heteroaryl, which is poly-substituted with alkyl, cycloalkyl, heteroalicyclic, aryl and heteroaryl or a combination thereof.

The stopper moiety, according to some embodiments of the present invention, can also act as an anchoring group, an effector moiety and a detectible moiety, as these are defined hereinbelow, provided that the stopper moiety is not positively charged.

Exemplary stopper moieties are presented in the Examples section that follows, and specifically illustrated in Scheme 3, Scheme 10, Scheme 12, Scheme 14, Scheme 15 and Scheme 25.

The phrase "threading moiety" describes a chemical moiety which is capable of penetrating through a macrocyclic host molecule. According to some embodiments of the present invention, a threading moiety is an elongated, linear and rigid chemical moiety, which is characterized by a longitudinal-axis and a cross-section that are suitably sized to fit the inner part of the host molecule. In a case of a cavitand host molecule, the longitudinal-axis of the threading moiety is long enough to allow the threading moiety to reach from one oculus of the cavitand to the other, while the cross-section of the threading moiety is narrow enough to allow the threading moiety to penetrate, or thread into the cavitand oculi.

According to some embodiments of the present invention, the macrocyclic host molecule is a cucurbituril (an exemplary cavitand), and the threading moiety is capable penetrating through the cucurbituril's oculi and occupying its cavity. According to other embodiments of the present invention, the threading moiety is substantially hydrophobic, and thus at least a portion of the threading moiety is capable of interacting with the hydrophobic cavity of the cucurbituril.

Additionally, according to other embodiments, the threading moiety is substantially linear and rigid, and can be much longer that the longitudinal-axis of the host molecule, such that the host molecule can travel along the threading moiety without any or little energy barriers associated with such axial and linear motion.

The term "linear", as used herein, refers to a geometrical attribute of a molecule or a part thereof, which is substantially straight, narrow and elongated along one dimension.

The term "rigid", as used herein, refers to a configurational attribute of a molecule or a part thereof, which is substantially unbendable along its longitudinal-axis and has no bonds which can rotate away from its longitudinal-axis. According to some embodiments, the threading moiety is substantially rigid, and hence the bonds along its longitudinal-axis may only rotate around an axis which is parallel and co-axial with the longitudinal-axis of the moiety.

Thus, threading moieties according to some embodiments of present invention are characterized by a chemical structure of which at least a portion is linear, rigid, and in some embodiments also hydrophobic, and which can thread (be inserted or penetrate) into and interact with a cucurbituril cavity without significant distortion or breakage of one or more covalent bonds in either one of the threading moiety, the host molecule or both. Exemplary threading moieties according to some embodiments of the present invention, includes without limitation, a polyyne moiety, a polyaryl moiety and a polyheteroaryl moiety.

According to some embodiments of the present invention, the threading moiety is a form of a rigid and linear polymer or mixed polymer, represented by $[A]_m$ wherein m represents the number of monomers or repeats, and A is a monomeric unit. Thus, in some embodiments, m is an integer that is equal to 1, 2, 3, 4, 5 or 6, which correspond to a threading moiety of one monomeric unit, two monomeric units, three monomeric units, four monomeric units, five monomeric units and six monomeric units, respectively.

According to some embodiments of the present invention, A is selected from the group consisting of a 1,2-ethyn-di-yl, a substituted or unsubstituted aryl, a substituted or unsubstituted heteroaryl, substituted or unsubstituted cyclobuta-1,3-diene-1,3-di-yl, substituted or unsubstituted pentalene-2,5-di-yl, substituted or unsubstituted benzene-1,4-di-yl, substituted or unsubstituted pyrene-2,7-di-yl, C-substituted or unsubstituted pyridine-2,5-di-yl, C-substituted or unsubstituted pyrimidine-2,5-di-yl, C-substituted or unsubstituted pyrazine-3,6-di-yl and 1,2,4,5-tetrazine-3,6-diyl.

For example, $[A]_m$ wherein A is 1,2-ethyn-di-yl and m is 3 corresponds to a hexa-1,3,5-triyne threading moiety.

The major attribute which renders any aromatic ring system suitable to form a part of an aromatic threading moiety is the ability to disubstitute the aromatic core in such a way that will form an overall linear shape, namely be extendable in two opposite directions.

Thus, aryl moieties which are linked to one another via opposing apex (para-relative positions) positions can be used to construct aromatic threading moieties. For example, 1,3-di(cyclobuta-1,3-dienyl)cyclobuta-1,3-diene is a threading moiety where A is cyclobuta-1,3-diene-1,3-di-yl and m is 3. In another example, 2-yl-5-(5-yl-1,3a-dihydropentalen-2-yl)-1,3a-dihydropentalene is a threading moiety where A is pentalene-2,5-di-yl and m is 2.

In cases where the aryl has ring position which are free for substitution, these positions can by substituted with a number of substituents which are suitable for occupying the cavitand, such as small electron-rich or otherwise uncharged substituents like halo or a low alkyl group. Hence substituted or unsubstituted aryls can be used as a monomeric unit in the aromatic threading moiety. Similarly, heteroaryl units can serve as monomeric units in a heteroaryl-based aromatic threading moiety. For example, 6-yl-3-(6-yl-2,3-dihydro-1,2,4,5-tetrazin-3-yl)-1,6-dihydro-1,2,4,5-tetrazine is a heteroaryl-based aromatic threading moiety wherein A is 1,2,4,5-tetrazine-3,6-diyl and m is 2.

Heteroaryl units in a threading moiety can also be substituted at any free carbon position according to some embodiments of the present invention. Hence, heteroaryls C-substituted with small and uncharged substituents may also serve as a monomeric subunit in the uncharged threading moiety.

Exemplary threading moieties, base on the above-mentioned monomeric subunits, are presented in the Examples section that follows, and specifically in Scheme 4

Scheme 5, Scheme 6 and Scheme 7.

As used herein, the phrase "linking moiety" describes a chemical moiety, a group or a bond, as defined herein, which links a threading moiety and a stopper moiety. The linking moiety can thus be, for example, formed upon reacting two functional groups; each functional group forms a part of a molecule or a moiety in a molecule, thus linking the two molecules of moieties. For example, an amine group on one molecule or moiety can form bond with a carboxyl group on another molecule or moiety and the resulting linking moiety is an amide (peptide) bond linking moiety. In another example, an azide on one molecule and an alkyne on another molecule typically affords a 1,2,3-triazole linking moiety in what is known as a Huisgen cycloaddition, or as 1,3-dipolar cycloaddition.

According to some embodiments of the present invention, the linking moiety is selected from the group consisting of alkyl, alkenyl, alkynyl, cycloalkyl, heteroalicyclic, aryl, heteroaryl, ether, thioether, amide, ester, carbamate, thioamide, thiocarbamate, imine, aza, organophosphorous, organoboron and organosilicon.

The term "ether", as used herein, refers to a —O— group, being a linking moiety with consist of an oxygen atom.

The term "thioether", as used herein, refers to a —S— group, being a linking moiety with consist of a sulfur atom.

As used in the context of a linking moiety, the term "amide" refers to a —NR—C(=O)— group, wherein R is as defined hereinabove.

The term "ester" in the context of a linking moiety refers to a —C(=O)—O— group.

The term "carbamate" in the context of a linking moiety refers to a —NR—C(=O)—O— group, wherein R is as defined hereinabove.

The term "thioamide" in the context of a linking moiety refers to a —NR—C(=S)— group, where R is as defined herein.

The term "thiocarbamate" in the context of a linking moiety refers to a —NR—C(=S)—O— group, a NRC(=S)—S— group or a NRC(=O)—S— group, wherein R is as defined hereinabove.

The term "imine", also known as Schiff base, refers in the context of a linking moiety to a —NR=CR'— group, where R is as defined herein and R' is as defined for R.

The term "aza" bond refers in the context of a linking moiety to a —N=N— group.

The linking moiety connects the stopper moiety to the threading group, and can also connect U and/or Y thereto.

As presented hereinabove, U and Y are each independently selected from the group consisting of an anchoring group, an effector moiety, a detectible moiety, a biomolecule, as these are defined and discussed in details hereinbelow, or absent.

The phrase "anchoring group", as used herein, refers to a functional group on a molecule that can be used to attach the molecule to another molecule by a covalent bond, ionic bond, dipole-dipole interaction, a metal coordination bond, a hydrogen bond(s) or any other attraction/bonding forces.

According to some embodiments of the present invention, the anchoring group can be used to attach the molecule to a solid support via a functional group on the surface of the solid support, as this is discussed hereinunder.

Alternatively, the anchoring moiety can be used to link between two rotaxanes, according to some embodiments of the present invention, and therefore conjugate the two and form a conjugated system that can propagate energy therethrough. Such a conjugation can be elongated to an unlimited number of rotaxanes if each comprises more than one anchoring moieties.

As used herein, the phrase "functional group" describes a chemical group that is capable of undergoing a chemical reaction that typically leads to a bond formation. The bond, according to the present embodiments, is preferably a covalent bond. Chemical reactions that lead to a bond formation include, for example, nucleophilic and electrophilic substitutions, nucleophilic and electrophilic addition reactions, addition-elimination reactions, cycloaddition reactions, rearrangement reactions and any other known organic reactions that involve a functional group. As used herein, the phrase "effector moiety" describes a chemical moiety which is capable of interacting with an external source of energy or force, such as an electromagnetic flied, light, electric field, magnetic field, heat, kinetic energy, chemical energy and the likes. According to some embodiments of the present invention, the effector can transmit the energy to another moiety in the guest molecule, to another moiety in the host molecule, or to other moieties of another molecule. The transmitted energy can be in its original form or in any other type of energy. A detailed discussion of effector moieties and their uses follows hereinbelow.

According to some embodiments of the present invention, the cucurbit[n]uril host may include one or more functionalities attached thereto. Functionalized cucurbiturils are well know in the art [60], and are readily prepared so as to include many attached moieties. In the context of the present embodiments, these moieties include an anchoring group, an effector moiety, a detectible moiety and a biomolecule, as these as defined herein.

The process of preparing the rotaxane as presented hereinabove is effected by providing a complex, or a precursor rotaxane, which includes a cucurbit[n]uril (CB [n]) host molecule as described hereinabove, and a positively charged guest molecule having an affinity to the cucurbituril. This precursor is processed into the present rotaxane by substantially neutralizing the positively charged group(s) in the guest molecule to thereby obtain the rotaxane wherein the host and the guest so not exhibit high affinity to one another.

According to this aspect of the present invention, the charged guest molecule has a general formula selected from the group consisting of Formula II or Formula III:

  Formula II

  Formula III wherein:

$L'_1$ and $L'_2$ are each independently an affinity moiety or one of $L'_1$ and $L'_2$ is absent, and at least one of $L'_1$ and $L'_2$ independently comprises a positively charged group;

$[A]_m$ is an uncharged threading moiety as defined hereinabove;

m is an integer that ranges from 1 to 50;

$L_1$ is an uncharged linking moiety as defined hereinabove or absent;

$B_1$ and $B_2$ are each independently an uncharged stopper moiety as defined hereinabove;

U and Y are as defined hereinabove or absent.

The phrase "affinity moiety", as used herein, refers to a chemical moiety which exhibits an affinity to cucurbit[n]urils in general, and to the carbonyl-lined oculi thereof in particular. For example, positively charged groups such as ammonium groups, and particularly quaternary ammonium groups, have a remarkable affinity to the carbonyl-lined oculi of cucurbit[n]urils. According to some embodiments of the present invention, the presence of an affinity moiety in a molecule will favor the formation of a complex between to molecule and a cucurbit[n]uril molecule. In cases where an affinity moiety is attached to one end of a threading moiety, as defined herein, the cucurbit[n]uril molecule is more likely to host the threading moiety therein in such a configuration that will allow the affinity moiety to occupy one of its oculi. When two such affinity moieties are found in one molecule, linked by a threading moiety, as defined herein, the affinity effect exerted by the two affinity moieties towards the cucurbit[n]uril molecule is increased dramatically, as discussed in great details in the art (see, for example, Lagona et al. [60])

The phrase "positively charged group", as used herein, refers to an atom or a group of atoms which forms a part of an organic molecule, and which is characterized by a positive electrostatic charge. Compounds which include one or more positively charged groups are molecular ions oftentimes referred to as molecular cations. A positively charged group of atoms has at least one electron less than the number of protons in these atoms. Positively charged groups include, for a non-limiting example, ammonium and sulfonium groups.

A positively charged group is one that retains its charge stays ionized in a pH range from about 6 to about 8. In some cases a positively charged group is not capable of participating in proton-exchange interactions at that pH range. It is noted herein that the physiological pH is about 7.4; therefore a positively charged group which retains its charge at physiological pH refers to a positively charged chemical group that stays ionized in a pH range of about 5-8.

Quaternary ammonium groups are known to be positively charged at any pH range, including the physiological pH range, hence the positively charged group, according to preferred embodiments of the present invention, is a quaternary ammonium group.

The phrase "quaternary ammonium", as used herein, refers to a nitrogen atom which forms a part of a molecule (an amine, as defined hereinbelow) that is attached to four non-hydrogen substituents and thus is positively charged. Thus, according to some embodiments of the present invention, the positively charged group is a quaternary ammonium.

As used herein, the term "amine" describes a —NRR group where each of R and R is independently hydrogen, alkyl, cycloalkyl, heteroalicyclic, aryl or heteroaryl, as these terms are defined herein.

Since the rotaxanes of the present invention are characterized by not having an attractive interaction between the host and the guest, the positive charge which is present in the precursor rotaxane is neutralized.

The term "neutralizing", as used herein, refers to the action of eliminating an electrostatic charge in a charged molecule or moiety, thus rendering it an uncharged molecule or moiety, as these terms are defined herein. For example, a positively charged amine group (an ammonium group) can be neutralized by oxidation of the amine group into an N-oxide group. Subsequently, the N-oxide can be converted, for example, to an alkene by prolytic elimination effected by heat following a pyrolytic syn-elimination procedure is known as a Cope reaction, or Hofmann elimination.

As discussed hereinabove, the formation of a cucurbit[n]uril-based rotaxane depends and in some cases strongly relies on the presence of moderately high affinity between the CB[n] and the positively charged guest molecule, and therefore the formation of the precursor rotaxane may still rely on having a threading moiety having at least one positively charged affinity moiety attached thereto.

Hence, according to some embodiments of the present invention, the process of preparing the present rotaxane further includes, prior to the neutralization process, preparing the precursor rotaxane by contacting the cucurbit[n]uril with a compound having a general formula selected from the group consisting of Formula IV, Formula V or Formula VI:

$R_1$-$L'_1$-$[A]_m$-$L'_2$-$R_2$    Formula IV

U—$B_1$-$L'_1$-$[A]_m$-$L'_2$-$R_2$    Formula V

U—$B_1$-$L_1$-$[A]_m$-$L'_2$-$R_2$    Formula VI wherein the various variables are as defined hereinabove;

$L'_1$ and $L'_2$ are each independently an affinity moiety or one of $L'_1$ and $L'_2$ is absent, and at least one of $L'_1$ and $L'_2$ independently comprises a positively charged group; and $R_1$ and $R_2$ are each independently a reactive group.

This step provides a complex between the cucurbit[n]uril and the compound having a reactive group, via at least one of the affinity moieties mentioned above.

The phrase "reactive group", as used herein, refers to functional group which more reactive, namely more likely to react in specific conditions which favour a specific reaction, as compared to other functional groups which are present in one or more of the reactants in a given reaction mixture. For a non-limiting example, a reactive group may include, without limitation, an alkyne (—C≡C—), a azide (—N=N⁺=N), an acyl-halide, an anhydride and the likes.

This complex, also known in the art as a pseudorotaxane (for not having two stopper groups), is now reacted with another compound having the general Formula VII and/or a compound having the general Formula VIII:

U—$B_1$—$R_4$    Formula VII

$R_3$—$B_2$—Y    Formula VIII wherein the various variables are as defined hereinabove; and $R_3$ and $R_4$ are each independently a reactive group.

This step of the process caps one or both ends of the threading moiety with stopper group(s), and thereby the precursor rotaxane is formed, having a positively charged guest molecule within the cucurbit[n]uril.

According to another aspect of the present invention, the present rotaxane can be prepared by an alternative route wherein the guest molecule having uncharged threading moiety, uncharged linking moieties and uncharged stopper moieties is formed by capping the guest molecule while it being threaded in the cucurbituril.

Hence, there is provided a process of preparing the rotaxane presented herein, which is effected by contacting the cucurbit[n]uril with a compound having the general Formula IX:

U—$B_1$-$L_1$-$[A]_m$-$L'_2$-$R_2$    Formula IX wherein the various variables are as defined hereinabove;

$L_1$ is an uncharged linking moiety or absent;

$B_1$ is an uncharged stopper moiety;

$L'_2$ is an affinity moiety which comprises a positively charged group; and $R_2$ is a reactive group.

This step forms the pseudo-rotaxane complex between the cucurbit[n]uril and the compound having the general Formula IX, effected by the positively charged group.

The process further includes contacting this pseudo-rotaxane complex with a compound having the general Formula X:

$R_3$—$B_2$—Y    Formula X wherein:

$R_3$ is a reactive group;

$B_2$ is an uncharged stopper moiety; and

Y is selected from the group consisting of an anchoring group, an effector moiety, a detectible moiety, a biomolecule, or absent.

This step caps the guest molecule and at the same time substantially neutralizes the positively charged group and thereby forms the present rotaxane.

According to some embodiments of the present invention, in all the processes presented hereinabove, $R_3$ is also an affinity moiety.

Further according to some embodiments of the present invention, the cucurbit[n]uril used in any of the processes presented hereinabove is attached to a solid support during the entire process.

Alternatively, according to some embodiments of the present invention, the cucurbit[n]uril used in any of the processes presented hereinabove is attached to another cucurbituril, or to any of the compounds having the general Formula II, Formula III, Formula V, Formula VI, Formula VII, Formula VIII, Formula IX and Formula X, via any one of U or Y.

Further according to some embodiments of the present invention, any one of U or Y which may be present in any of the compounds having the general Formula II, Formula III, Formula V, Formula VI, Formula VII, Formula VIII, Formula IX and Formula X, is attached to a solid support prior to said contacting.

Alternatively, according to some embodiments of the present invention, any of the compounds having the general Formula II, Formula III, Formula V, Formula VI, Formula VII, Formula VIII, Formula IX and Formula X, is attached to another one of these compounds, or to a cucurbituril, via any one of U or Y.

As discussed hereinabove, the present rotaxane can be attached either during the process of it preparation or thereafter, to a solid support.

The phrase "solid support" as used herein encompasses solid supports such as, but not limited to, solid surfaces of any material, polymers, resins, beads, including plastic beads, metal beads and magnetic beads, silica matrices such as glass and sol-gel particles and the like. The material of the solid support is selected such that it is insoluble in the media in which it is used.

The term "surface" as used herein refers to any outer boundary of an artifact or a material layer constituting or resembling such a boundary.

The term "polymer" refers to a naturally occurring or synthetic compound consisting of large molecules made up of a linked series of repeated simple monomers.

The term "resin" refers to any of a class of solid or semi-solid viscous substances obtained either as exudations from certain plants or prepared by polymerization and cross-linking of simple molecules.

The phrase "sol-gel" as used herein refers to a versatile solution process for making ceramic and glass materials. In general, the sol-gel process involves the transition of a system from a liquid "sol" (mostly colloidal) into a solid "gel" phase. Applying the sol-gel process, it is possible to fabricate ceramic or glass materials in a wide variety of forms: ultra-fine or spherical shaped powders, thin film coatings, ceramic fibers, microporous inorganic membranes, monolithic ceramics and glasses, or extremely porous aerogel materials.

Hence, according to another aspect of the present invention, there is provided a composition-of-matter which includes the rotaxane presented herein attached to a solid support.

According to yet another aspect of the present invention, there is provided a composition-of-matter which includes a plurality of the rotaxane presented herein, attached to a solid support.

The plurality of rotaxanes can be attached to a solid support in various arrangements, such as an array having discrete locations for individual rotaxane or groups thereof, as a two dimensional layer or film, or in any other pattern.

According to still another aspect of the present invention, there is provided a composition-of-matter which includes a plurality of the rotaxane presented herein attached to one another.

As discussed hereinabove, in all the compositions presented herein, the rotaxane can be attached to a solid support, to another rotaxane or both, via any one of the anchoring moieties present in any one of U and Y or on any one of the cucurbituril hosts.

As presented hereinabove, any one of U and Y found in the guest molecule can be an effector moiety, a detectable moiety or a biomolecule, and the cucurbituril host may also be functionalized with one or more effector moieties, detectable moieties or biomolecules. These appendices or attachments bestow particular functionality to the rotaxane, and particularly when it is attached to a solid support.

As presented hereinabove and according to some embodiments of the present invention, an effector moiety can transmit energy to another moiety or molecule, and the transmitted energy can be in its original form or in any other form of energy.

Non-limiting examples of effector moieties include charged groups and moieties (such as ammonium groups, guanidinium groups, carboxylate groups, sulfonate groups and the likes), a metal ion complex moiety (such as a chelating moiety that contains one or more metal ions), a magnetic moiety (such as a chelating moiety that contains one or more ferromagnetic or paramagnetic moieties, including metal ions), a light absorbing moiety (such as a moiety that absorbs electromagnetic radiation, such as UV, visible, IR, microwave, radio and the likes).

By interacting with such an external source of energy or force, the rotaxane, which the effector moiety is attached thereto, can act as an energy converter which can transform one form of energy to another form of energy.

Thus, according to some embodiments of the present invention, any of the compositions presented herein can be selected to have suitable effector moieties, such that render the composition capable of converting energy from one form to another.

For a non-limiting example, the effector moiety is capable of absorbing electromagnetic radiation in the microwave range, and cause the host and the guest of the rotaxane to rotate with respect to one-another, thereby converting the electromagnetic radiation energy to rotational kinetic energy, which in turn can be converted to heat (translational kinetic energy).

In another example, the effector moiety includes a paramagnetic metal which interacts with an external magnetic force field, and cause the host and the guest of the rotaxane to rotate with respect to one-another, thereby converting the magnetic force field to rotational kinetic energy, which in turn can be converted to heat (translational kinetic energy).

Alternatively, according to some embodiments of the present invention, one effector moiety on one side of the guest molecule includes a ferromagnetic metal, and another effector moiety on the other side of the guest molecule can interact with microwave radiation. This exemplary rotaxane can absorb the electromagnetic radiation in the microwave range, and convert it via rotational kinetic energy to a magnetic field effected by the rotating ferromagnetic metal.

Such energy converters based on the rotaxane presented here constitute a "frictionless" molecular motor. The motor attribute stems from the capacity to convert one source of energy to rotational energy and vice-versa, and the frictionless attribute arises from low affinity or lack thereof between the stator, namely the cucurbituril host molecule, and the rotor, namely the guest molecule.

When any one or more of the aforementioned appendices or attachments is a detectable moiety or a biomolecule, the compositions presented herein can be used to construct biochips, sensors and biosensors, and many other devices. The capability to attach such appendices, with or without the combination of effector moieties, on a rotatable element such as the present rotaxane, grants an advantage to these device over similar devices based on stationary elements.

As used herein, the phrase "detectable moiety", describes an agent or a moiety that exhibits a measurable feature. This phrase encompasses the phrase "diagnostic agent", which describes an agent that upon administration to a subject exhibits a measurable feature that corresponds to a certain medical condition in vivo. Such agents and moieties include, for example, labeling compounds or moieties, as is detailed hereinunder.

Representative examples of detectable moieties include, without limitation, signal generator agents and signal absorber agents.

As used herein, the phrase "signal generator agent" includes any agent that results in a detectable and measurable perturbation of the system due to its presence. In other words, a signal generator agent is an entity which emits a detectable amount of energy in the form of electromagnetic radiation (such as X-rays, ultraviolet (UV) radiation, infrared (IR) radiation, microwave, radio and the like) or matter, and includes, for example, phosphorescent and fluorescent (fluorogenic) entities, gamma and X-ray emitters, (such as neutrons, positrons, α-particles, β-particles, and the like) and radionuclides, as well as paramagnetic or ferromagnetic entities.

As used herein, the phrase "signal absorber agent" describes an entity which absorbs a detectable amount of energy in the form of electromagnetic radiation or matter. Representative examples of signal absorber agents include, without limitation, dyes, contrast agents, electron beam specifies, aromatic UV absorber, and boron (which absorbs neutrons).

As used herein, the phrase "labeling compound or moiety" describes a detectable moiety or a probe which can be identified and traced by a detector using known techniques such as spectral measurements (e.g., fluorescence, phosphorescence), electron microscopy, X-ray diffraction and imaging, positron emission tomography (PET), single photon emission computed tomography (SPECT), magnetic resonance imaging (MRI), computed tomography (CT) and the like.

Representative examples of labeling compounds or moieties include, without limitation, chromophores, fluorescent compounds or moieties, phosphorescent compounds or moieties, contrast agents, radioactive agents, magnetic compounds or moieties (e.g., diamagnetic, paramagnetic and ferromagnetic materials), and heavy metal clusters, as is further detailed hereinbelow, as well as any other known detectable moieties.

As used herein, the term "chromophore" refers to a chemical moiety or compound that when attached to a substance renders the latter colored and thus visible when various spectrophotometric measurements are applied.

A heavy metal cluster can be, for example, a cluster of gold atoms used, for example, for labeling in electron microscopy or X-ray imaging techniques.

As used herein, the phrase "fluorescent compound or moiety" refers to a compound or moiety that emits light at a specific wavelength during exposure to radiation from an external source.

As used herein, the phrase "phosphorescent compound or moiety" refers to a compound or moiety that emits light without appreciable heat or external excitation, as occurs for example during the slow oxidation of phosphorous.

As used herein, the phrase "radioactive compound or moiety" encompasses any chemical compound or moiety that includes one or more radioactive isotopes. A radioactive isotope is an element which emits radiation. Examples include α-radiation emitters, β-radiation emitters or γ-radiation emitters.

The term "biomolecule", as used herein, refers to any organic molecule that occurs naturally in living organisms. As used herein, biomolecules are substantially organic as oppose to inorganic, namely carbon-based compounds which consist primarily of the elements carbon and hydrogen, typically in combination with nitrogen, oxygen, phosphorus and sulfur, as well as other less common elements. In the context of the present embodiments, the term biomolecules encompasses small and simple compounds, such as the smallest building block of macro-biomolecule, as well as the entire macro-biomolecule itself and any intermediate size or part thereof.

One non-limiting example of a family of biomolecules includes amino acids, which are some of the most abundant and prevalent building blocks in nature. Amino acids are monomeric biomolecules that are used to construct polymers known as peptide, oligopeptide, polypeptide and/or protein of all chain length and size.

Another non-limiting example of a family of biomolecules includes nucleotides, which comprise a heteroaryl moiety (a purine or a pyrimidine base), a sugar moiety (pentose sugar) and an inorganic phosphate group. Naturally occurring nucleotides (cytidine, uridine, adenosine, guanosine, thymidine and inosine) are the monomeric biomolecules which are used to construct biomolecular polymers known as nucleic acids (DNA and RNA) of all chain length and sizes.

Other exemplary biomolecules include, without limitation, glycoproteins, metalloproteins, lipids, phospholipids, glycolipids, sterols, vitamins, hormones, neurotransmitters, carbohydrates, sugars, monosaccharides (hexoses glucose, fructose, and galactose and pentoses, ribose and deoxyribose), dinosaccharides (such as sucrose, maltose and lactose), oligosaccharides, polysaccharides (such as starch, cellulose and glycogen), nucleosides and the likes.

It is noted that the term "biomolecule" as used herein is meant to encompass any functional analog and derivative of a naturally occurring biomolecule.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions; illustrate the invention in a non limiting fashion.

Example 1

Molecular Mechanics Calculations

An exemplary stator-rotator molecular rotary motor system according to some embodiments of the present invention, having rotaxane architecture, consisting of a rigid and linear hexadiyne moiety capped with a trioxoadamantyl stopper moiety on each end serving as a rotator, and a CB[6] (Compound 1) serving as a stator, is illustrated in Scheme 2 below.

Scheme 2

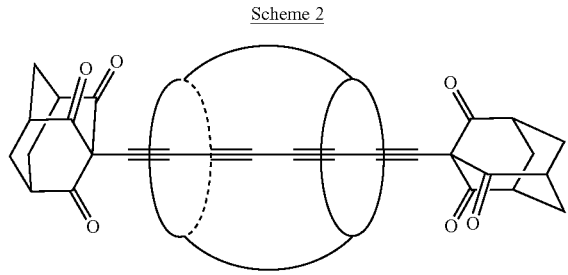 [SMILES: O=C1C2CC3CC(C2)C(=O)C1(C#CC#CC#CC#CC12C(=O)C4CC(CC(C4)C1=O)C2=O)C3=O]

This molecular motor system is characterized by repulsive interactions between the diyne rod and the interior of the CB[6], owing to the high electron density of both diyne and the interior of the CB[6]. It was expected that the 48 non-bonding electrons of the carbonyl oxygens of the CB[6] and the filled n-orbitals of the 12 urea groups thereof would repel the π-electrons of the diyne rod. Consequently, it was predicted that when the polyyne rod is inserted into the cavity of the CB[6], the repulsive interaction should keep it floating at the center of the cavity in perfect alignment with the 6-fold symmetry axis of the CB[6].

Considering the requirement of low friction and the general architecture of a rotaxane, the two stopper moieties afford a second mode of repulsive interaction between the two molecular components of the system; one that minimizes the friction between the portals of the CB[6] and the bulky stopper moieties. This requirement is achieved by selecting stopper moieties equipped with a strong dipole moment that opposes the dipole moment of the portal, namely the carbonyl groups on the two trioxoadamantyl moieties (see, Scheme 3 hereinabove). Such repulsive interactions would maintain the two stopper moieties floating at a maximal distance from the portals. Since there are no states that define a rotation of a polyyne along its long axis, the expected rotation refers to the relative motion of the CB[6] host and the bulky stopper moieties.

In order to verify the above predictions, energy minimization analysis of the hypothetical stator-rotator molecular rotary motor systems illustrated in Scheme 3 below, namely CB[6]-polyalkynes systems I, II, and III, were carried out using the MOLOC software [76, 77]. The adamanty stopper moieties in II represent a fully saturated hydrocarbon stopper moiety while the triphenylmethyl stopper moieties in III represent any polyaromatic stopper moiety.

Scheme 3

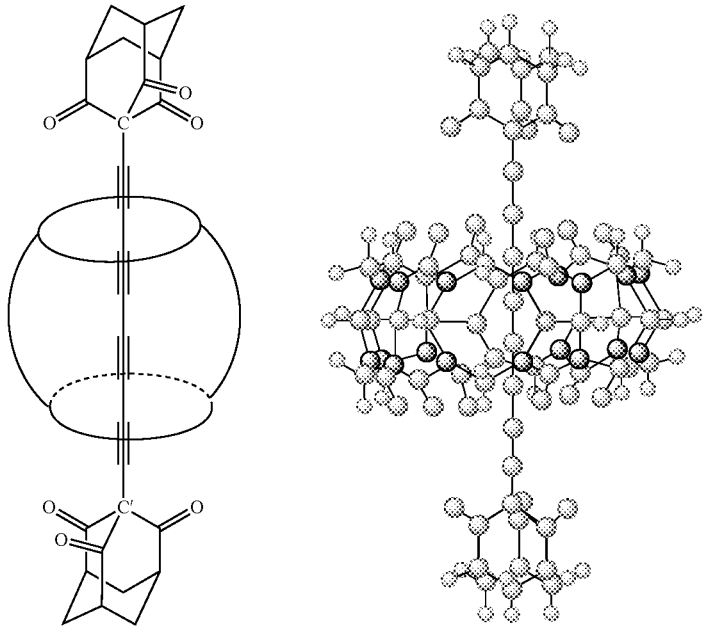

I

-continued

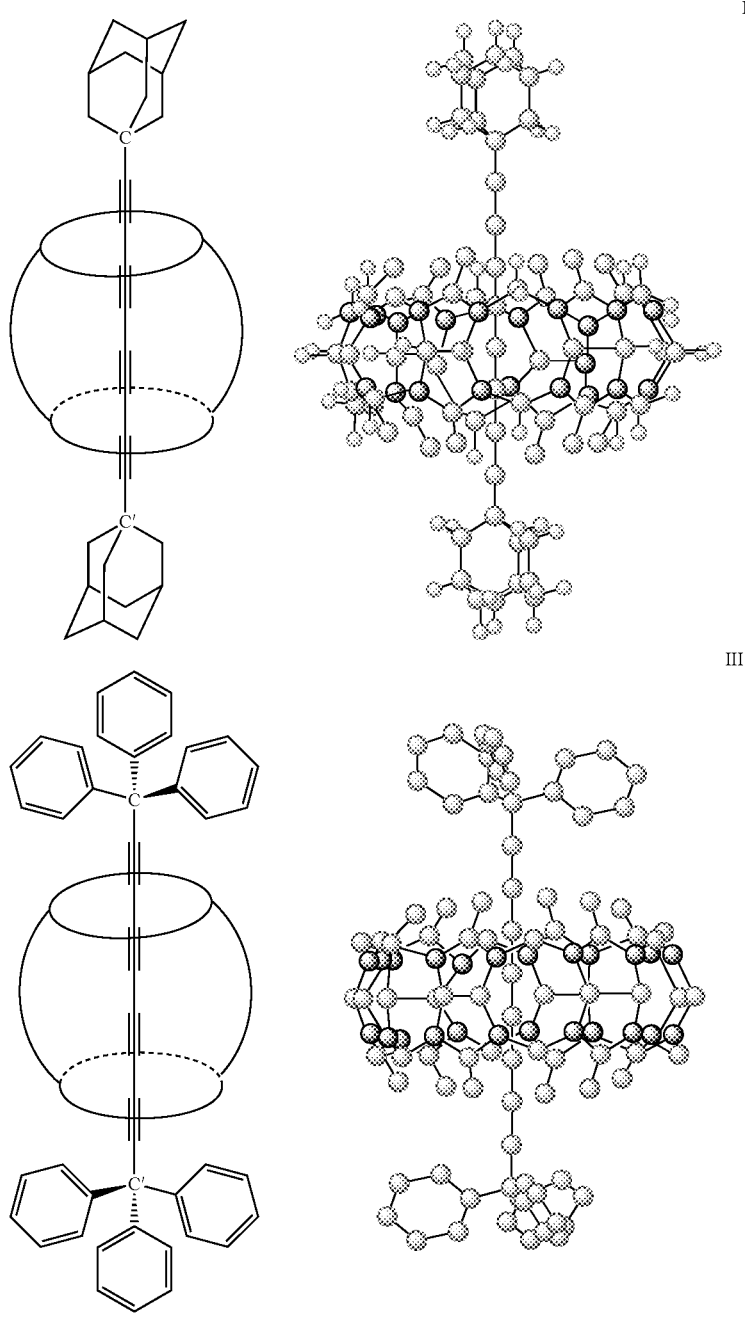

The calculated inter-atomic distances between the propargylic carbons C and C' (denoted C and C' in Scheme 3) and each of the carbonyl oxygen atoms of the adjacent CB[6] portal, referred to as $O_1$-$O_6$ for one portal and $O_7$-$O_{12}$ for the second portal, are presented in Table 1.

TABLE 1

| Atoms | I | II | III |
|---|---|---|---|
| C—$O_1$ | 4.55 | 5.33 | 4.51 |
| C—$O_2$ | 4.55 | 5.36 | 4.52 |
| C—$O_3$ | 4.55 | 5.24 | 4.57 |
| C—$O_4$ | 4.55 | 5.28 | 4.23 |
| C—$O_5$ | 4.56 | 5.16 | 4.68 |
| C—$O_6$ | 4.56 | 5.18 | 4.37 |
| Average | 4.553 ± 0.007 | 5.25 ± 0.11 | 4.48 ± 0.23 |
| C'—$O_7$ | 4.56 | 3.95 | 4.7 |
| C'—$O_8$ | 4.56 | 3.96 | 4.76 |
| C'—$O_9$ | 4.55 | 3.96 | 4.61 |
| C'—$O_{10}$ | 4.55 | 3.94 | 4.56 |
| C'—$O_{11}$ | 4.55 | 3.94 | 4.6 |
| C'—$O_{12}$ | 4.55 | 3.97 | 4.53 |
| Average | 4.553 ± 0.007 | 3.95 ± 0.01 | 4.62 ± 0.14 |

As can be seen in Table 1, the calculated inter-atomic distances matched the above predictions. In I, which represents the extreme case of a repulsive dipole-dipole interaction, both stopper moieties are positioned at a maximal distance from the portal with equal inter-atomic distances between either C or C' and any of the close carbonyl oxygens (4.55-4.56 Å). In contrast, II represents a case wherein there is some attractive interaction between the stopper moieties and the near CB[6] portal. Apparently, the CB[6] in II is positioned non-symmetrically between the two stopper moieties with one of them floating closer to the portal (3.95±0.01 Å) while the other staying at a much longer distance (5.25±0.11 Å). System III represents an intermediate case where the CB[6] is positioned at approximately equal distances from the two stopper moieties (4.48±0.23 and 4.62±0.14 Å) but with significant departure of the stopper moieties from the 6-fold axis. This situation is assumed to reflect some attractive interaction between the aromatic rings of the stopper moieties and the CB[6] portals.

Example 2

Chemical Syntheses

Materials and Methods:

All starting materials were purchased from known commercial sources unless stated otherwise. THF was dried and distilled over sodium/benzophenone and DMF was dried and distilled over $CaH_2$.

$^1$H NMR, $C^{13}$ NMR spectra were recorded on a Bruker Ultrashield AV300 spectrometer, operating at 300 MHz ($^1$H) or 75.44 MHz ($^{13}$C), using $CDCl_3$ as a solvent unless specified otherwise. Chemical shifts reported (in ppm) are relative to internal $Me_4Si$ ($\delta$=0.0).

CI-MS spectra were measured on a Finnigan TSQ-70 spectrometer and MALDI-TOF spectra were measured on a MALDI Micromass spectrometer using α-ciyano-4-hydroxycinnamic acid as a matrix.

TLC was performed on glass sheets pre-coated with silica gel (Merck, Kieselgel 60, F254, Art. 5715).

Column chromatographic separations were performed on silica gel (Merck, Kieselgel 60, 230-400 mesh, Art. 9385) under pressure (flash chromatography).

Synthesis:

General Procedures Used in the Below Syntheses:

General Procedure for the Palladium/Copper-Catalyzed Reaction:

To a solution of anhydrous $Et_3N$ (20 equivalents), $Pd(PPh_3)_2Cl_2$ (5% per mmol), iodo-imidazole (1 equivalent) and terminal acetylene (1.2 equivalents) was added CuI (20% per mmol) and stirring was continued for another 2 minutes under flushing with argon. The flask was then sealed and the mixture was allowed to stir at 60° C. for 8-16 hours. The resulting solution was filtered through silica gel and washed with ethyl acetate. The filtrate was concentrated under vacuum to yield the crude product, which was typically purified by flash chromatography on silica gel with ethyl acetate/hexane as the eluent.

General Procedure to Remove TIPS:

To a stirred solution of TIPS-acetylene (1 equivalent) in dry THF was cooled to −78° C. and 1 M solution of TBAF (1.1 equivalents) in THF (10 ml per mmol) was added slowly at the same temperature. After 30 minutes of stirring at the same temperature, the reaction mixture was allowed to reach 0° C. and quenched with aqueous $NH_4Cl$ and extracted with $Et_2O$ (three times), the combined organic layer was washed with brine, dried over $MgSO_4$, and concentrated in vacuum to afford the crude product. The product was thereafter purified by flash chromatography on silica gel with ethyl acetate/hexane as the eluent.

General Procedure to Remove Boc:

Alternative No. 1 using TFA in $CH_2Cl_2$— To a stirred solution of N-Boc in dry $CH_2Cl_2$ (2 ml per mmol) was added slowly TFA (1 ml) at 0° C. and stirred for 30 minutes. The solvents were thereafter evaporated under reduced pressure and then compound was dissolved in small amount of MeOH and upon addition of diethyl ether produce solid, which was collected by filtration. Alternative No. 2 using 4N HCl in ethanol—To a stirred solution of N-Boc in ethanol (5 ml per mmol) was added 4N HCl (2 ml per mmol) at 0° C. and the mixture was stirred for 14 hours at room temperature. The solvents were evaporated under reduced pressure, and then MeOH and ethyl ether was added to get a solid, which was collected by filtration.

General Procedure to Prepare Ammonium Salt from Amine:

A small amount of an amine-containing compound was stirred in MeOH with addition of concentrated HCl to obtain a solid, which was collected by filtration and washed with cold ethyl ether to afford an ammonium salt.

General Procedure for the Host-Guest Complex of CB[6] Host Hosting a Bis-Imidazole Guest Compound:

A mixture of a bis-imidazole guest and CB[6] (1:1) in $H_2O$ (100 ml per mmol) was stirred over night. The solid CB was filtered and the filtrate was concentrated under vacuum. The complex was precipitated by adding a small amount of MeOH and ether, and the solid was collected by filtration.

Polyyne Imidazolium Salts:

Polyyne are suitable guest compounds for CB[n] hosts, which can serve as ideal linear and rigid threading moieties according to some embodiments of the present invention. Since direct attachment of a nitrogen substituent to an sp-carbon of a polyyne may form an a compound that is unstable in water, a stabilized form of a carbocation could be used instead. The imidazolium cation is sufficiently stable in water for this purpose, hence the following bis-imidazole-polyyne guest compounds have been prepared (see, Scheme 4 hereinbelow).

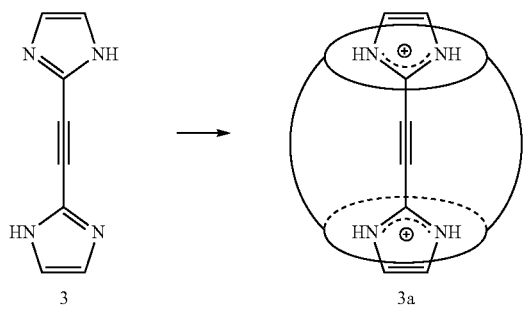

Scheme 4

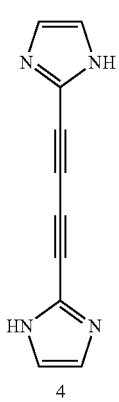

4

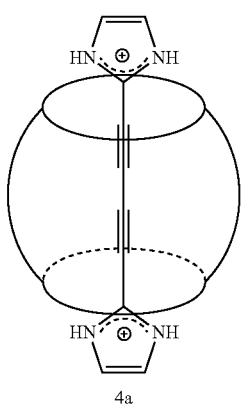

4a

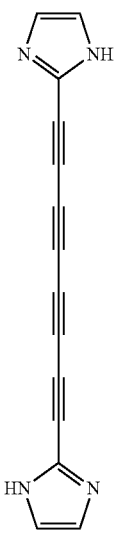

6

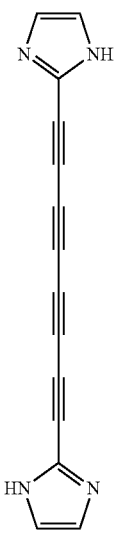

7

Aromatic Threading Moieties:

Aromatic moieties are also suitable guests for CB[n] hosts. When substituted on opposing apex positions (para-relative positions) with linking moieties, aromatic moieties can serve as ideal linear and rigid threading moieties according to some embodiments of the present invention. Aromatic threading moieties allows for longer lengths and chemical stability, as compared to polyynes. Furthermore, substituted aromatic moieties, having small and chemically suitable substituents on one or more of the other 4 free substitution positions would fill the internal space of the host and yet allow free rotation with minimal attractive or any interaction between the host and guest, and hence can be exploited for the design of optimal rotor molecules, which will allow rotation with minimal friction within the host.

Aromatic threading moieties, based on di-substituted benzene rings, represent a series of guest compounds with varying length. Exemplary di-substituted benzene rings, featuring such an aromatic threading moiety, and represented by Compounds 14-18 (see, Scheme 5 blow) have been shown by the present inventor to participate in complexation with CB[6] as confirmed by $^1$H NMR and MS.

Scheme 5

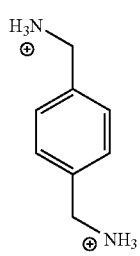

8

-continued

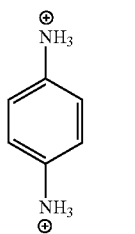
9

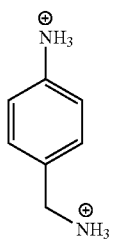
10

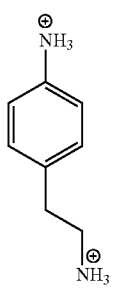
11

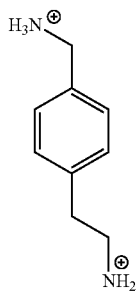
12

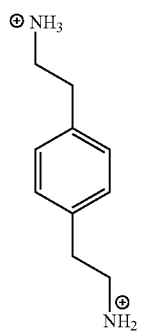
13

Scheme 6

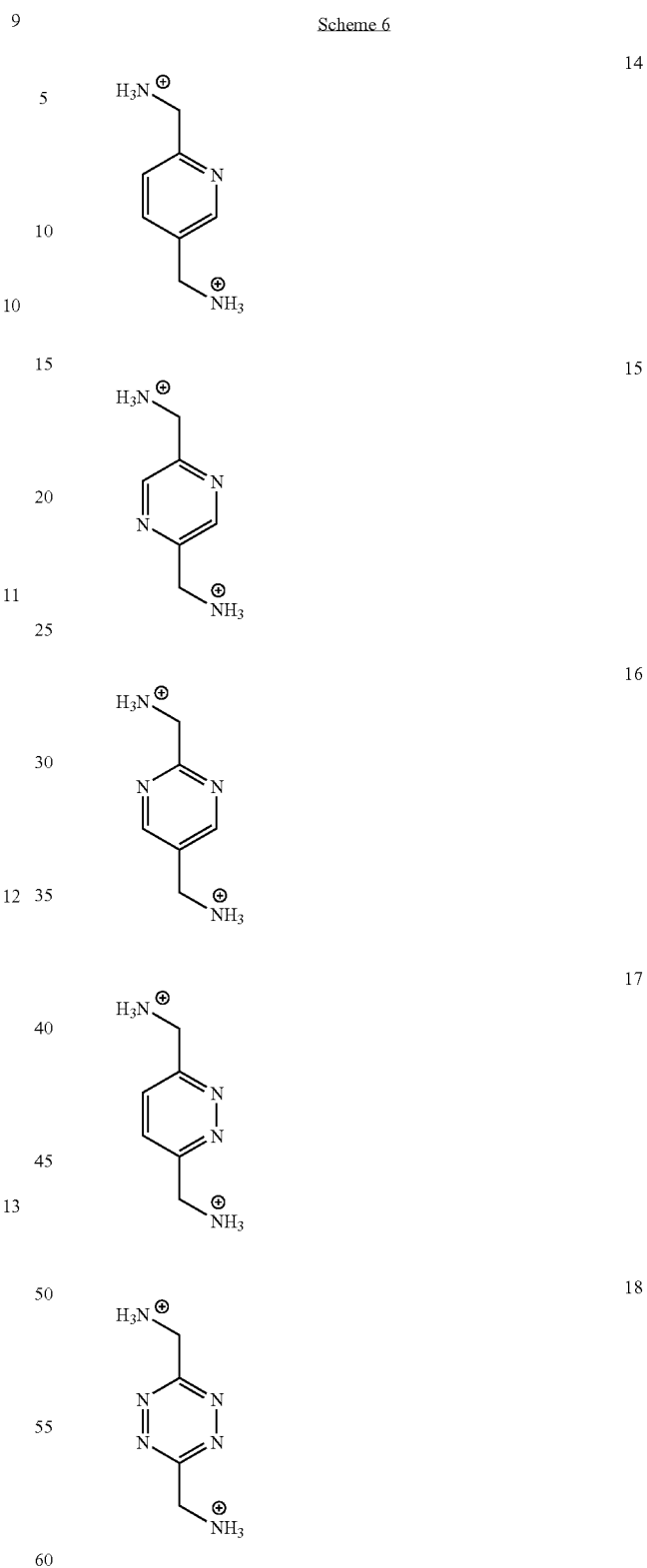

Aromatic threading moieties, based on di-substituted heteroaromatic rings containing 1-4 nitrogen atoms, constitute another series of guest compounds. Exemplary disubstituted heteroaromatic rings, featuring such a heteroaromatic threading moiety, are represented by Compounds 14-18 (see, Scheme 6 below).

Aromatic threading moieties, based on polysubstituted benzene ring having from 1 to 4 halogens substituents, constitute yet another series of guest compounds. Exemplary substituted benzene rings, featuring such a poly-halo-substituted threading moiety, are represented by Compounds 19-23 (see, Scheme 7 below).

Scheme 7

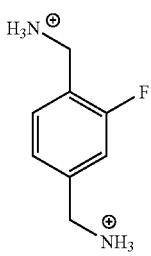
19

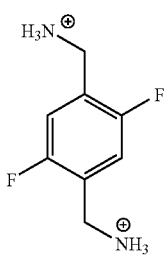
20

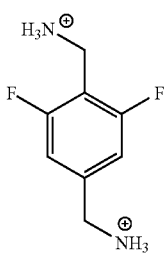
21

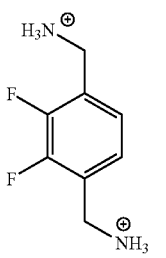
22

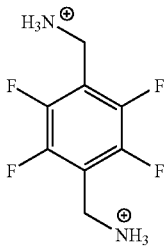
23

Host-guest interactions can be studied by isothermal titration calorimetry (ITC), 2D and temperature-dependent NMR spectroscopy, and by theoretical modeling.

According to some embodiments of the present invention, these two concepts presented hereinabove can be combined to form more aromatic threading moieties, namely the combination of heteroaryl rings and various substitutions on the ring apart from the para-disubstitutions required for the extensions out of the CB.

The major attribute which renders any aromatic ring system suitable to form a part of an aromatic threading moiety is the ability to disubstitute the aromatic core in such a way that will form an overall linear shape, namely be extendable in two opposite directions. The aromatic core of the aromatic threading moieties, according to some embodiments of the present invention, can therefore be based on other aromatic ring systems, such as for a non-limiting example, cyclobuta-1,3-diene-1,3-di-yl, pentalene-2,5-di-yl, biphenyl-4,10-di-yl and pyrene-2,7-di-yl. These aromatic systems can be carbon-based or contain one or more heteroatom, and also can be substituted or unsubstituted.

Polyyne Diammonium Salts:

An essential step towards the experimental verification of these calculated results, was the synthesis of simpler complexes of CB[6] with polyyne diammonium salts. Several exemplary 1,6-diaminohexa-2,4-diyne derivatives, namely Compounds 4'-7', presented in Scheme 8 below, were prepared in order to study their binding modes with Compound 1 (CB[6]). Such diammonium salts could serve as potential intermediates in the preparation of the desired rotary motors.

Scheme 8

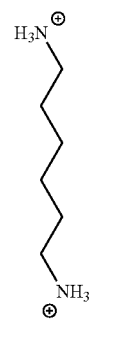
3'

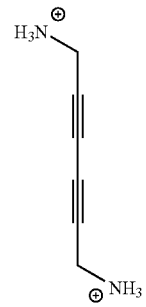
4'

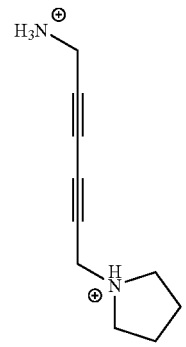
5'

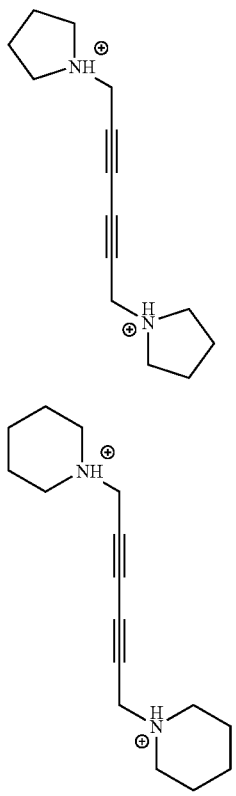

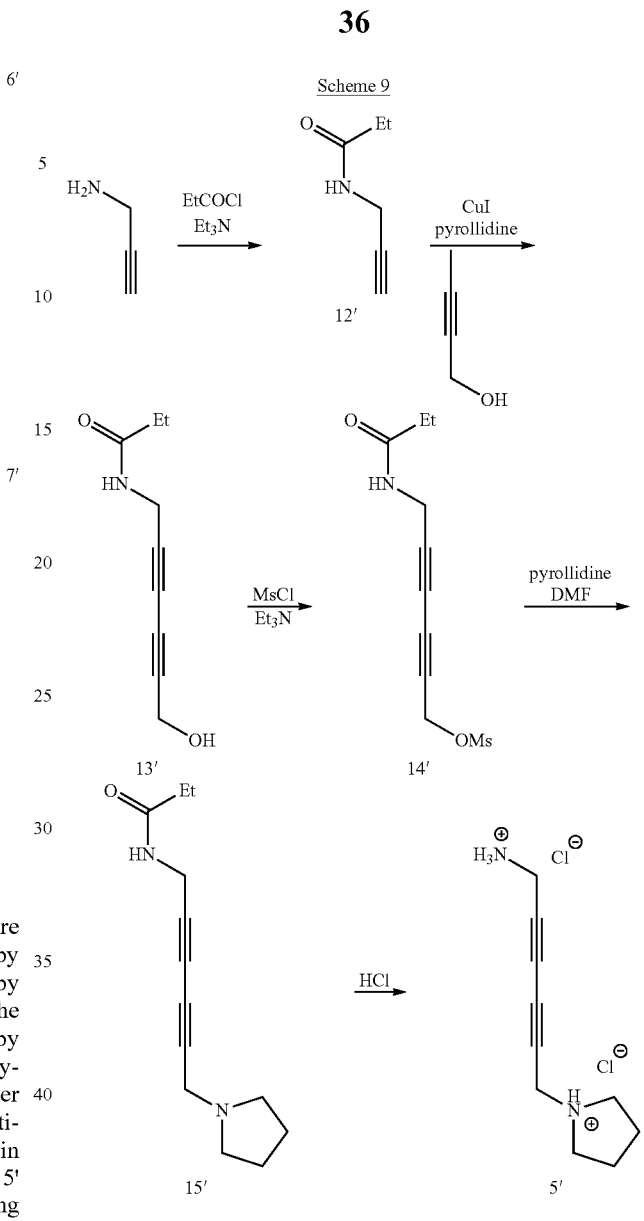

Various alkyne coupling reactions were used to prepare Compounds 4'-7'. Briefly, Compound 4' was prepared by oxidative Hay coupling of propargyl alcohol, followed by replacement of the hydroxy groups by phthalimide via the Mitsunobu reaction [78]. Compound 5' was synthesized by cross-coupling of N-propargyl proprionamide with 3-hydroxy-1-iodopropyne [79] using catalytic amounts of copper (I) iodide in pyrrolidine [80]. Subsequent Mitsunobu substitution of the alcohol by pyrrolidine [81] and deprotection in refluxing aqueous hydrochloric acid afforded Compound 5' [82]. Compounds 6' and 7' were prepared by transforming propargyl bromide to the appropriate propargyl amine, followed by a modified Hay coupling under acidic conditions [83]. All compounds were isolated and characterized in the form of their bis-hydrochloride salts.

Preparation of Hexa-2,4-diyne-1,6-diammonium dihydrochloride salt—Compound 4'

Hexa-2,4-diyne-1,6-diammonium dihydrochloride, Compound 4' was prepared using the literature procedure [84, 78]. The product was re-crystallized from methanol/diethyl ether to give Compound 4' at a 74% yield as a brown solid.

$^1$H NMR (300 MHz, DMSO-d$_6$), δ=8.74 (br s, 6H), 3.9 (d, J=6 Hz, 4H);

$^{13}$C NMR (75.44 MHz, DMSO-d$_6$), δ=73.4, 69.1, 28.6 ppm.

Preparation of 1-Ammonium-6-pyrrolidinium-hexa-2,4-diynye dihydrochloride—Compound 5'

The synthesis of Compound 5' is illustrated in Scheme 9 below.

N-Propargyl propionamide (Compound 12', see, Scheme 9) was prepared as follows. Triethyl amine (19 ml, 0.14 mol) was added to a solution of propargyl amine (5 grams, 0.09 mol) in dichloromethane (DCM, 50 ml), cooled to 0° C. Thereafter a solution of propionyl chloride (9.4 ml, 0.109 mol) in DCM (50 ml) was added dropwise and the mixture was stirred at room temperature for 2 hours. The reaction was quenched with water (20 ml), the organic layer was collected, and the aqueous layer was extracted with DCM (3 portions of 50 ml). The combined organic layer was washed with water, brine, dried over Na$_2$SO$_4$, concentrated, and finally purified by flash column chromatography (silica gel, 20% ethyl acetate in hexane) to give Compound 12' (7.4 g, 73% yield).

$^1$H NMR (400 MHz, CDCl$_3$), δ=6.27 (br s, 1H), 4.01 (dd, J=4.5, 3 Hz, 2H), 2.23 (q, J=9.5 Hz, 2H), 2.21 (t, J=6.5 Hz, 1H), 1.13 (t, J=9.5 Hz, 3H);

$^{13}$C NMR (75.44 MHz, CDCl$_3$), δ=173.6, 79.7, 71.2, 29.2, 28.9, 9.5 ppm.

N-(6-hydroxyhexa-2,4-diynyl)propionamide (Compound 13', see, Scheme 9) was prepared as follows. Copper iodide (104 mg, 0.5 mmol) was added to a stirred solution of iodopropargyl alcohol (1 gram, 5.5 mmol) and Compound 12' (11 mmol) in pyrrolidine (5 ml) at 0° C. under argon. The mixture was stirred at room temperature for 30 minutes, quenched with aqueous ammonium chloride, and thereafter extracted with diethyl ether. The organic extract was dried over $Na_2SO_4$, concentrated and purified by flash column chromatography (silica gel, 40% ethyl acetate in hexane), to give Compound 13' as a colorless solid (58% yeild).

$^1$H NMR (300 MHz, DMSO), δ=8.29 (br t, J=4.8 Hz, 1H), 5.41 (t, J=5.4 Hz, 1H), 4.15 (d, J=5.7 Hz, 2H), 3.97 (d, J=5.4 Hz, 2H), 2.1 (q, J=7.5 Hz, 2H), 0.98 (t, J=7.5 Hz, 3H);

$^{13}$C NMR (75.44 MHz, DMSO), δ=172.8, 78.6, 77.3, 67.9, 65.6, 49.3, 28.4, 28.2, 9.7 ppm.

6-(Propionamido)hexa-2,4-diynyl methanesulfonate (Compound 14', see, Scheme 9) was prepared as follows. Triethyl amine (0.5 ml, 3.6 mmol) and methanesulfonyl chloride (0.23 ml, 2.9 mmol) were added to a solution of Compound 13' (0.4 grams, 2.4 mmol) in DCM (5 ml) at 0° C., the mixture was stirred at room temperature for 1.5 hours, quenched with water (10 ml), the organic layer was separated, and the aqueous layer was extracted with DCM (2 portions of 20 ml). The combined organic layer was washed with aqueous $NaHCO_3$ solution, water, brine, dried over $Na_2SO_4$, concentrated, and purified by flash column chromatography (silica gel, 50% ethyl acetate in hexane) to give Compound 14' (0.51 grams, 86% yield).

$^1$H NMR (400 MHz, $CDCl_3$), δ=6.25 (br s, 1H), 4.97 (s, 2H), 4.21 (m, 2H), 3.19 (s, 3H), 2.30 (q, J=6.5 Hz, 2H), 1.21 (t, J=6.5 Hz, 3H);

$^{13}$C NMR (75.44 MHz, $CDCl_3$), δ=174.0, 78.7, 73.9, 69.8, 66.6, 58.1, 39.4, 29.9, 29.7, 9.9 ppm.

N-(6-(pyrrolidin-1-yl)hexa-2,4-diynyl)propionamide (Compound 15', see, Scheme 9) was prepared as follows. Pyrrolidine (0.14 ml, 1.65 mmol) was added to a stirred solution of Compound 14' (0.2 grams, 0.82 mmol) in DMF (2 ml), the reaction mixture was stirred at room temperature until completion (monitored by TLC), then quenched by water (8 ml), and extracted with ether (3 portions of 30 ml). The ether layer was washed with brine, dried over $Na_2SO_4$, concentrated, and purified by flash column chromatography (silica gel, 40% ethyl acetate in hexane) to give Compound 14' (0.098 gram, 55% yield).

$^1$H NMR (400 MHz, $CDCl_3$), δ=6.70 (br s, 1H), 4.03 (d, J=4.5 Hz, 2H), 3.42 (s, 2H), 2.54 (m, 4H), 2.16 (q, J=6.5 Hz, 2H), 1.73 (m, 4H), 1.08 (t, J=6.5 Hz, 3H);

$^{13}$C NMR (75.44 MHz, $CDCl_3$), δ=173.6, 74.7, 73.5, 68.5, 67.2, 52.2, 43.2, 29.4, 29.0, 23.6, 9.5 ppm.

N-6-pyrrolidinium-hexa-2,4-diynyl ammonium dichloride (Compound 5', see, Scheme 9) was prepared as follows. Propionamide Compound 15' (0.098 grams, 0.45 mmol) was mixed with aqueous HCl (8 M, 4 ml), the solution was refluxed overnight, allowed to cool to room temperature, and extracted with DCM (2 portions of 10 ml). Thereafter the aqueous part was separated and the water was evaporated under reduced pressure. The residue was dissolved in MeOH and precipitated out with ether. Finally, the precipitate was filtered and dried to give Compound 5' (0.80 grams, 76% yield).

$^1$H NMR (400 MHz, $D_2O$), δ=4.23 (s, 2H), 3.96 (s, 2H), 3.67 (m, 2H), 3.22 (m, 2H), 2.15 (m, 2H), 2.01 (m, 2H);

$^{13}$C NMR (75.44 MHz, $D_2O$) −δ: =73.3, 73.1, 71.2, 70.4, 55.4, 45.3, 31.1, 24.6 ppm.

Preparation of 1,6-Dipyrrolidinium-2,4-hexadiyne dichloride—Compound 6'

1,6-Dipyrrolidino-2,4-hexadiyne was dissolved in ethanol, and concentrated HCl was added to reach pH 2. The product was re-crystallized from ethanol/diethyl ether (0.6 grams, 55% yield).

$^1$H NMR (300 MHz, $D_2O$), δ=1.74 (t, 8H), 2.53 (t, 8H), 3.43 (t, 4H);

$^{13}$C NMR (75.44 MHz, $D_2O$), δ=70.69, 69.00, 53.40, 43.20, 22.55 ppm;

MS (CI) m/z=217 (M+1).

Preparation of 1,6-Dipiperidinium-2,4-hexadiyne dichloride—Compound 7'

1,6-Dipiperidino-2,4-hexadiyne was dissolved in ethanol and was treated with concentrated hydrochloric acid until the pH level of the solution reached pH 2. Thereafter the product was re-crystallized from ethanol/diethyl ether to give 0.7 grams (44% yield).

$^1$H NMR (300M Hz, $D_2O$), δ=1.46 (m, 4H), 1.70 (m, 8H), 1.94 (m, 4H), 3.05 (t, 4H), 3.59 (d, 4H), 4.10 (s, 4H);

$^{13}$C NMR spectra (75.44 MHz, $D_2O$), δ=71.97, 68.38, 52.54, 45.76, 22.39, 20.22 ppm;

MS (CI) m/z=245.2 (M+1).

Insertion complex of Compound 1 (CB[6]) with Compound 4' (Complex 4)

An aqueous solution of Compound 1 was added to a solution of diammonium salt, Compound 4' in water. The mixture was stirred overnight at room temperature, and thereafter filtered, and the filtrate was concentrated to give the crude product, which was dissolved in a minimum amount of water. Methanol was slowly added and the resulting precipitate was filtered and washed with methanol and dried to afford Complex 4'.

Complex 4' was crystallized and the crystal structure thereof was elucidate using X-ray crystallography. Apparently, Compound 1, which was used for this preparation, was contaminated with sulphuric acid, a fact that resulted in incorporating hydrosulfate anions within the crystal structure of Complex 4'. The results of the X-ray crystallography experiment are presented hereinbelow.

$^1$H NMR (400 MHz, $D_2O$), δ=5.74 (m, 12H), 5.57 & 5.55 (2 s, 12H), 4.28 (m, 12H), 3.33 (s, 4H).

Insertion Complex of Compound 1 (CB[6]) with Compound 5' (Complex 5)

Complex 5' was prepared according to the procedure described above for the preparation of Complex 4', using Compound 1 and Compound 5'.

Complex 5' was crystallized and the crystal structure thereof was elucidate using X-ray crystallography, and the results of the experiment are presented hereinbelow.

$^1$H NMR (400 MHz, $D_2O$), δ=7.37 (br s, 1H), 7.24 (br s, 3H), 5.57 (2d, J=13.5 Hz, 12H), 5.48 (s, 12H), 4.34 (2d, J=13 Hz, 12H), 4.34 (m, 2H), 4.18 (m, 2H), 3.83 (m, 2H), 3.09 (m, 2H), 2.02 (m, 4H).

Insertion Complex of Compound 1 (CB[6]) with Compound 7' (Complex 7)

An aqueous solution of Compound 1 was added to a solution of 1,6-dipiperidinium-2,4-hexadiyne dichloride, Compound 7', in water, the mixture was stirred for 15 minutes with gentle heating using a heat gun, filtered with a micro-filter, and thereafter acetone was added until solid precipitation occurred. The mixture was left overnight at room temperature and thereafter the solid precipitation was collected by applying centrifugation, and the solid was washed with acetone. This procedure was repeated several to afford pure Complex 7'.

Complex 7' was crystallized and the crystal structure thereof was elucidate using X-ray crystallography, and the results of the experiment are presented hereinbelow.

$^1$H NMR (300 MHz, D$_2$O), δ=5.68 (m, 12H), 5.59 (s, 12H), 4.39 (m, 12H), 3.78 (s, 4H) 2.97 (m, 12H), 1.72 (m, 8H), 1.52 (m, 4H);

$^{13}$C NMR (75.44 MHz, D$_2$O), δ=156.2, 71.5 68.5, 52.2, 49.5, 46.1, 23.2, 21.1 ppm;

MS (MALDI-TOF) m/z=1242 (M).

Insertion Complex of Compound 1 (CB[6]) with Compound 6' (Complex 6')

Complex 6' was prepared according to the procedure described above for the preparation of Complex 7', using Compound 1 and Compound 6'.

$^1$H NMR (300 MHz, D$_2$O), δ=5.53 (d, 12H, J=15.6), 5.32 (s, 12H), 4.07 (d, J=15.6, 12H), 4.08 (s, 4H) 3.11 (m, 4H), 1.94 (br, 8H), 1.8 (br, 4H);

MS (MALDI-TOF) m/z=1214 (M).

Construction of Rotaxanes Based on CB[6] and Uncharged Guests—General Procedure The attachment of bulky and uncharged stopper moieties on both ends of an uncharged threading moiety can be based, according to some embodiments of the present invention, on the azide-alkyne Huisgen cycloaddition, also known as 1,3-dipolar cycloaddition, which is a reaction between an azide and a terminal or internal alkyne which typically affords a 1,2,3-triazole [85].

The general synthetic strategy to achieve this goal is based on three major steps: a) synthesis of a guest molecule featuring a diammonium threading moiety that has strong binding interaction to the CB host, b) attachment of two bulky stopper moieties to the ends of the threading moiety, and c) elimination of the charge-based binding interaction between the guest and the host molecules by removing the charge form the ammonium groups, conversion of the amine groups to amine oxide groups, or even elimination of the nitrogen groups from the molecule.

There are several strategies which can be applied to achieve the attachment of bulky and uncharged stopper moieties at the ends of a threading moiety once it is inserted in the CB host. An exemplary approach, according to some embodiments of the present invention, uses branched guest molecules where the functional extension branches at the α position. Scheme 10 below presents an illustration of this approach, showing an exemplary guest molecule having 2-azido-ethan-ammonium (ammonium azide) moieties at each end of the threading moiety, inserted in a CB[6] host, and reacted with 2 equivalents of 10-ethynylanthracene to form two 4-(anthracen-9-yl)-1H-1,2,3-triazole moieties, which subsequently relinquish ammonia and molecular hydrogen to yield two uncharged stopper moieties based on 4-(anthracen-9-yl)-1-((E)-vinyl)-1H-1,2,3-triazole moieties.

Scheme 10

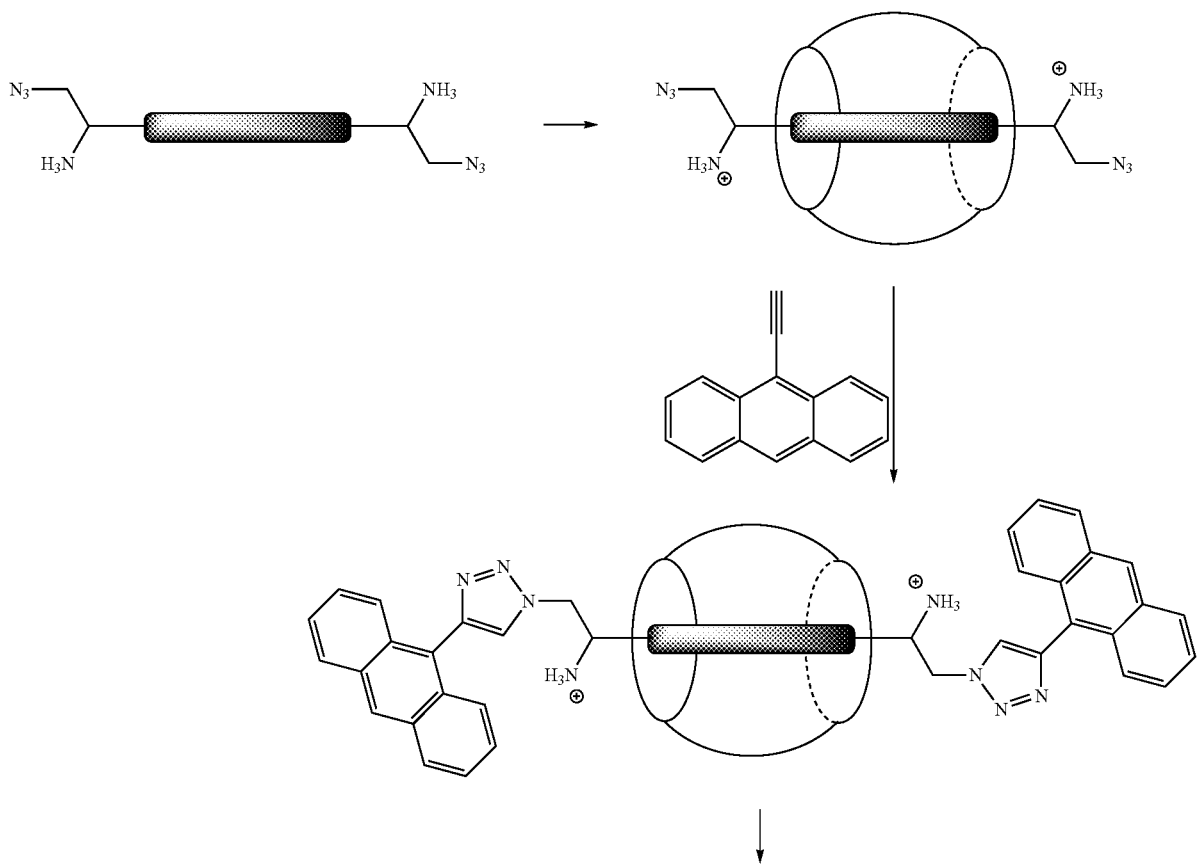

-continued

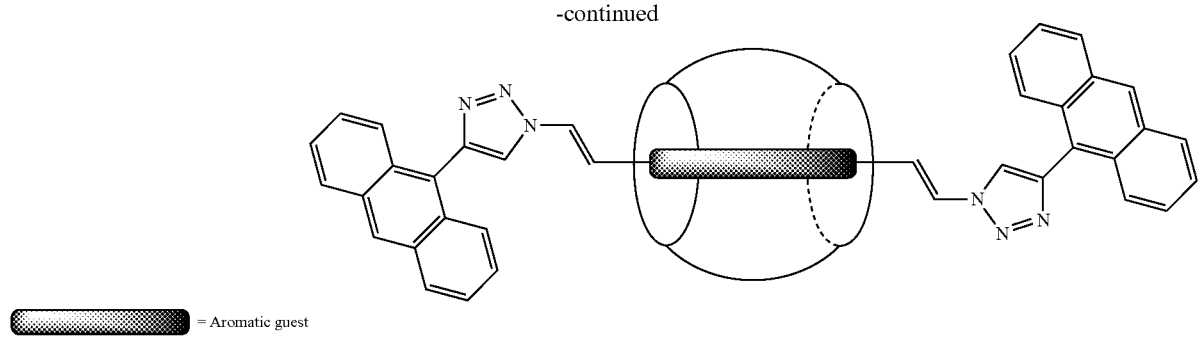

■ = Aromatic guest

The branched ammonium azide are prepared according to Scheme 11 from 1,4-dialdehyde benzene, which is converted to the corresponding bis-acid via the corresponding bis-imidazolidine with NaCN, $(NH_4)_2CO_2$ and NaOH, and reduced to afford the branch amino-alcohol, which thereafter converted to diammonium azide.

Scheme 11

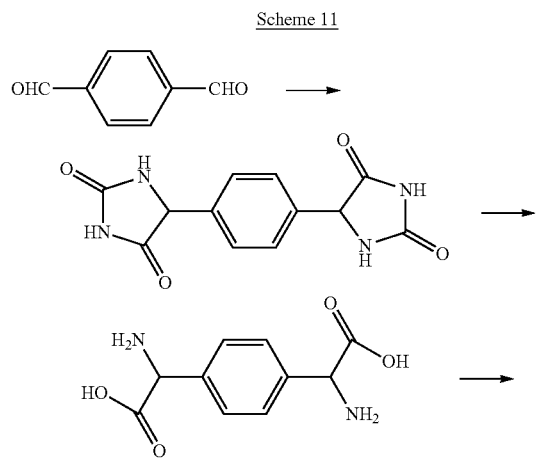

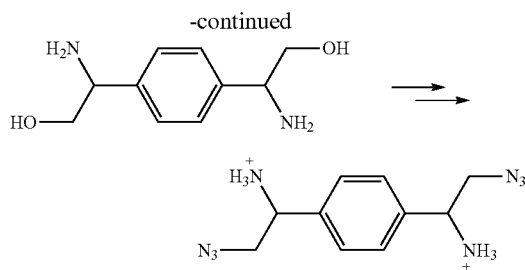

Another exemplary approach to achieve the attachment of bulky yet uncharged stopper moieties at the ends of a threading moiety, according to some embodiments of the present invention, uses elongated guest molecules where the functional extension is bound directly to the nitrogen atom at the ends of the threading moiety. Scheme 12 below is an illustration of this approach, showing an exemplary guest molecule having two N-linked-ethanammonium-2-azido groups at each end of the threading moiety reacted with 1-ethynyl-adamantane while inserted in a CB[6] host to afford two N-(2-(4-adamantyl-1H-1,2,3-triazol-1-yl)ethyl)-ammonium moieties which thereafter yield the uncharged N-oxide thereof.

Scheme 12

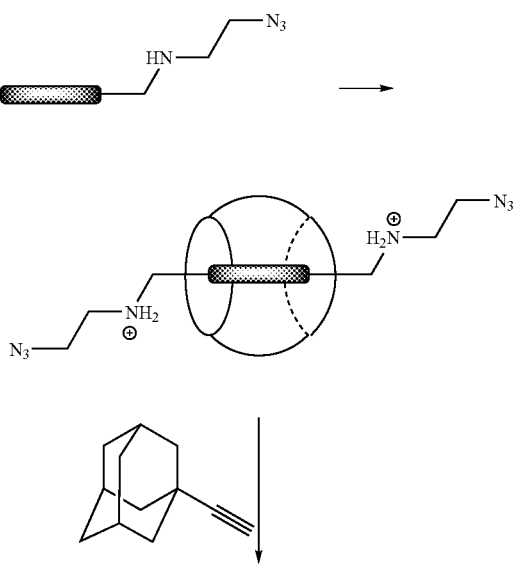

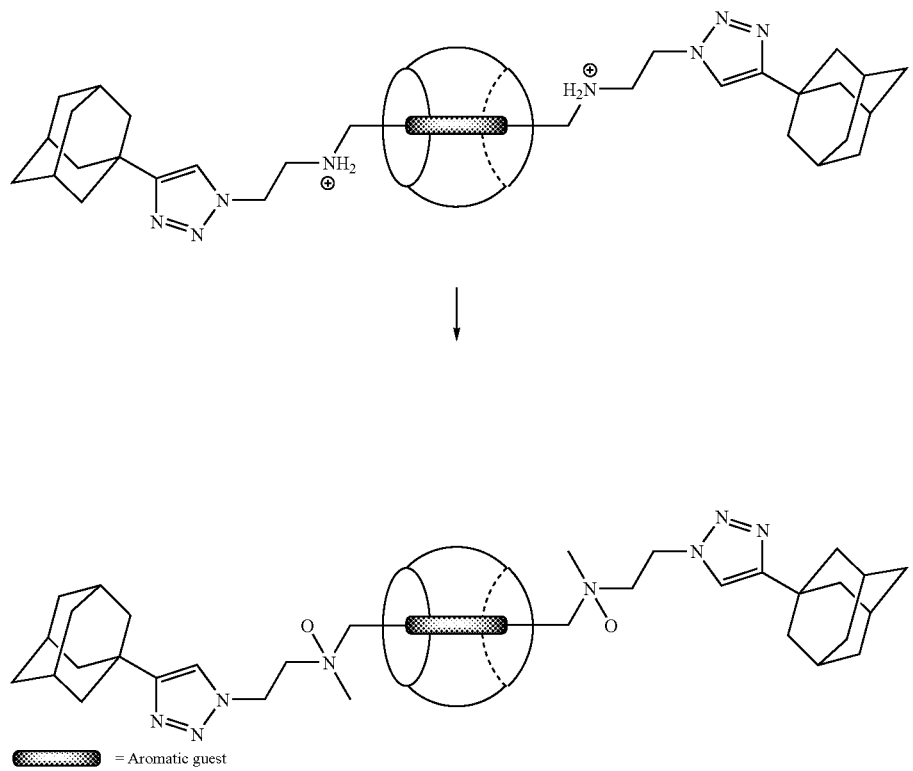

= Aromatic guest

Two exemplary host-guest complexes according to some embodiments of the present invention have been prepared as presented in Scheme 13.

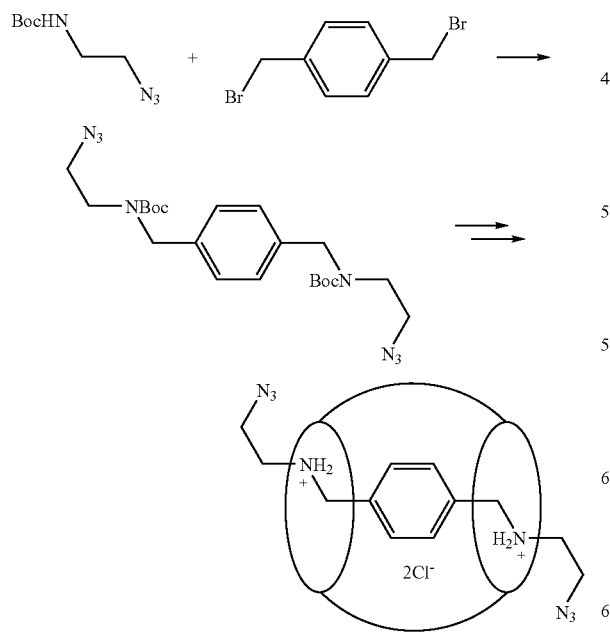

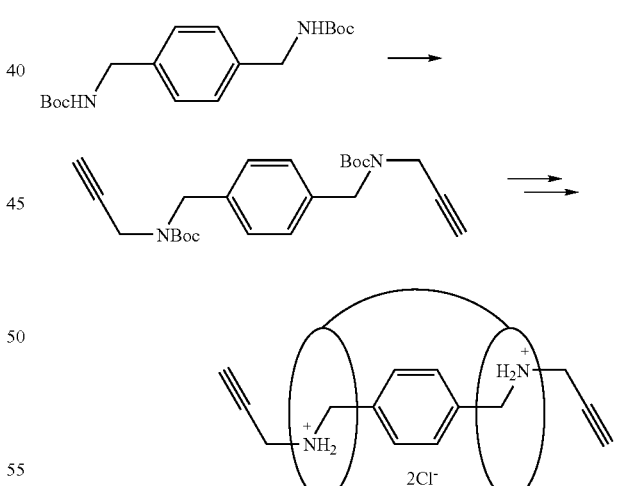

Preparation of Rotors for Frictionless Molecular Motors—General Procedure

The preparation of an exemplary frictionless molecular motor according to some embodiments of the present invention is exemplified in Scheme 14 below.

Scheme 14
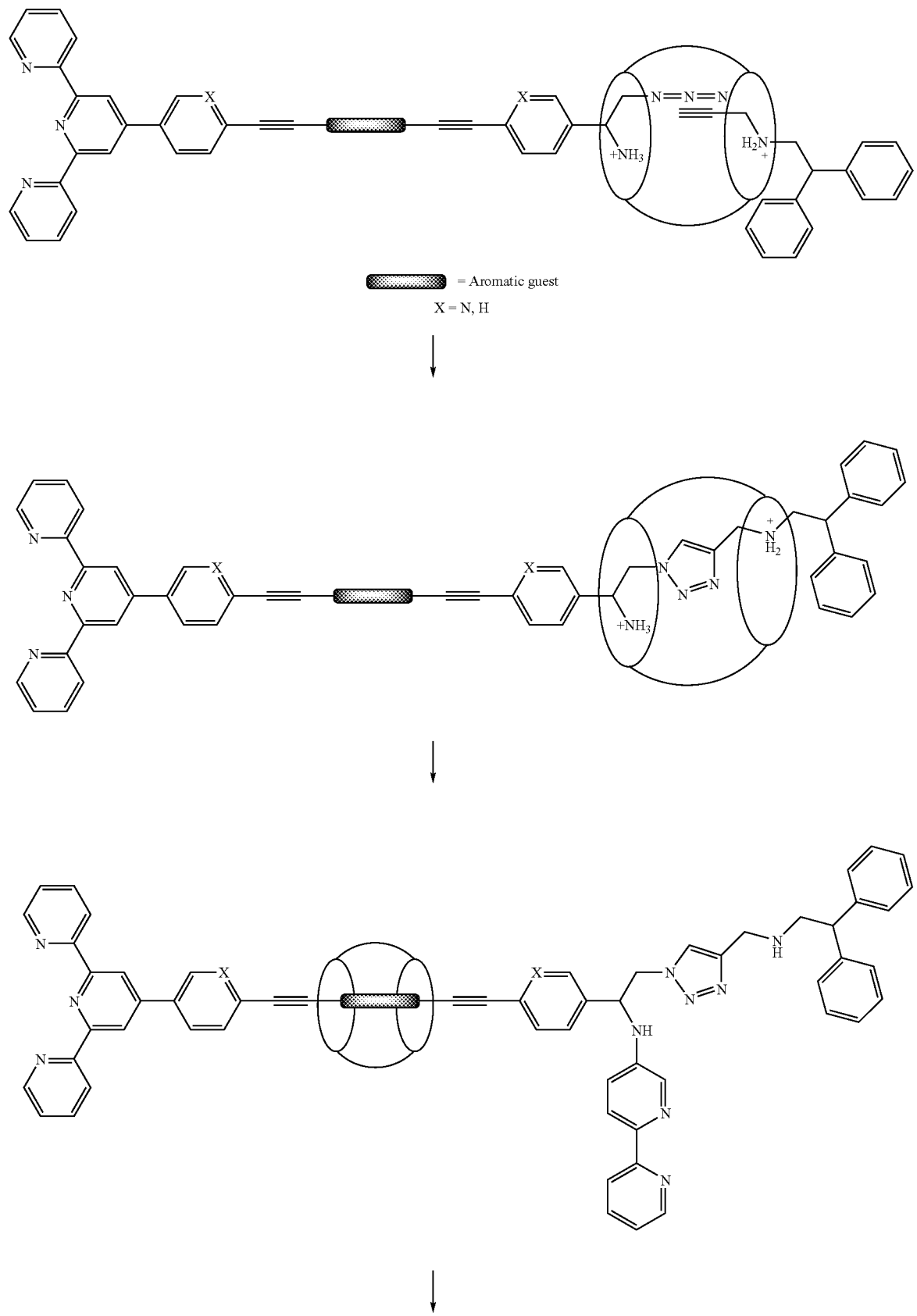
= Aromatic guest
X = N, H

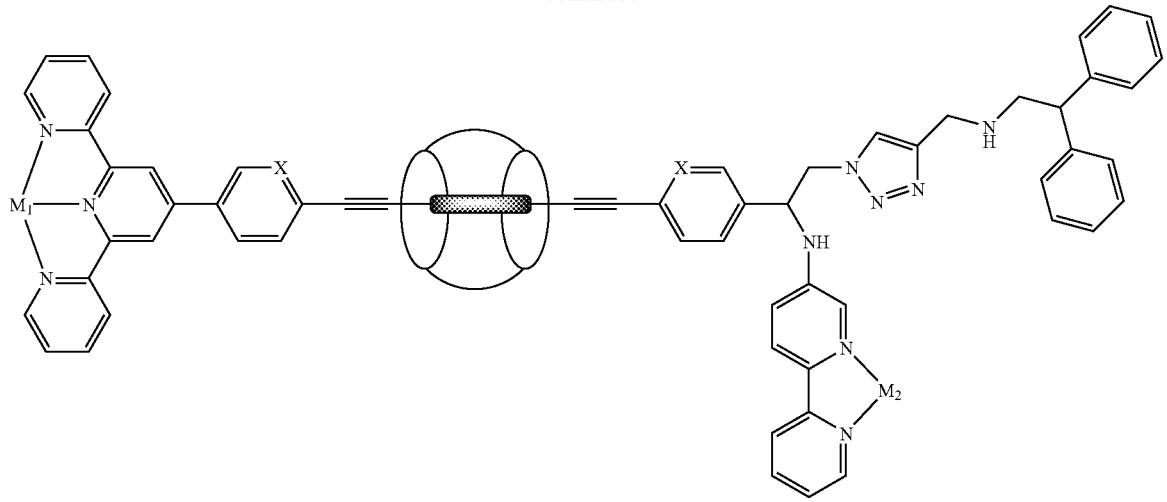

As can be seen in Scheme 14, a rigid and linear molecular rotor is exemplified by a molecule comprising an aromatic threading moiety, elongated on both sides with ethynyl groups is fitted on one side with a bulky ter-pyridine stopper moiety (or any alternative suitable bulky aromatic stopper moiety) and with a ammonium-azide group on the other side. The azide is reacted by a 1,3-dipolar cycloaddition reaction with the alkyne group of an alkyne-ammonium-containing molecule which further comprises a bulky group, which is represented by the exemplary N-(2,2-diphenylethyl)prop-2-yn-1-ammonium in Scheme 14.

According to this example, but without being bound by any particular theory, a ternary complex is first formed between the CB[6], the azide-containing molecule and the alkyne-containing molecule via the ammonium groups of the azide and the alkyne and the carbonyl oxygen-lined portals of the CB[6]. It is suggested herein that the 1,3-dipolar cycloaddition would occur inside the core of CB[6] to form a 1,2,3-triazole. At this stage the CB[6] is threaded and interlocked by the rotor molecule, which have bulky stopper moieties on both sides, and will remain interlocked at a wide pH range or the oxidation of amine group. Yet the CB[6] is free to move along the molecular from one side to the other.

At a high pH at which the ammonium groups are deprotonated and no longer charged, the CB is free to move to the aromatic threading moiety part of the rod. This can be followed by a reaction that will permanently lock the cavitand at that position. Such a reaction can be effected by, for example, an aromatic or alkyl iodide which can react with the amine, as shown in Scheme 14, and add, for example, a 2-(pyridin-2-yl)pyridine moiety on the amine.

As presented in Scheme 14, the rotor can be fitted with different components that can be affected by external source(s) of energy to drive the molecular motor, according to some embodiments of the present invention. For example, two different metal ions can be coordinated to each end of the molecular rotor, or stopper moieties, according to some embodiments of the present invention. Two metal ions, such as rhodium and ruthenium, allow photo-induced electron transfer from one metal to the other through the electron conducting π-electron conjugated chain connecting therebetween. It is suggested herein that such an electron transfer could induce magnetic field around the CB host and this field could induce unidirectional rotation.

The exemplary branch amino-azide, presented in Scheme 14 hereinabove, can be synthesized for example, from 6-bromo-3-pyridine carboxyldehyde, as illustrated in Scheme 15. Compound III has been prepared according to Scheme 15. Compound II in Scheme 15 is prepared from Compound I following the procedure presented in Scheme 11. A Pd$^{II}$ cross-coupling reaction of Compound II with Compound III produces the hydroxy branch amine, Compound IV, where the hydroxy group is converted to azide using mesylate.

Scheme 15

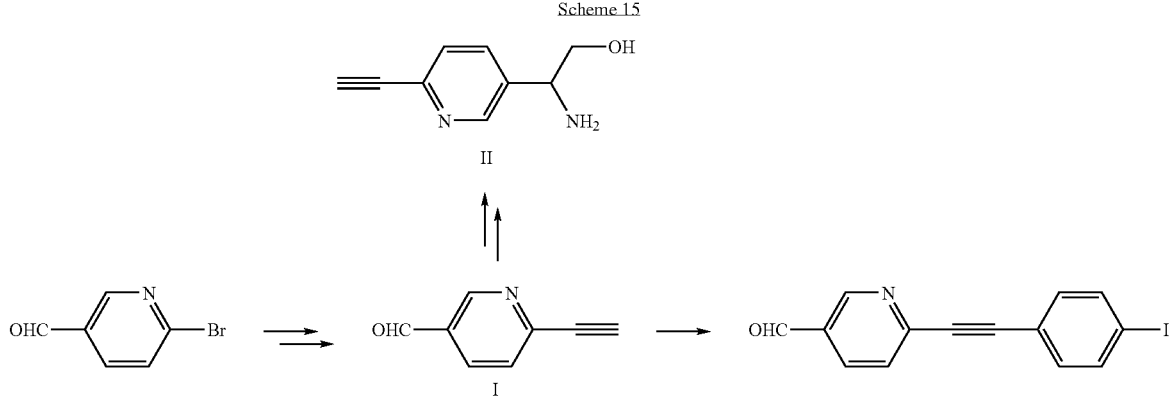

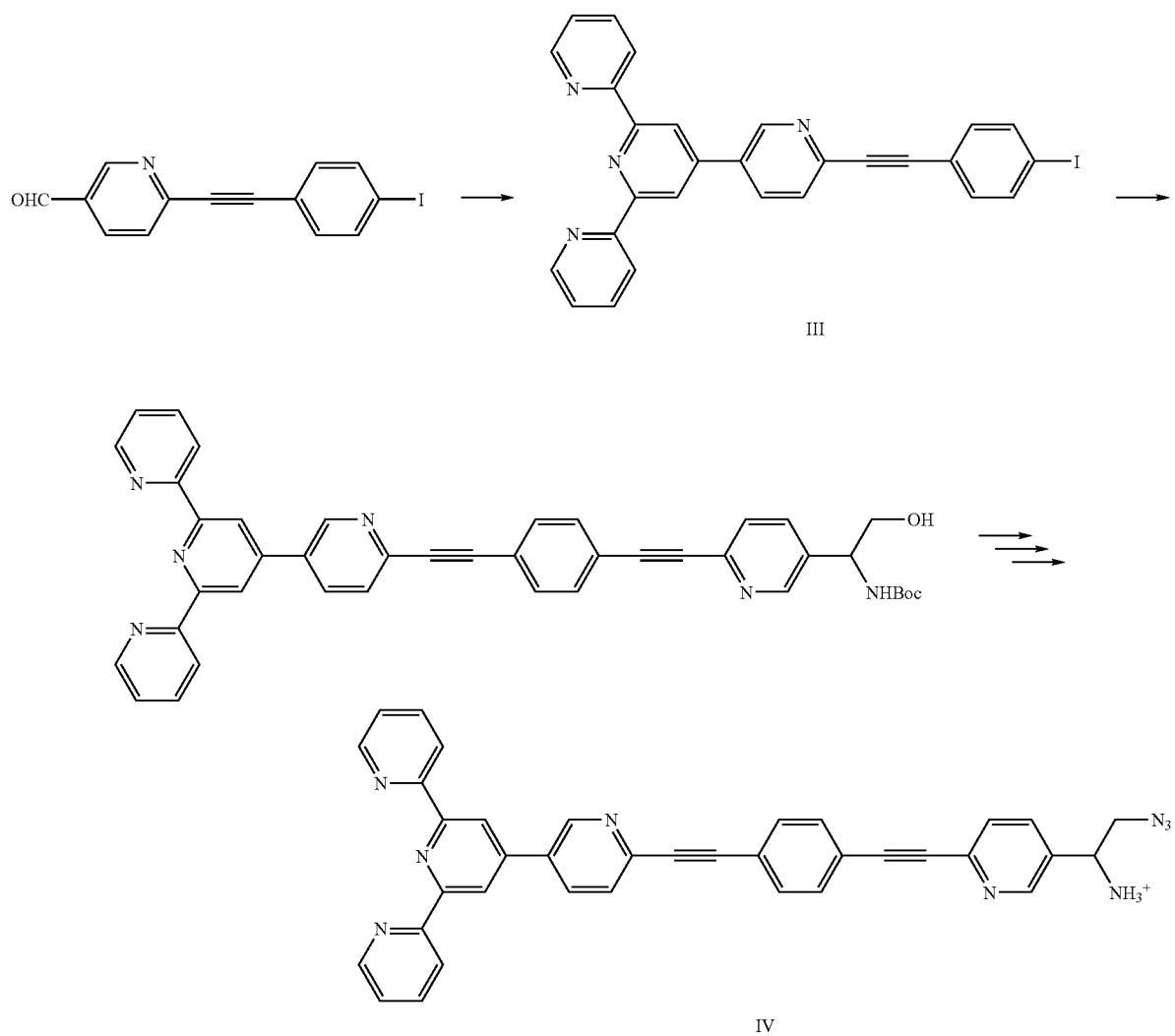

III

IV

Preparation of Switching Devices (Chemical Logic Gates)—General Procedure

The concept of a CB [n] molecule shuttling along a guest molecule as a result of a change in pH was reported in by Sindelar et al. [73, 75] who reported a CB[6 or 7] as a "wheel" component in a pseudorotaxanes, which shuttles between the two axle termini at low pH, whereas the shuttling motion stops at higher pH as the CB is bound to the center of the axle. This configuration can be used as a molecular switch which responds, for example, to a pH change.

The following guest molecules, Compounds 24-26, presented in Scheme 16 below, are used in the preparation of molecular rotors for molecular switching devices, according to some embodiments of the present invention.

Scheme 16

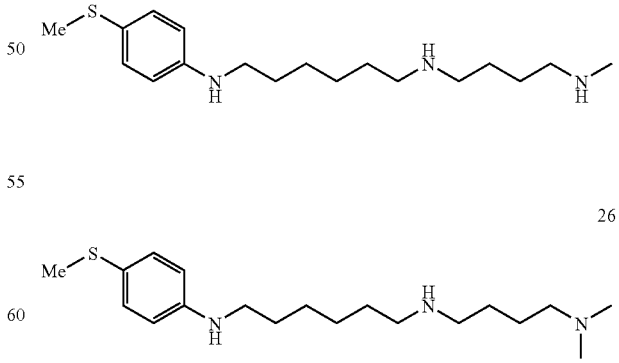

Each of these guest molecules can be accommodated in two different modes within the CB host, Mode A and Mode B, as illustrated in Scheme 17 below, Scheme 17

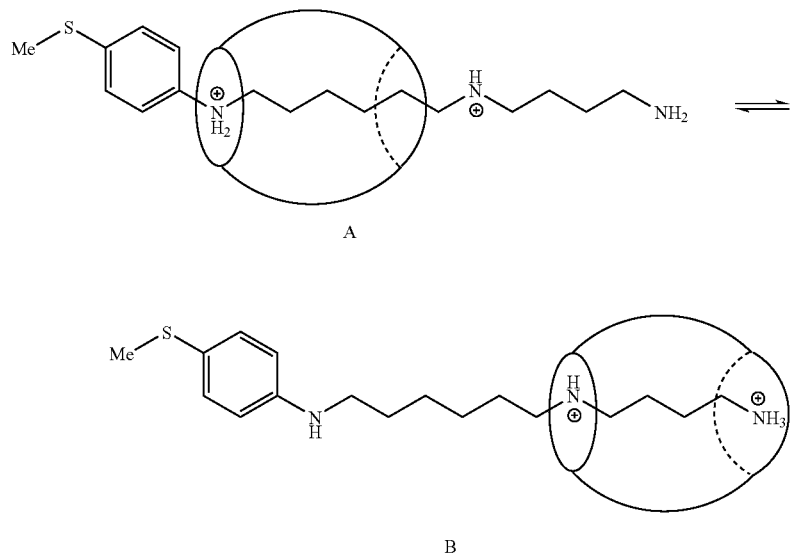

As can be seen Scheme 17, while Mode A is preferred under acidic conditions, Mode B would prevail under different conditions: a) higher pH, b) presence of thiophilic metal cations, such as Hg, Cd, Ag, and c) under oxidizing conditions where the sulfide is converted to the corresponding sulfoxide, and the binding modes can be determined by NMR and/or by UV/fluorescence spectroscopy. For each of the guest molecules, Compounds 24-26, the triple-value pKa curve will serve to construct and characterize the resulting logic gates.

Compound 24 was prepared as shown in Scheme 18 below. Compounds 25 and 26 are prepared following a similar strategy by changing the amine group.

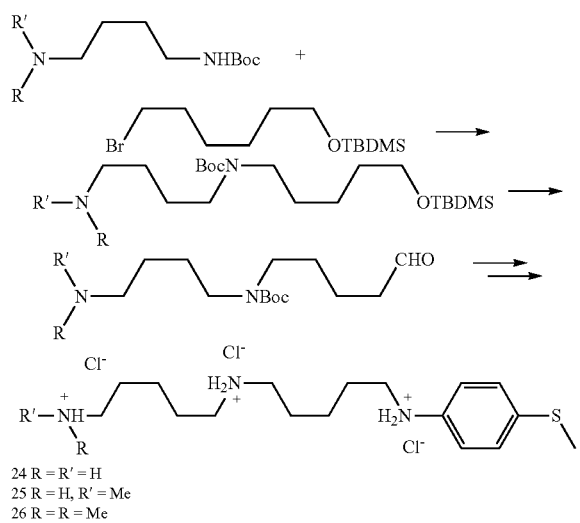

24 R = R' = H
25 R = H, R' = Me
26 R = R = Me

Preparation of Bis-Imidazole Guest Molecules Having Polyyne Threading Moieties of Various Lengths The entire synthesis of several exemplary bis-imidazole polyyne molecules and their subsequent insertion in a CB[6] molecule to afford the corresponding insertion complex, according to some embodiments of the present invention, is illustrated in Scheme 19 below.

The preparation of both 2-(2-(1H-imidazol-2-yl)ethynyl)-1H-imidazole (Compound 3) and 2-(4-(1H-imidazol-2-yl) buta-1,3-diynyl)-1H-imidazole (Compound 4) started from a commercial available imidazole, Compound 27, which was protected in the form of N-Ttr imidazole, Compound 28, by using triphenylmethylchloride. Thereafter, iodination of Compound 28 with n-BuLi and $I_2$ yielded Compound 29 in 60% yield in a two steps reaction. The protecting group was removed by using 5% AcOH in MeOH and afforded Compound 30. The resulting free amine was protected with $(Boc)_2O$ to obtain Compound 31. Cross-coupling of Compound 31 in the presence of CuI and $Et_3N$ with TIPS-acetylene using the Sonogashira reaction was performed to produce Compound 32 and the subsequent removal of the TIPS group yielded Compound 33. Compound 34 was obtained from Compound 33 and Compound 31 by $Pd^{II}$-catalyzed cross-coupling reaction. Compound 34 was then subjected to oxidative coupling to yield Compound 35.

The Boc groups were removed using TFA in $CH_2Cl_2$ to produce Compound 3 and Compound 4, which on mixing with CB[6] (Compound 1) afforded the corresponding cucurbituril insertion Complex 3a and Complex 4a.

The various synthetic steps presented in Scheme 19 were as follows: a) tri-phenylmethylchloride, $Et_3N$, DMF, room temperature, yield 91%; b) n-BuLi, $I_2$, THF, 0° C.; c) 5% acetic acid in MeOH, reflux, yield 85%; d) $(Boc)_2O$, $Et_3N$, DMF/MeCN, room temperature, yield 90%; e) TIPS-acetylene, $(PPh_3) PdCl_2$, CuI, $Et_3N$, 40° C.; f) TBAF, THF, −78° C.; g) 1-Boc-2-iodoimidazole, $(PPh_3) PdCl_2$, CuI, $Et_3N$, 40° C., 14 hours, yield 83%, h) TFA, $CH_2Cl_2$, 0° C. to room temperature; i) CB[6], $D_2O$/TFA, room temperature.

Scheme 19
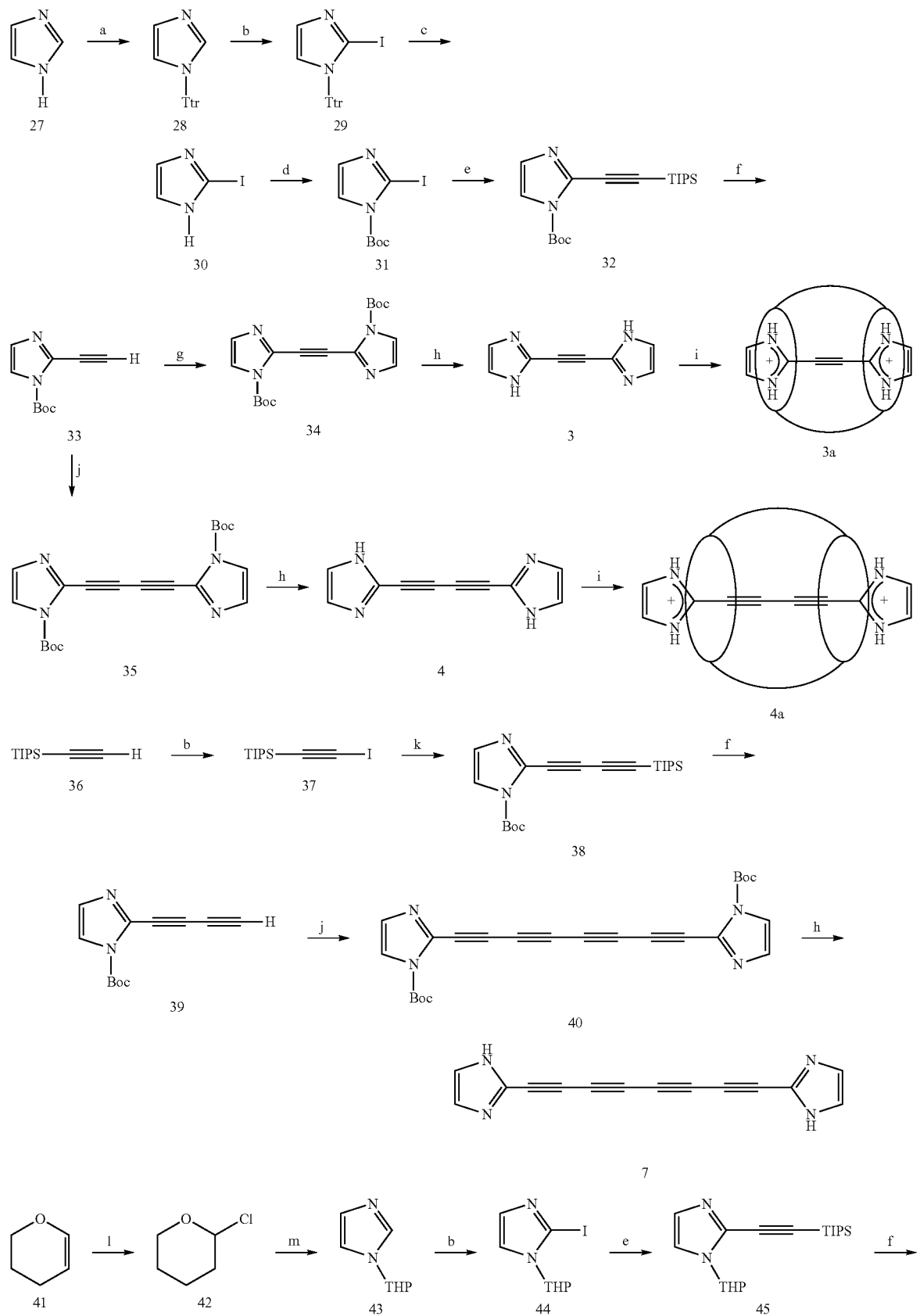

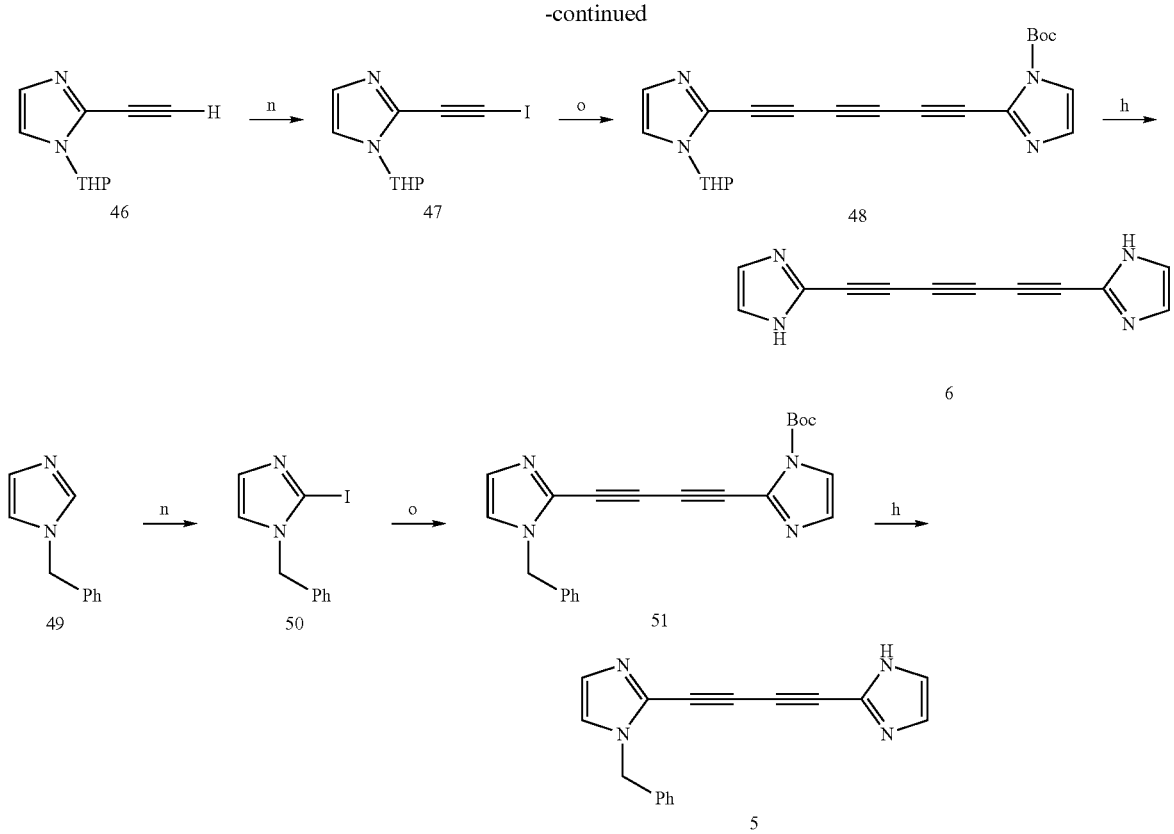

1-trityl-midazol (Compound 28, Scheme 19) was prepared by adding Et₃N (5.1 ml, 36.7 mmol) at 0° C. to a stirred solution of the imidazole Compound 27 (2.5 grams, 36.7 mmol) dissolved in 75 ml DMF. After 30 minutes of stirring, trityl-chloride (10.3 grams, 36.7 mmol) dissolved in DMF (45 ml) was added slowly to the reaction mixture, and the reaction mixture was allowed to reach room temperature while stirred continuously for over night. Thereafter the reaction mixture was quenched with cold water (1 L) to precipitate a solid, which was collected by filtration and recrystallized from hexane/DCM to afford Compound 28 as a white solid (91% yield).

$^{1}$H NMR (500 MHz, CDCl$_{3}$) −δ: 7.47 (s, 1H), 7.33-7.30 (m, 9H), 7.16-7.12 (m, 6H), 7.07 (s, 1H), 6.83 (s, 1H).

1-trityl-2-iodoimidazol (Compound 29, Scheme 19) was prepared by adding nBuLi (21.7 ml, 1.6 M in hexane, 34.8 mmol) to a stirred solution of Compound 28 (9 grams, 29 mmol, 1-trityl-imidazole, see, Scheme 19) dissolved in dry THF (200 ml) at 0° C. under argon atmosphere. The reaction mixture, which gradually turned red, was stirred at room temperature for 1.5 hours, thereafter cooled to 0° C., and iodine (7.4 grams, 29 mmol) dissolved in THF (25 ml) was added dropwise. The reaction mixture was allowed to reach room temperature and stirred for 1 hours, and thereafter quenched with aqueous NH$_{4}$Cl and concentrated. The concentrated residue was dissolved in ethyl acetate, washed with 1% HCl, sodium thiosulfate, and brine, dried over NaSO$_{4}$ and concentrated to afford a crude product, which was purified by flash chromatography on silica gel using ethyl acetate:hexane (3:7) as the eluent to afford Compound 29 as a yellowish-white solid (80% yield).

$^{1}$H NMR (500 MHz, CDCl$_{3}$) −δ: 7.35-7.33 (m, 9H), 7.19-7.16 (m, 6H), 6.99 (d, J=1.5 Hz, 1H), 6.82 (d, J=1.5 Hz, 1H);

$^{13}$C NMR (125 MHz, CDCl$_{3}$) −δ: 141.6, 130.7, 130.2, 128, 127.8, 125.8, 90.3.

2-Iodoimidazole (Compound 30, Scheme 19) was prepared from Compound 29 (1.5 g, 3.4 mmol, 1-trityl-2-iodoimidazole, see, Scheme 19) which was refluxed in 25 ml of 5% acetic acid in methanol for 45 minutes. After evaporation of solvent, water was added to the residue and placed in an ice bath. The solution was filtered and the filtrate was evaporated under reduced pressure to afford Compound 30 as white solid (85% yield).

$^{1}$H NMR (500 MHz, D$_{2}$O) −δ: 6.91 (s, 2H).

1-Boc-2-iodoimidazole (Compound 31, Scheme 19) was prepared by adding Et$_{3}$N (1.7 ml, 12.4 mmol) to a stirred solution of Compound 30 (2-iodoimidazole) (2 grams, 10.3 mmol) in DMF (50 ml) and MeCN (50 ml) at room temperature, and the reaction mixture was stirred for 30 minutes. Thereafter a solution of di-tert-butyl-dicarbonate in DMF (10 ml) was added to reaction mixture, and the reaction was allowed to continue while monitored by TLC. The reaction mixture was thereafter quenched with NaHCO$_{3}$, the solvent was removed under reduced pressure, extracted with EtOAc, and washed with 1% HCl, NaHCO$_{3}$, and brine. The organic phase was dried over NaSO$_{4}$ and evaporation under reduced pressure followed by purification by flash chromatography using 20% EtOAc in hexanes as eluent to afford Compound 31 as a yellowish-white solid (90% yield).

$^{1}$H NMR (500 MHz, CDCl$_{3}$) −δ: 7.48 (d, J=1.5 Hz, 1H), 7.00 (d, J=1.5 Hz, 1H), 1.64 (s, 9H).

1-Boc-2-(TIPS-acetylene)imidazole (Compound 32, Scheme 19) was prepared from Compound 31 (1-boc-2-iodoimidazole) as described hereinabove, and the crude product was purified by flash chromatography on silica gel using ethyl acetate/hexane (15:85) as the eluent. Compound 32 afforded as a faint yellow oil (87% yield).

$^1$H NMR (500 MHz, CDCl$_3$) −δ: 7.30 (d, J=1.5 Hz, 1H), 6.94 (d, J=1.5 Hz, 1H), 1.58 (s, 9H), 1.3-1.10 (bm, 21H);

$^{13}$C NMR (125 MHz, CDCl$_3$) −δ: 146.2, 131.3, 129.5, 118.6, 97, 95.8, 85.7, 27.8, 18.5, 11.2;

MS (ESI), m/z: 349 (MH$^+$), 371 (MNa$^+$).

1-Boc-2-(acetylene)imidazole (Compound 33, Scheme 19) was prepared from Compound 32 (1-Boc-2-(TIPS-acetylene)-imidazole) as described hereinabove, and the residue was purified by flash chromatography on silica gel using ethyl acetate/hexane (3:7) as the eluent. Compound 33 was afforded as a faint brownish solid (87% yield).

$^1$H NMR (500 MHz, CDCl$_3$) −δ: 7.40 (d, J=2 Hz, 1H), 7.00 (d, J=1.5 Hz, 1H), 3.35 (s, 1H), 1.61 (s, 9H).

1,1'-Boc-2,2'-(ethyne-1,2-diyl)bis-imidazole (Compound 34, Scheme 19) was prepared from Compound 33 (1-Boc-2-(acetylene)imidazole) as described hereinabove, and the crude residue was purified by flash chromatography on silica gel using ethyl acetate/hexane (4:8) as the eluent. Compound 34 was afforded as yellowish solid (83% yield).

$^1$H NMR (500 MHz, CDCl$_3$) −δ: 7.47 (d, J=1.5 Hz, 1H), 7.07 (d, J=1.5 Hz, 1H), 1.63 (s, 9H);

$^{13}$C NMR (125 MHz, CDCl$_3$) −δ: 146.4, 130.4, 119.6, 86.7, 82.5, 27.8;

MS (ESI), m/z: 359 (MH$^+$), 381 (MNa$^+$).

1,2-Di(imidazol-2-yl)ethyne (Compound 3, Scheme 19) was prepared from Compound 34 (1,1'-Boc-2,2'-(ethyne-1,2-diyl)bis-imidazole) as described hereinabove. Compound 3 was afforded as a yellowish solid (88% yield).

$^1$H NMR {500 MHz, D$_2$O:TFA (4:1)} −δ: 7.77 (s, 4H). MS (ESI), m/z: 159 (MH$^+$).

Host-guest complex of Compound 3 and Compound 1 (Complex 3a, Scheme 19) was prepared by a 1:1 host-guest complexion according to the general procedure described hereinabove.

$^1$H NMR {500 MHz, D$_2$O:TFA (4:1)} −δ: 7.78 (s, 4H), 5.88 (d, J=15.5 Hz, 12H), 5.62 (s, 12), 4.35 (d, J=15.5 Hz, 12H).

1,1'-Boc-2,2'-(buta-1,3-diyne-1,4-diyl)bis-imidazole (Compound 35, Scheme 19) was prepared by adding CuCl (120 mg, 1.2 mmol) to a stirred solution of Compound 33 (1-Boc-2-(acetylene)imidazole, 225 mg, 1.2 mmol) in dry pyridine (10 ml) under O$_2$ for 4 hours at room temperature. The resulting residue was diluted with EtOAc (50 ml), washed successively with saturated NH$_4$Cl, 1N HCl solution (20 ml) and brine, and dried over NaSO$_4$. Thereafter the reaction mixture was concentrated, and the residue was purified by flash chromatography using EtOAc/hexane (4:6) as an eluent to afford Compound 35 (85% yield) as a yellowish solid.

$^1$H NMR (500 MHz, CDCl$_3$) −δ: 7.4 (d, J=1.5 Hz, 1H), 7.05 (d, J=1.5 Hz, 1H), 1.64 (s, 9H);

$^{13}$C NMR (125 MHz, CDCl$_3$) −δ: 146.2, 130.6, 129.8, 119.9, 86.9, 76.7, 73.1, 27.8;

MS (ESI), m/z: 383 (MH$^+$), 405 (MNa$^+$).

1,4-Di-(imidazol-2-yl)buta-1,3-diyne (Compound 4, Scheme 19) was prepared from Compound 35 as described hereinabove to afford Compound 4 (80% yield) as a yellowish solid.

$^1$H NMR {500 MHz, D$_2$O:TFA (4:0) −δ: 7.73 (s, 4H); MS (ESI), m/z: 183 (MH$^+$).

Host-guest complex of Compound 4 and Compound 1 (Complex 4a, Scheme 19) was prepared by a 1:1 host-guest complexion according to the general procedure described hereinabove.

Complex 4a was crystallized and the crystal structure thereof was elucidate using X-ray crystallography, and the results of the experiment are presented hereinbelow.

$^1$H NMR {500 MHz, D$_2$O:TFA (4:0) −δ: 7.9 (s, 2H), 7.75 (s, 2H), 5.87 (d, J=15.5 Hz, 12H), 5.72 (s, 12H), 4.44 (d, J=15.5 Hz, 12H);

MS (ESI), m/z: 1179.36 (MH$^+$), 1177 (MH$^-$).

2-(8-(1H-imidazol-2-yl)octa-1,3,5,7-tetraynyl)-1H-imidazole (Compound 7, Scheme 19) was prepared from the iodination of TIPS-acetylene Compound 36 to form 2-iodo-TIPS-acetylene Compound 37, as presented in Scheme 19 hereinabove. Subsequently Pd$^{II}$-catalyzed cross-coupling between Compound 33 and Compound 37 with CuI and Et$_3$N afforded 38 in 70% yield. Subsequent removal of the TIPS group by TBAF afforded Compound 39, and oxidative coupling of this produces Compound 40 in 75% yield. The Boc groups were removed from Compound 40 by TFA in CH$_2$Cl$_2$ to yield Compound 7, as presented in Scheme 19 hereinabove.

2-(6-(1H-imidazol-2-yl)hexa-1,3,5-triynyl)-1H-imidazole (Compound 6, Scheme 19) was prepared, as presented in Scheme 19 hereinabove, from imidazole wherein the free NH group therein was protected in the N-THP-Imidazole to afford Compound 43 from THP-Cl (Compound 42). Compound 42 was obtained from 3,4-dihydro-2H-pyran (Compound 41). Iodination of Compound 43 yielded Compound 44. The Pd$^{II}$-catalyzed cross-coupling reaction of Compound 44 with TIPS-acetylene (Compound 36) afforded Compound 45 in 86% yield. The TIPS group was removed by TBAF at −78° C. to afford Compound 46, and subsequent iodination afforded Compound 47 by using LDA and I$_2$. Pd$^{II}$-catalyzed cross-coupling of Compound 47 with Compound 39, using similar reagents and conditions yielded Compound 48 in 50%. The protecting groups were thereafter removed using TFA in CH$_2$Cl$_2$ to afford Compound 6, as presented in Scheme 19 hereinabove.

2-(4-(1H-imidazol-2-yl)buta-1,3-diynyl)-1-benzyl-1H-imidazole (Compound 5, Scheme 19) was prepared, as presented in Scheme 19 hereinabove, from the 1-benzyl imidazol Compound 49, followed by iodination thereof by LDA and iodide to afford Compound 50. Pd$^{II}$-catalyzed cross-coupling reaction of Compound 50 with Compound 39 yielded Compound 51 in 65% yield, and finally the Boc group was removed to produce Compound 5, as presented in Scheme 19 hereinabove.

(Iodoethynyl)triisopropylsilane (Compound 37, Scheme 19) was prepared by adding nBuLi (2.5 M in hexane, 21.7 ml, 34.8 mmol) to a stirred solution of Compound 36 (TIPS-acetylene, 5 grams, 27.5 mmol) in dry THF (50 ml) at −78° C. under a argon atmosphere. The reaction mixture was stirred at 0° C. for 1 hour, and then iodine (7.7 grams, 30.3 mmol) in THF (25 ml) was then added dropwise thereto. The reaction mixture was allowed to reach room temperature and stirred for 1 additional hour. The reaction mixture was quenched with aqueous NH$_4$Cl and extracted with ethyl ether, and the combined organic phase was washed with 1% HCl, sodium thiosulfate, and brine, dried over MgSO$_4$ and concentrated to afford Compound 37 (85% yield) as a colorless oil.

1-Boc-2-((triisopropylsilyl)buta-1,3-diynyl)-imidazole-1 (Compound 38, Scheme 19) was prepared as described hereinabove from the mixture of Compound 37 and Compound 33. Compound 38 was afforded as a faint brownish oil (70% yield).

$^1$H NMR (500 MHz, CDCl$_3$) −δ: 7.44 (d, J=1.5 Hz, 1H), 7.02 (d, J=1.5 Hz, 1H), 1.64 (s, 9H) 1.10-1.00 (bm, 21H);

$^{13}$C NMR (125 MHz, CDCl$_3$) −δ: 146.4, 130.3, 130.1, 119.5, 65.2, 27.8, 18.5, 11.2;

MS (ESI), m/z: 373 (MH$^+$), 395 (MNa$^+$).

1-Boc-2-(buta-1,3-diynyl)-imidazole (Compound 39, Scheme 19) was prepared as described hereinabove from Compound 38 to afford Compound 39 as a yellowish solid (85% yield).

$^1$H NMR (500 MHz, CDCl$_3$) –δ: 7.44 (d, J=1.5 Hz, 1H), 7.02 (d, J=1.5 Hz, 1H), 2.58 (s, 1H), 1.63 (s, 9H);

$^{13}$C NMR (125 MHz, CDCl$_3$) –δ: 146.2, 130.3, 129.7, 119.7, 86.8, 73.6, 67.6, 65, 27.8;

MS (ESI), m/z: 217.1 (MH$^+$), 239.08 (MNa$^+$).

1,1'-Boc-2,2'-(octa-1,3,5,7-tetrayne-1,8-diyl)bis-imidazole (Compound 40, Scheme 19) was prepared by adding CuCl (70 mg, 0.7 mmol) to a stirred solution of Compound 39 (1-Boc-2-(acetylene)imidazole, 150 mg, 0.7 mmol) in dry pyridine (5 ml) under O$_2$ for 4 hours at room temperature. The reaction mixture was thereafter diluted with EtOAc (50 ml), and washed successively with aqueous NH$_4$Cl, 1N HCl (20 ml), brine and dried over NaSO$_4$. After concentration, the residue was purified by flash chromatography using EtOAc/hexane (4:6) as an eluent to afford Compound 40 as a yellowish solid (75% yield).

$^1$H NMR (500 MHz, CDCl$_3$) –δ: 7.48 (d, J=1.5 Hz, 1H), 7.07 (d, J=1.5 Hz, 1H), 1.65 (s, 9H);

$^{13}$C NMR (125 MHz, CDCl$_3$) –δ: 146.1, 130.9, 129.4, 120.2, 87.2, 77.6, 68.9, 67.5, 64.1, 27.8;

MS (ESI), m/z: 431 (MH$^+$), 453 (MNa$^+$).

1,8-Di-(imidazol-2-yl)octa-1,3,5,7-tetrayne (Compound 7, Scheme 19) was prepared from Compound 40 as described hereinabove to afford Compound 7 as a yellowish solid (82% yield).

$^1$H NMR {500 MHz, D$_2$O:TFA (4:0} –δ: 7.69 (s, 4H);

MS (ESI), m/z: 231 (MH$^+$).

2-Chlorotetrahydro-2H-pyran (Compound 42, Scheme 19) was prepared by bubbling dry HCl gas, (obtained by slow addition of H$_2$SO$_4$ over NaCl) through a solution of Compound 41 (3,4-dihydro-2H-pyran, 21.0 g, 0.25 mol) in anhydrous diethyl ether (150 ml) for 2 hours. The reaction mixture was cooled to –78° C., and the solution was purged with N$_2$ in order to remove excess HCl. Compound 42 was afforded as an unstable colorless oil (19 grams, 64% yield) by fractional distillation of the residue under reduced pressure (boiling point 36-39° C., 18 mmHg).

$^1$H NMR (300 MHz, CDCl$_3$) –δ: 6.27 (t, 1H), 3.90-4.10 (m, 1H), 3.70-3.80 (m, 1H), 1.90-2.20 (m, 2H), 1.40-1.80 (m, 4H).

1-THP-imidazole (Compound 43, Scheme 19) was prepared by adding Et$_3$N (4.6 ml, 33 mmol) to a solution of Compound 27 (imidazole, 1.5 g, 22 mmol) in 100 ml of DMF/MeCN (1:1, w/w) at 0° C. while stirring for 0.5 hours. Thereafter Compound 42 (4 grams, 33 mmol) in DMF (15 ml) was added dropwise to reaction mixture and allowed to stirred over night at room temperature. The reaction mixture was quenched with water, concentrated under reduced pressure, and the residue was dissolved in EtOAc, washed with NaHCO$_3$, brine, dried over MgSO$_4$ and concentrated to afford Compound 43 as thick oil (2.2 grams, 65% yield).

$^1$H NMR (300 MHz, CDCl$_3$) –δ: 7.54 (s, 1H), 7.00 (m, 2H), 5.80 (t, 1H), 3.50 (m, 2H), 2.10-1.90 (m, 2H), 1.80-1.40 (m, 4H).

1-THP-2-iodoimidazole (Compound 44, Scheme 19) was prepared by adding n-BuLi (5.4 ml, 8.7 mmol) to a solution of Compound 43 (1.1 grams, 7.2 mmol) in dry THF (30 ml) at 0° C. while stirring for 15 minutes. Thereafter the reaction mixture was allowed to warm to room temperature while stirring for one additional hour. Thereafter iodine (2 grams, 7.9 mmol) in THF (5 ml) was added dropwise to reaction mixture at 0° C. and again allowed to warm to room temperature. After 1 hour of stirring at room temperature, the reaction mixture was quenched with aqueous NH$_4$Cl and concentrated. The residue was dissolved in EtOAc and washed with 1% HCl, NaHCO$_3$, NaS$_2$O$_3$, brine, dried over NaSO$_4$ and concentrated again under reduced pressure to afford a crude product which was purified by flash chromatography using EtOAc:Hexane (4:6) as eluent. Compound 44 was afforded as a white solid (75% yield).

$^1$H NMR (500 MHz, CDCl$_3$) –δ: 7.18 (d, J=1.5 Hz, 1H), 7.07 (d, J=1.5 Hz, 1H), 5.13 (dd, J=10.5 Hz, 1H), 4.10 (m, 1H), 3.66 (dt, J=3, 12 Hz, 1H), 1.94-1.57 (m, 6H).

1-THP-2-((triisopropylsilyl)ethynyl-imidazole (Compound 45, Scheme 19) was prepared as described hereinabove from the mixture of Compound 44 and Compound 36 to afford Compound 45 as a thick oil (86% yield).

$^1$H NMR (500 MHz, CDCl$_3$) –δ: 7.08 (s, 1H), 7.00 (s, 1H), 5.47 (dd, J=10.5 Hz, 1H), 4.11-4.08 (m, 1H), 3.59 (dt, J=2.5, 11.5 Hz, 1H), 1.20-1.92 (m, 2H), 1.79-1.54 (m, 4H), 1.16-1.04 (bm, 21H);

$^{13}$C NMR (125 MHz, CDCl$_3$) –δ: 130.8, 129.4, 116.6, 96, 95, 84, 68.7, 32.2, 24.7, 22.9, 18.5, 11;

MS (ESI), m/z: 333 (MH$^+$).

1-THP-2-(ethynyl-2-yl)-imidazole (Compound 46, Scheme 19) was prepared as described hereinabove from Compound 45 to afford Compound 46 as a yellowish solid (92% yield).

$^1$H NMR (500 MHz, CDCl$_3$) –δ: 7.07 (d, J=1.5 Hz, 1H), 6.99 (d, J=1.0 Hz, 1H), 5.39 (dd, J=10.5 Hz, 1H), 4.06 (td, J=2, 11.5 Hz, 1H), 3.62 (dt, J=3, 12 Hz, 1H), 3.31 (s, 1), 1.98-1.88 (m, 2H), 1.79-1.52 (m, 4H);

$^{13}$C NMR (125 MHz, CDCl$_3$) –δ: 129.6, 129.5, 117, 83.6, 81.3, 72.8, 68.5, 32, 24.6, 22.7;

MS (ESI), m/z: 177 (MH$^+$), 199 (MNa$^+$).

1-THP-2-(iodoethynyl-2-yl)-imidazole (Compound 47, Scheme 19) was prepared by adding nBuLi to a solution of iPr$_2$NH (0.4 ml, 0.96 mmol) in dry THF (5 ml) at 0° C. The reaction mixture was allowed to stir at 0° C. for 30 minutes, and then cooled to –78° C. Thereafter, Compound 46 (140 mg, 0.80 mmol) in THF (3 ml) added and the reaction mixture was allowed to stir for 2 hours at the same temperature. Thereafter iodine (224 mg, 0.88 mmol) in THF (3 ml) was added dropwise to reaction mixture at 0° C., and the reaction mixture was allowed to warm to room temperature and stirred for one additional hour. The reaction mixture was quenched with aqueous NH$_4$Cl and concentrated under reduced pressure. The residue was dissolved in EtOAc, washed with 1% HCl, NaHCO$_3$, Na$_2$S$_2$O$_3$, brine, dried over NaSO$_4$, and concentrated to afford a crude product which was purified by column chromatography to afford Compound 47 as yellowish solid (87% yield).

$^1$H NMR (500 MHz, CDCl$_3$) –δ: 7.10 (s, 1H), 7.03 (s, 1H), 5.40 (dd, J=10.5 Hz, 1H), 4.15-4.10 (m, 1H), 3.69 (dt, J=2.5, 11.5 Hz, 1H), 2.04-1.94 (m, 2H), 1.85-1.59 (m, 4H);

$^{13}$C NMR (125 MHz, CDCl$_3$) –δ: 130.8, 129.4, 116.9, 83.8, 83.5, 68.7, 32.2, 24.8, 22.9;

MS (ESI), m/z: 303 (MH$^+$), 325 (MNa$^+$).

1-Boc-imidazole-2-(hexa-1,3,5-triynyl)-1'-THP-imidazole (Compound 48, Scheme 19) was prepared as described hereinabove from the mixture of Compound 47 and Compound 39 to afford Compound as a brownish solid (50% yield).

$^1$H NMR (500 MHz, CDCl$_3$) –δ: 7.45 (d, J=1.5 Hz, 1H), 7.17 (s, 1H), 7.08 (s, 1H), 7.04 (d, J=1.5 Hz, 1H), 5.40 (dd, J=10.5 Hz, 1H), 4.13-4.09 (m, 1H), 3.69 (dt, J=3, 11.5 Hz, 1), 2.03-1.94 (m, 2H), 1.81-1.57 (bm, 13H);

MS (ESI), m/z: 391 (MH$^+$), 413 (MNa$^+$).

1,6-Di-imidazol-hexa-1,3,5-triyne (Compound 6, Scheme 19) was prepared as described hereinabove to afford Compound 6 as a faint brownish solid (60% yield).

$^1$H NMR {500 MHz, D$_2$O:TFA (4:1)} –δ: 7.69 (s, 4H); MS (ESI), m/z: 207.07 (MH$^+$).

1-Benzyl-2-iodo-imidazol (Compound 50, Scheme 19) was prepared by adding n-BuLi, (2.5 M in Hexane, 15.2 ml, 39 mmol) to a stirred solution of diisopropylamine (5.8 ml, 41.1 mmol) in THF (30 ml) at 0° C. After 30 minutes of stirring, the temperature was lowered to –78° C. and Compound 49 (1-benzyl-imidazol, 5 grams, 31.6 mmol) in THF (20 ml) was added thereto. The temperature was then increased to 0° C. and the reaction mixture was stirred at the same temperature for 30 minutes, then cooled down to –78° C. and finally iodine (8.8 grams, 34.8 mmol) in THF (20 ml) was added to the reaction mixture. The reaction mixture was stirred at room temperature for 2 hours and was quenched with aqueous NH$_4$Cl, extracted with ethyl acetate, and the organic layer was washed with brine, dried over Na$_2$SO$_4$, and evaporated under reduced pressure to afford a crude product which was purified by column chromatography using silica gel and ethyl acetate:Hexane (1:1) as eluent to afford Compound 50 as yellow solid (6.5 grams, 72% yield).

$^1$H NMR (500 MHz, CDCl$_3$) –δ: 7.36-7.29 (m, 3H), 7.14-7.11 (m, 3H), 7.00 (s, 1H), 5.09 (s, 2H);

$^{13}$C NMR (125 MHz, CDCl$_3$) –δ: 135.5, 132.9, 128.9, 128.2, 127.2, 123.3, 90.6, 53;

MS (ESI), m/z: 285 (MH$^+$), 307 (MNa$^+$).

tert-Butyl-2-(4-(1-benzyl-imidazole-2-yl)-buta-1,3-diynyl)-imidazole-1-carboxylate (Compound 51, Scheme 19) was prepared as described hereinabove from Compound 50 and Compound 39 (65% yield).

$^1$H NMR (500 MHz, CDCl$_3$) –δ: 7.47 (d, J=1.5 Hz, 1H), 7.37-7.32 (m, 3H), 7.19-7.18 (m, 2H), 7.10 (s, 1H), 7.06 (d, J=1.5 Hz, 1H), 6.94 (s, 1H), 5.21 (s, 2H), 1.62 (s, 9H);

$^{13}$C NMR (125 MHz, CDCl$_3$) –δ: 146.2, 135.5, 131, 130.7, 130.6, 129.8, 129, 128.4, 127.5, 121.5, 119.8, 86.9, 77.3, 76.6, 73.1, 72.5, 50.8, 27.8;

MS (ESI), m/z: 373 (MH$^+$).

2-(4-Imidazol-2-yl)-buta-1,3-diynyl-1-benzyl-imidazole (Compound 5, Scheme 19) was obtained as described hereinabove by removal the Boc group from Compound 51 to afford Compound 5 as a solid (71% yield).

Other various synthetic steps presented in Scheme 19 were as follows: j) CuCl, Pyridine, O$_2$, room temperature, 4 hours, yield 85%; k) 1-Boc-2-(iodoacetylen)imidazole, (PPh$_3$) PdCl$_2$, CuI, Et$_3$N, 40° C., 14 hours, yield 70%; l) HCl gas, ether, –78° C.; m) imidazole, Et$_3$N, DMF/MeCN, room temperature; n) iPr$_2$NH, nBuLi, 12, THF, –78° C. to 0° C.; o) 1-Boc-2(buta-1,3-diynyl)-imidazole, (PPh$_3$) PdCl$_2$, CuI, Et$_3$N, 40° C., 14 hour Preparation of Bis-Ammonium Guest Molecules of Various Lengths Having Unsubstituted Benzene-Based Aromatic Threading Moieties of Various Lengths The entire synthesis of several exemplary bis-ammonium molecules of various lengths having unsubstituted benzene-based aromatic threading moieties, according to some embodiments of the present invention, and their subsequent insertion in a CB[6] molecule to afford the corresponding insertion complex is illustrated.

The preparation of exemplary complexes of guest molecules having an aromatic threading moiety, Compound 8, Compound 9, Compound 10, Compound 11 and Compound 13 is presented in Scheme 20 below.

The preparation of the corresponding insertion complexes using the same together with CB[6] (Compound 1) in H$_2$O, namely Complex 8a, Complex 9a, Complex 10a, Complex 11a and Complex 13a is also presented in Scheme 20 below.

The diamino-aromatic Compound 52 was converted to the corresponding diammonium salt as described hereinabove. The commercially available di-amine compounds, namely Compound 53, Compound 54, Compound 55, and Compound 56 were converted in ammonium salt by using 6N HCl in MeOH to produce Compound 8, Compound 9, Compound 10, Compound 11 and Compound 13 respectively.

Compound 58 was prepared from 1,4 Bis-(hydroxy ethyl)-benzene (Compound 57) by using Ms-Cl in CH$_2$Cl$_2$, which was treated with NaN3 at 80° C. to yield Compound 59 in 76% yield (a two steps reaction). Compound 59 was converted to the corresponding ammonium salt Compound 13 by using PPh$_3$, THF:H$_2$O (1:1, W/W) and 1N HCl.

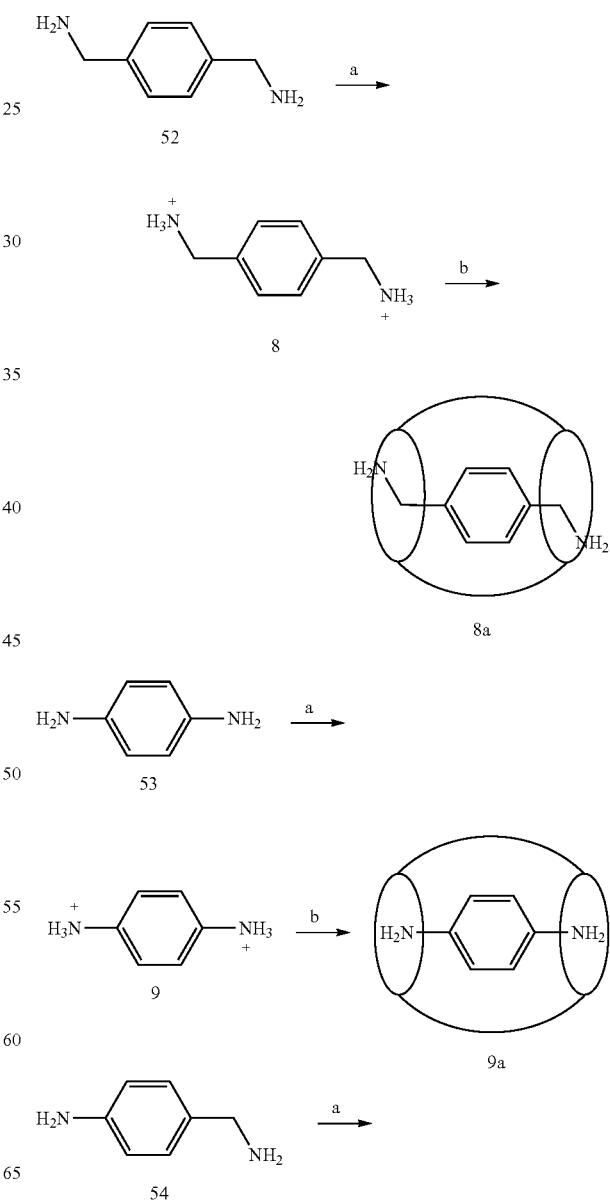

Scheme 20

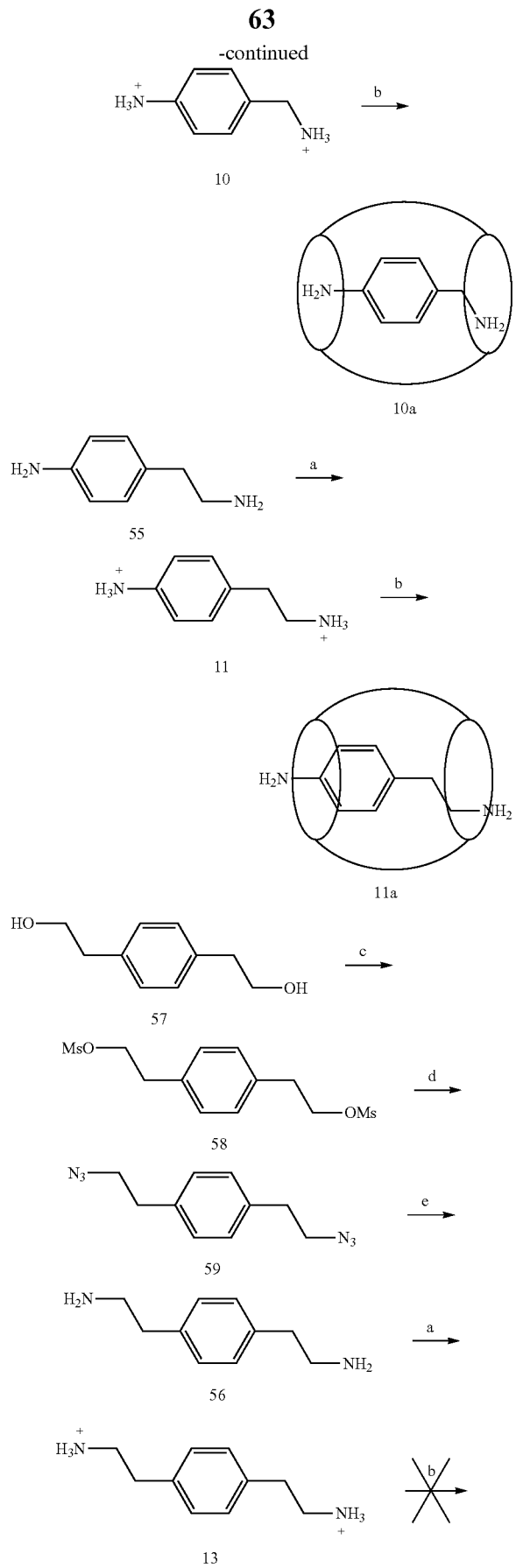

p-Xylylenediamine hydrochloride (Compound 8, Scheme 20): $^1$H NMR (500 MHz, D$_2$O) –δ: 7.55 (s, 4H), 4.25 (s, 4H); MS (ESI), m/z: 137 MH$^+$, 159 MNa$^+$.

Insertion complex of Compound 1 (CB[6]) and Compound 8 (p-xylylenediamine hydrochloride) (Complex 8a, Scheme 20): $^1$H NMR (500 MHz, D$_2$O) –δ: 6.54 (s, 4H), 5.75 (d, J=15.5 Hz, 12H), 5.55 (s, 12H), 4.35 (s, 4H), 4.32 (d, J=16 Hz, 12H);

MS (MALDI-TOF), m/z: 1133.4 MH$^+$.

Benzene-1,4-diamine hydrochloride (Compound 9, Scheme 20): $^1$H NMR (500 MHz, D$_2$O) –δ: 7.57 (s, 4H); MS (ESI), m/z: 109 MH$^+$.

Insertion complex of Compound 1 (CB[6]) and Compound 9 (benzene-1,4-diamine hydrochloride) (Complex 9a, Scheme 20): $^1$H NMR (500 MHz, D$_2$O) –δ: 6.92 (s, 4H), 5.77 (d, J=15.5 Hz, 12H), 5.60 (s, 12H), 4.37 (d, J=16 Hz, 12H); MS (MALDI-TOF), m/z: 1105 MH$^+$.

4-(aminomethyl)benzenamine hydrochloride (Compound 10, Scheme 20): $^1$H NMR (500 MHz, D$_2$O) –δ: 7.63 (d, J=8.5 Hz, 2H), 7.5 (d, J=8.5 Hz, 2H), 4.27 (s, 2H).

Insertion complex of Compound 1 (CB[6]) and Compound 10 (4-(aminomethyl)benzenamine hydrochloride) (Complex 10a, Scheme 20):

$^1$H NMR (500 MHz, D$_2$O) –δ: 6.79 (d, J=8 Hz, 2H), 6.7 (d, J=7.5, 2H), 5.75 (d, J=16 Hz, 12H), 5.57 (s, 12H), 4.42 (s, 2H), 4.34 (q, J=16 Hz, 12H);

MS (MALDI-TOF), m/z: 1119 MH$^+$.

4-(-aminoethyl)benzenamine hydrochloride (Compound 11, Scheme 20): $^1$H NMR (500 MHz, D$_2$O) –δ: 7.49 (d, J=8.5 Hz, 2H), 7.43 (d, J=8.5 Hz, 2H), 3.33 (t, J=14 Hz, 2H), 3.08 (t, J=7.5 Hz, 2H).

Insertion complex of Compound 1 (CB[6]) and Compound 11 (4-(-aminoethyl)benzenamine hydrochloride (Complex 11a, Scheme 20): $^1$H NMR (500 MHz, D$_2$O) –δ: 6.69-6.63 (m, 4H), 5.77 (q, J=15.5 Hz, 12H), 5.53 (s, 12H), 4.31 (q, J=15.5 Hz, 12H), 3.58 (t, J=7.5 Hz, 2H), 3.06 (t, J=7.5 Hz, 2H);

MS (MALDI-TOF), m/z: 1133 MH$^+$.

1,4-Bis-(mesylate ethyl)-benzene (Compound 58, Scheme 20) was prepared by adding MsCl (575 mg 5 mmol) to a solution of 1,4-bis-(hydroxy ethyl)-benzene (Compound 57, 335 mg, 2 mmol) in DCM together and Et$_3$N (1.05 grams, 10 mmol) at 0° C. for 10 minutes. The reaction was stirred for 4 hours at 0° C. and for 1 hour at room temperature, and thereafter diluted with water and extracted twice with DCM (2×30 ml). The combined organic layers were dried and evaporated to afford Compound 58 at a quantitative yield (600 mg).

$^1$H NMR (400 MHz, CDCl$_3$) –δ: 7.16 (s, 4H), 4.37 (t, J=9.2 Hz, 4H), 3.00 (t, J=9.2 Hz, 4H), 2.83 (s, 4H).

1,4-bis-(azido ethyl)-benzene (Compound 59, Scheme 20) was prepared by adding NaN$_3$ (260 mg 4 mmol) to a solution of Compound 58 (1,4-bis-(mesilate-ethyl)-benzene, 300 mg 0.93 mmol) in DMF (4 ml) which was then stirred at 75° C. for 12 hours. After cooling the reaction mixture, water was added and the reaction mixture was extracted twice with ether (2×30 ml). The organic layer was washed twice with water, dried and evaporated under reduced pressure to afford Compound 59 (180 mg, 87% yield).

$^1$H NMR (400 MHz, CDCl$_3$) –δ: 7.20 (s, 4H), 3.51 (t, J=9.6 Hz, 4H), 2.9 (t, J=9.6 Hz, 4H).

1,4-Bis(amine-ethyl)benzene hydrochloride (Compound 13, Scheme 20) was prepared by adding PPh$_3$ (328 mg, 2 mmol) to a solution of Compound 59 (1,4-Bis(azido ethyl) benzene, 180 mg, 0.83 mmol) in 1:1 THF: H2O at room temperature. The reaction mixture was allowed to stir for 24 hours at room temperature, and thereafter 1N HCl was added thereto. The aqueous portion was washed twice with ether (2×30 ml) and lyophilized to afford Compound 13 as a white solid (150 mg, 75% yield).

$^1$H NMR (400 MHz, D$_2$O) –δ: 7.35 (s, 4H), 3.29 (t, J=7.6 Hz, 4H), 3.0 (t, J=7.6 Hz, 4H).

Insertion complex of Compound 1 (CB[6]) and Compound 13 (1,4-bis(amine-ethyl)benzene hydrochloride) (Complex 13a, Scheme 20) can be prepared following similar procedures as described hereinabove.

Other various synthetic steps presented in Scheme 20 were as follows: a) 6 N HCl, MeOH, room temperature, 2 hours; b) CB[6], H$_2$O, 80° C., 16 hours; c) MsCl, Et$_3$N, CH$_2$Cl$_2$, room temperature, over night; d) NaN$_3$, DMF, 80° C., 16 hours, 76% yield in two steps; e) Ph$_3$P, H$_2$O, THF, room temperature, 24 hours, 75% yield.

Preparation of Guest Molecules Used in the Preparation of Switching Devices (Chemical Logic Gates)

The preparation of tri-hydrochloride salt of N-(6-(4-aminobutylamino)hexyl)-4-(methylthio)benzenamine (Compound 24), which can be used in the preparation of chemical logic gates according to some embodiments of the present invention, is illustrated in Scheme 21 below.

Compound 24 was prepared from the commercially available 6-bromo hexanol (Compound 60) and 1,4-dibutane (Compound 62). The free hydroxy group of Compound 60 was protected with TBDMS ether Compound 61 and amine groups of Compound 62 were protected with 1,4-di-Boc-aminobutane to afford Compound 63.

Compound 64 was obtained by the alkylation of Compound 63 with Compound 61 in the presence of NaH and DMF. The TBDMS group was removed using TBAF in THF to afford the alcohol Compound 65, which was thereafter oxidized using PCC to form the aldehyde Compound 66, followed by reductive amination with thio-aniline to afford Compound 67. The Boc groups were remove using 4N HCl in ethanol to afford ammonium salt Compound 24, which was thereafter mixed with CB[6] in H$_2$O to afford a mixture of Complex 24a and Complex 24b, as presented in Scheme 21 below.

Scheme 21

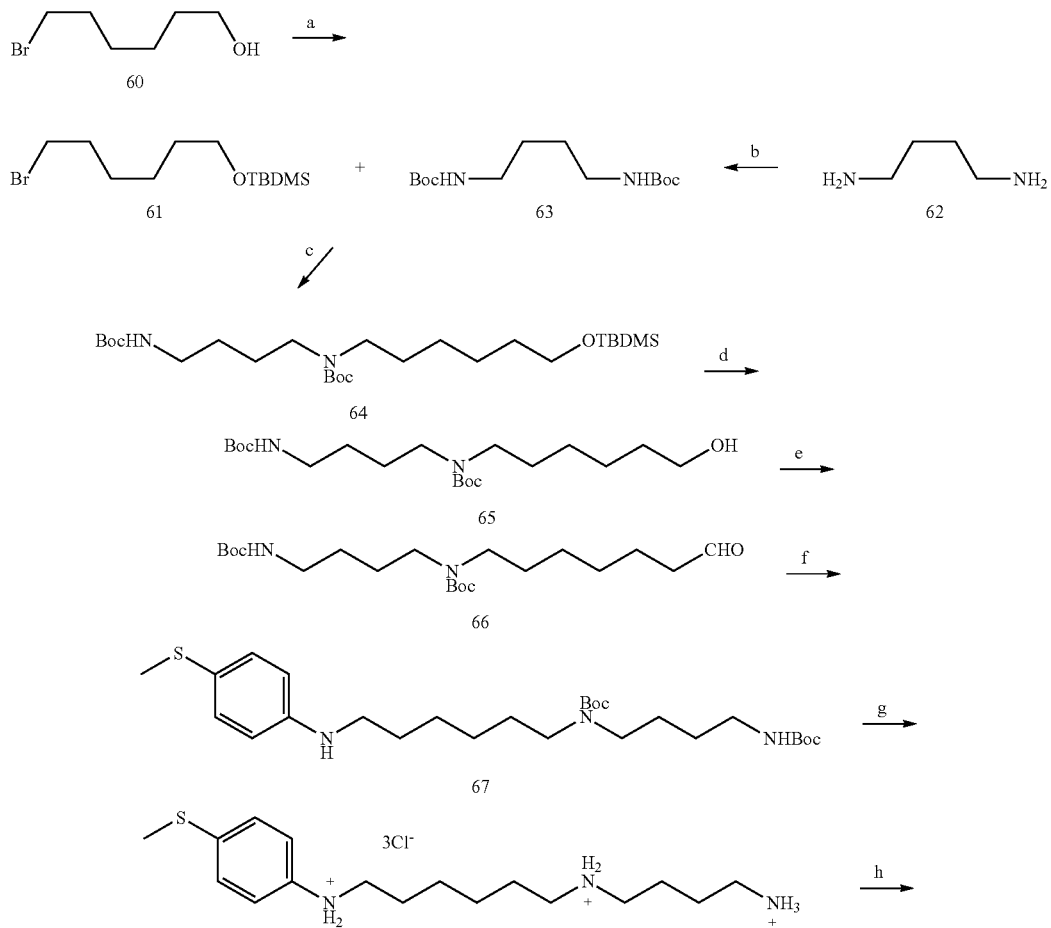

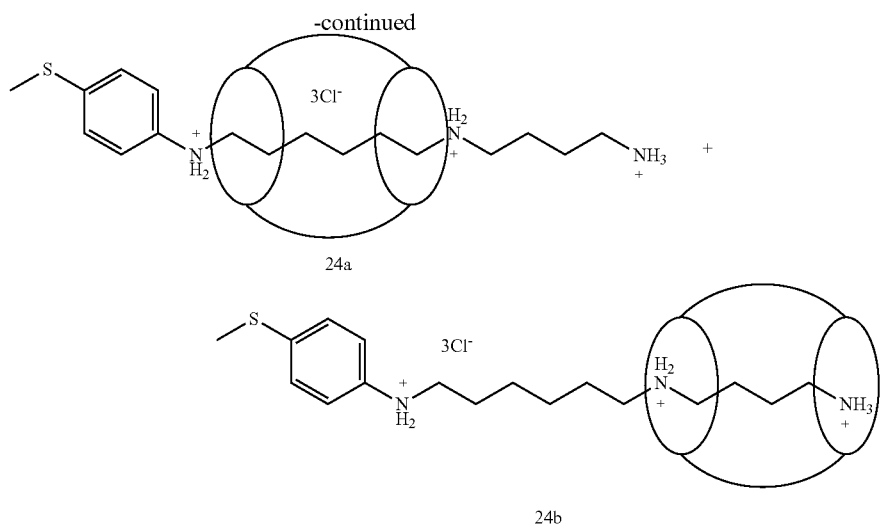

24a

24b

6-Bromo-1-tert-butyldimethylsilyloxy hexane (Compound 61, Scheme 21) was prepared by adding TBSCl (2 grams, 13.26 mmol) to a stirred solution of Compound 60 (6-bromohexanol, 2 grams, 11.05 mmol), triethylamine (2.3 ml, 16.57 mmol) and DMAP (11 mg, 1.1 mmol) in dry $CH_2Cl_2$ (15 ml). The reaction mixture was stirred for 6 hours at room temperature, and upon completion of the reaction as indicated by TLC, the reaction mixture was quenched with aqueous $NH_4Cl$, extracted with $CH_2Cl_2$, the combined organic layer was washed with water and dried over $MgSO_4$, and the solvents were removed under reduced pressure. The residue was purified by column chromatography using silica gel and hexane/ethyl acetate (100:5) as eluent to afford Compound 61 in the form of a colorless oil (3.2 grams, 98% yield).

$^1$H NMR (500 MHz, $CDCl_3$) –δ: 3.603 (t, J=6.5 Hz, 2H), 3.404 (t, J=7 Hz, 2H), 1.90-1.83 (m, 2H), 1.57-1.46 (m, 2H), 1.44-1.41 (m, 2H), 1.38-1.34 (m, 2H), 0.89 (s, 9H), 0.04 (s, 6H);

$^{13}$C NMR (125 MHz, $CDCl_3$) –δ: 63, 33.9, 32.8, 32.6, 28, 26, 25, 18.3, –5.3;

MS (ESI), m/z: 295 ($MH^+$).

1,4-Di(Boc-amino)-butane (Compound 63, Scheme 21) was prepared by adding Boc-anhydride (12 grams, 55 mmol) to a stirred solution of Compound 62 (1,4-diamino-butane, 2.2 grams, 25 mmol) and triethylamine (10.4 ml, 75 mmol) in $CH_2Cl_2$ (50 ml) at room temperature. After 12 hours, the reaction mixture was quenched with aqueous $NH_4Cl$, extracted with $CH_2Cl_2$, and the combined organic layer was washed with 1% HCl, aquwous $NaHCO_3$ and water, dried over $MgSO_4$, and the solvents were removed under reduced pressure to afford Compound 63 as white solid (6.8 grams, 94.5% yield).

$^1$H NMR (500 MHz, $CDCl_3$) –δ: 4.60 (bs, 2NH), 3.1 (s, 4H), 1.45-1.46 (m, 4H), 1.41 (s, 18H).

6-(1,4-Di(boc-amino)-butane)-1-tert-butyldimethylsilyloxy hexane (Compound 64, Scheme 21) was prepared by adding NaH (0.75 grams, 19 mmol) to a stirred solution of Compound 63 (2.7 grams, 9.4 mmol) in DMF (30 ml) at room temperature. After 30 minutes additional portion of NaH, and Compound 61 (1.4 grams, 4.7 mmol) were added and the reaction mixture was stirred for 48 hours at room temperature. The reaction mixture was thereafter quenched with aqueous $NH_4Cl$, extracted with ether, the combined organic layer was washed with brine, dried over $MgSO_4$ and the solvents were removed under reduced pressure. The residue was purified by column chromatography using silica gel and 20-30% ethyl acetate in haxene as eluent to afford Compound 64 in the form of a colorless oil (1.5 grams, 64% yield).

$^1$H NMR (500 MHz, $CDCl_3$) –δ: 4.61 (bs, NH), 3.58 (t, J=6 Hz, 2H), 3.13-3.10 (m, 6H), 1.55-1.45 (m, 8H), 1.42 (s, 18H), 1.35-1.22 (m, 4H), 0.87 (s, 9H), 0.03 (s, 6H);

MS– (ESI), m/z: 503 $MH^+$, 525 $MNa^+$.

6-(1,4-Di(Boc-amino)-butane)1-hexanol (Compound 65, Scheme 21) was prepared by adding TBAF (1 M in THF, 3.5 ml, 3.5 mmol) to a solution of Compound 64 (1.5 grams, 2.9 mmol) in dry THF (30 ml) at 0° C., and stirring the mixture for 4 hours at room temperature. The crude product was extracted using diethyl ether/water, followed by purification on silica gel using hexanes/ethyl acetate (1:1) as eluent to afford Compound 65 as colorless oil (0.95 grams, 84% yield).

$^1$H NMR (500 MHz, $CDCl_3$) –δ: 4.71 (bs, NH), 3.58 (t, J=6.5 Hz, 2H), 3.8-3.07 (m, 6H), 1.54-1.42 (m, 8H), 1.40 (s, 18H), 1.36-1.33 (m, 2H), 1.28-1.25 (m, 2H);

MS (ESI), m/z: 389 $MH^+$, 411 $MNa^+$.

6-(1,4-Di(Boc-amino)-butane)1-hexanal (Compound 65, Scheme 21) was prepared by converting Compound 65 (154 mg, 0.4 mmol) to the corresponding aldehyde by stirring with a mixture of PCC (172 mg, 0.8 mmol) and celite (172 mg) in $CH_2Cl_2$ (5 ml) at room temperature for one hour. The crude aldehyde was purified by column chromatography using silica gel and hexanes-EtOAc (7:3) as eluent to afford Compound 66 (145 mg, 94% yield).

$^1$H NMR (500 MHz, $CDCl_3$) –δ: 9.76 (s, CHO), 4.56 (bs, NH), 3.15-3.10 (m, 6H), 2.43 (t, J=7 Hz, 2H), 1.68-1.28 (m, 28H);

MS (ESI), m/z: 409 $MNa^+$.

6-(1,4-Di(Boc-amino)-butane)1-thiomethyl-aniline-hexane (Compound 67, Scheme 21) was prepared from a mixture of Compound 66 (135 mg, 0.35 mmol), 4-thio-methyl aniline (50 mg, 0.35 mmol), acetic acid (21 mg, 0.35 mmol) and sodium triacetoxy borohydride (150 mg, 07 mmol), which was stirred in THF (5 ml) at room temperature for 18 hours. The reaction mixture was quenched with aqueous $NH_4Cl$, extracted with ethyl acetate, the combined organic layer was washed with $NaHCO_3$, brine, dried over $MgSO_4$ and the solvents were removed under reduced pressure. The residue was purified by column chromatography using silica gel and 30-40% ethyl acetate in haxene as eluent to afford Compound 67 in the form of colorless oil (120 mg, 68% yield).

$^1$H NMR (500 MHz, CDCl$_3$) –δ: 7.19 (d, J=9 Hz, 2H), 6.52 (d, J=8 Hz, 2H), 4.628 (bs, NH), 3.69 (bs, NH), 3.10-3.1 (m, 8H), 2.39 (s, 3H), 1.6-1.27 (m, 30H);

MS (ESI), m/z: 510 MH$^+$, 532 MNa$^+$.

6-(1,4-Di-aminobutane)1-thiomethyl aniline-hexane hydrochloride (Compound 24, Scheme 21) was prepared by removing the Boc protecting groups from Compound 67 (100 mg) as described hereinabove to afford Compound 24 as a white solid (90 mg).

$^1$H NMR (500 MHz, D$_2$O) –δ: 7.49 (d, J=8 Hz, 2H), 7.43 (d, J=8.5 Hz, 2H), 3.44 (t, J=7.5 Hz, 2H), 3.10-3.03 (m, 6H), 2.55 (s, 3H), 1.78-1.68 (bm, 8H), 1.43 (bs, 4H);

$^{13}$C NMR (125 MHz, CDCl$_3$) –δ: 140.8, 132, 127.8, 123.4, 52, 47.9, 47.2, 39.2, 25.7, 25.6, 25.5, 25.2, 24.4, 23.2, 14.8.

Insertion complexes of Compound 1 (CB[6]) and Compound 24 (6-(1,4-di-aminobutane)1-thiomethyl aniline-hexane hydrochloride) (Complex 24a and Complex 24b, Scheme 21) were prepared using Compound 24 as described hereinabove to afford a mixture of Complex 24a and Complex 24b.

MS (MALDI-TOF), m/z: 1307 MH$^+$.

Other various synthetic steps presented in Scheme 21 were as follows: a) TBDMS-Cl, CH$_2$Cl$_2$, Et$_3$N, room temperature, 3 hours 95% yield; b) (Boc)$_2$O, Et$_3$N, CH$_2$Cl$_2$, room temperature, 12 hours, 92% yield; c) NaH, DMF, room temperature, 18 hours, 60% yield; d) TBAF, THF, room temperature, 4 hours, 88%; e) PCC, celite CH$_2$Cl$_2$, room temperature, 1 hour, 98% yield; f) 4-(methyl thio) aniline, sodium triacetoxy boro hydride, AcOH, THF, room temperature, 18 hours, 75% yield; g) 4 N HCl, EtOH, room temperature, 16 hours, 85% yield; h) CB[6], H$_2$O, room temperature, 16 hours.

Preparation of Di-Azide Guest Molecule (Compound 73) En Route Towards Rotaxanes of CB[6] and Uncharged Guest Molecules Preparation of the di-azide, Compound 73, an exemplary guest molecule according to some embodiments of the present invention was performed en route towards the preparation of rotaxanes made of CB[6] and uncharged guest molecules, as presented hereinabove.

The exemplary guest molecule was prepared, as illustrated in Scheme 22 below, using 2-amino-ethanol Compound 68, wherein the amino group was protected by (Boc)$_2$O to afford Compound 69. Thereafter the hydroxy group was activated to form the mesylate Compound 70, which was subsequently reacted with NaN$_3$ to afford Compound 71.

Compound 71 was reacted with α,α'-dibromo-p-xylene in the presence of NaH in DMF to afford Compound 72. Subsequently the Boc groups were removed by 4N HCl in ethanol to afford the diamino with ammonium salt Compound 73, which was mixed with CB[6] in H$_2$O to produce Complex 74.

Scheme 22

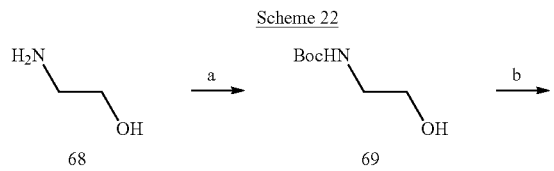

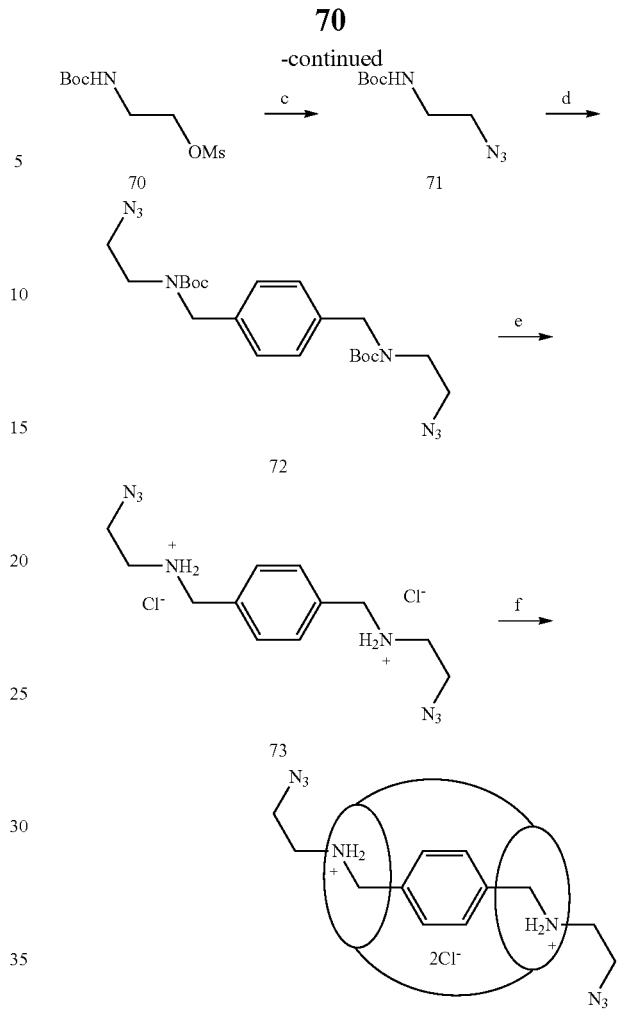

N-Boc-2-azidoethyl-amine (Compound 71, Scheme 22) was prepared by adding Boc-anhydride (4.3 g, 19.6 mmol) to a stirred solution of ethanolamine (Compound 68, 1 grams, 16.4 mmol) and Et$_3$N (3.4 ml, 24.6 mmol) in CH$_2$Cl$_2$ (25 ml) at 0° C. The reaction mixture was stirred overnight and thereafter quenched with aqueous NH$_4$Cl, extracted with CH$_2$Cl$_2$, the combined organic layer was washed with 1% HCl in water, NaHCO$_3$, water, dried over MgSO$_4$ and the solvents were removed under reduced pressure. The residue was purified by column chromatography using silica gel and ethyl acetate:hexane (8:2) as eluent to afford Compound 69 as colorless oil (2.5 grams, 95% yield).

Compound 70 (Scheme 22) was prepared by adding mesylate-Cl (340 mg, 3 mmol) to a solution of Compound 69 (390 mg, 2.4 mmol) and triethyl amine (0.5 ml, 3.6 mmol) in CH$_2$Cl$_2$ (15 ml) at 0° C. and the mixture was stirred for 2 hours at room temperature. Thereafter the reaction mixture was extracted with water and CH$_2$Cl$_2$, dried over MgSO$_4$, and the solvents were evaporated under reduced pressure to afford Compound 70, which was used without further purification.

Compound 71 (Scheme 22) was prepared form a mixture of the mesilate Compound 70 (645 mg, 2.7 mmol) and NaN$_3$ (210 mg, 3.2 mmol) in DMF (10 ml) which was stirred at 80° C. for 16 hours. Upon completion of the reaction, as indicated by TLC, the reaction mixture was quenched with aqueous NH$_4$Cl, extracted with ether, the combined organic layer was washed with brine, dried over MgSO$_4$, and the solvents were removed under reduced pressure. The residue was purified by column chromatography using silica gel and ethyl acetate:hexane (4:6) as eluent to afford the azide Compound 71 as colorless oil (425 mg, 85% yield in two steps).

$^1$H NMR (500 MHz, CDCl$_3$) –δ: 4.8 (bs, NH), 3.41 (t, J=5.5 Hz, 2H), 3.3 (q, J=5.5 Hz, 2H), 1.45 (s, 9H);

MS (ESI), m/z: 209 MNa$^+$.

N,N'-Di-Boc-di-(azidoethyl)-p-xylylene-diamine (Compound 72, Scheme 22) was prepared by adding NaH (80 mg, 2 mmol) to a stirred solution of Compound 64 (α,α-dibromo-p-xylylene, mg, 0.24 mmol) in DMF (5 ml) at room temperature. After one hour the azide Compound 71 was added to the reaction mixture which was stirred for 24 hours at room temperature. The reaction mixture was thereafter quenched with aqueous NH$_4$Cl, extracted with ethyl ether, the combined organic layer were washed with brine, dried over MgSO$_4$, and the solvents were removed under reduced pressure. The residue was purified by column chromatography using silica gel and ethyl acetate:hexane (2:8) as eluent to afford Compound 72 (80 mg, 70% yield).

$^1$H NMR (500 MHz, CDCl$_3$) –δ: 7.19 (s, 4H), 4.48 (s, 4H), 3.4-3.3 (m, 8H), 1.50 (s, 18H).

N,N'-di-(azidoethyl)-p-xylylene-diamine hydrochloride (Compound 73, Scheme 22) was prepared by removal of the Boc protecting group from Compound 72 as described hereinabove to afford Compound 73.

$^1$H NMR (500 MHz, D$_2$O) –δ: 7.6 (s, 4H), 4.36 (s, 4H), 3.8 (t, J=5.5 Hz, 4H), 3.32 (t, J=5.5 Hz, 4H);

MS (ESI), m/z: 275 MH$^+$, 297 MNa$^+$.

Insertion complex of Compound 1 (CB[6]) with Compound 73 (N,N'-di-(azidoethyl)-p-xylylene diamine hydrochloride (Complex 74) was obtained as described hereinabove.

$^1$H NMR (500 MHz, D$_2$O) –δ: 6.57 (s, 4H), 5.79 (d, J=15.5 Hz, 12H), 5.57 (s, 12H), 4.44 (s, 4H), 4.34 (d, J=15.5 Hz, 12H), 4.14 (t, J=5 Hz, 4H), 3.60 (t, J=5.5 Hz, 4H).

Other various synthetic steps presented in Scheme 22 were as follows: a) (Boc)$_2$O, Et$_3$N, CH$_2$Cl$_2$, room temperature, 12 hours, 96% yield; b) MsCl, Et$_3$N, CH$_2$Cl$_2$, 0° C., room temperature, 2 hours,; c) NaN$_3$, DMF, 80° C., 16 hours, 95% yield in two steps; d) α,α'-dibromo-p-xylene, NaH, DNF, room temperature, 48 hours, 70% yield; e) 4 N HCl, EtOH, room temperature, 16 hours, 75% yield; f) CB[6], H$_2$O, 80° C., room temperature, 20 hours.

Preparation of Di-Alkyne Guest Molecule (Compound 78) En Route Towards Rotaxanes of CB[6] and Uncharged Guest Molecules Preparation of the di-alkyne, Compound 78, an exemplary guest molecule according to some embodiments of the present invention, was performed en route towards the preparation of rotaxanes of CB[6] and uncharged guest molecules, as presented hereinabove.

The exemplary guest molecule was prepared, as illustrated in Scheme 23 below, using diamino-p-xylylene Compound 75. The diamino group were first protected by Boc-amine to afford Compound 76 and alkylated with propargyl-bromide in the presence of NaH in DMF to afford Compound 77. The Boc groups were removed using 4N HCl in ethanol to afford diammonium salt Compound 78.

Compound 78 was subsequently mixed with CB[6] in water at reflux to produce Complex 79, as presented in.

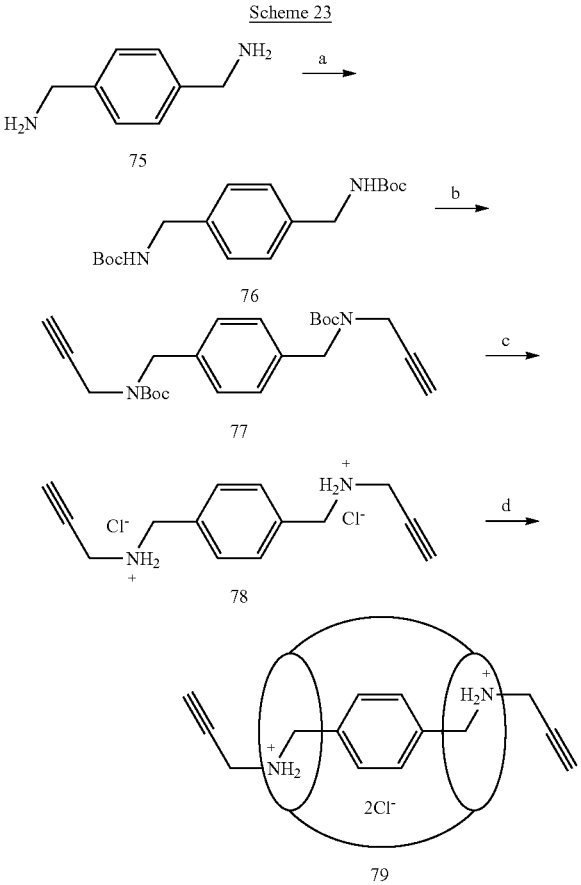

Scheme 23

(N,N'-Di-Boc)-p-xylylene diamine (Compound 76, Scheme 23) was prepared by adding Boc-anhydride to a stirred solution of Compound 75 (xylylene amine, 2 grams, 14.7 mmol) and triethylamine (6 ml, 44 mmol) in CH$_2$Cl$_2$ (50 ml), and stirring the mixture over night at room temperature. Thereafter the reaction mixture was quenched with NH$_4$Cl, extracted with CH$_2$Cl$_2$, washed with 1% HCl, NaHCO$_3$, brine, dried over MgSO$_4$, and evaporated solvents under reduced pressure. The residue was purified by column chromatography using silica gel and 60-80% ethyl acetate in hexane as eluent to afford Compound 76 as a white solid (4.5 grams, 92% yield).

$^1$H NMR (500 MHz, CDCl$_3$) –δ: 7.24 (s, 4H), 4.82 (bs, NH), 4.28 (s, 4H), 1.45 (s, 18H).

N,N'-dipropargyl-N,N'-di-boc-p-xylylene diamine (Compound 77, Scheme 23) was prepared by adding NaH (1 g, 24 mmol) to a stirred solution of Compound 76 (1 gram, 3 mmol) in DMF (20 ml), and stirring the reaction mixture for one hour. Therafter propargyl bromide (1.5 g, 12 mmol) was added to the reaction mixture, and the mixture was stirred for 6 hours at room temperature until no starting material was detected by TLC. The reaction mixture was extracted and concentrated, and the residue was purified by column chromatography using 10% ethyl acetate in hexane as eluent to afford 77 as yellowish oil (1 grams, 82% yield).

$^1$H NMR (500 MHz, CDCl$_3$) –δ: 7.22 (s, 4H), 4.53 (s, 4H), 3.96 (bd, J=64 Hz, 4H), 2.2 (s, 2H), 1.48 (s, 18H). MS (ESI), m/z: 413 MH$^+$, 435 MNa$^+$.

N,N'-dipropargyl-p-xylylene-diamine hydrochloride (Compound 78, Scheme 23) was prepared as described hereinabove to afford Compound 78 from Compound 77 as white solid.

¹H NMR (500 MHz, D₂O) –δ: 7.67 (s, 4H), 4.41 (s, 4H), 3.86 (s, 4H), 2.26 (s, 2H)

MS (ESI), m/z: 213 MH⁺, 235 MNa⁺.

Insertion complex of Compound 1 (CB[6]) and Compound 78 (N,N'-dipropargyl-p-xylylene diamine hydrochloride) (Complex 79, Scheme 23) was obtained as described hereinabove from a mixture of Compound 78 which was stirred for one hour in H₂O and heated to 120° C. for 48 hours to afford Complex 79.

¹H NMR (500 MHz, D₂O) –δ: 6.58 (s, 4H), 5.76 (d, J=15.5 Hz, 12H), 5.57 (s, 12H), 4.5 (s, 4H), 4.34 (d, J=15.5 Hz, 12H);

MS (MALDI-TOF), m/z: 1212 (Mavg).

Other various synthetic steps presented in Scheme 23 were as follows: a) (Boc)₂O, Et₃N, CH₂Cl₂, room temperature, 12 hours, 90% yield; b) Propagyl bromide, NaH, DMF, room temperature, 6 hours, 70% yield; c) 4 N HCl, EtOH, room temperature, 16 hours, 70% yield; d) CB[6], H₂O, 120° C., 24 hours.

Preparation of Branched Amino-Azide Guest Molecule (Compound IV) En Route Towards Rotaxanes of CB[6] and Uncharged Guest Molecules An exemplary guest molecule, Compound IV, presented in Scheme 15 hereinabove, was prepared from the iodobenzene Compound 94 as illustrated in Scheme 24 below.

Compound 94 was prepared from the aldehyde Compound 90 as shown in the Scheme 24 below by employing a Pd^II cross-coupling reaction of Compound 90 with TIPS-acetylene using CuI and Et₃N to afford Compound 91, and using TBAF in THF to afford the alkyne Compound 92. The selective Pd^II cross-coupling reaction between Compound 92 and 1,4-diiodobenze afforded Compound 93, which was thereafter converted into a ter-pyridine derivative employing aldol reaction using acetyl pyridine, ammonium hydroxide, and potassium hydroxide in ethanol to afford Compound 94.

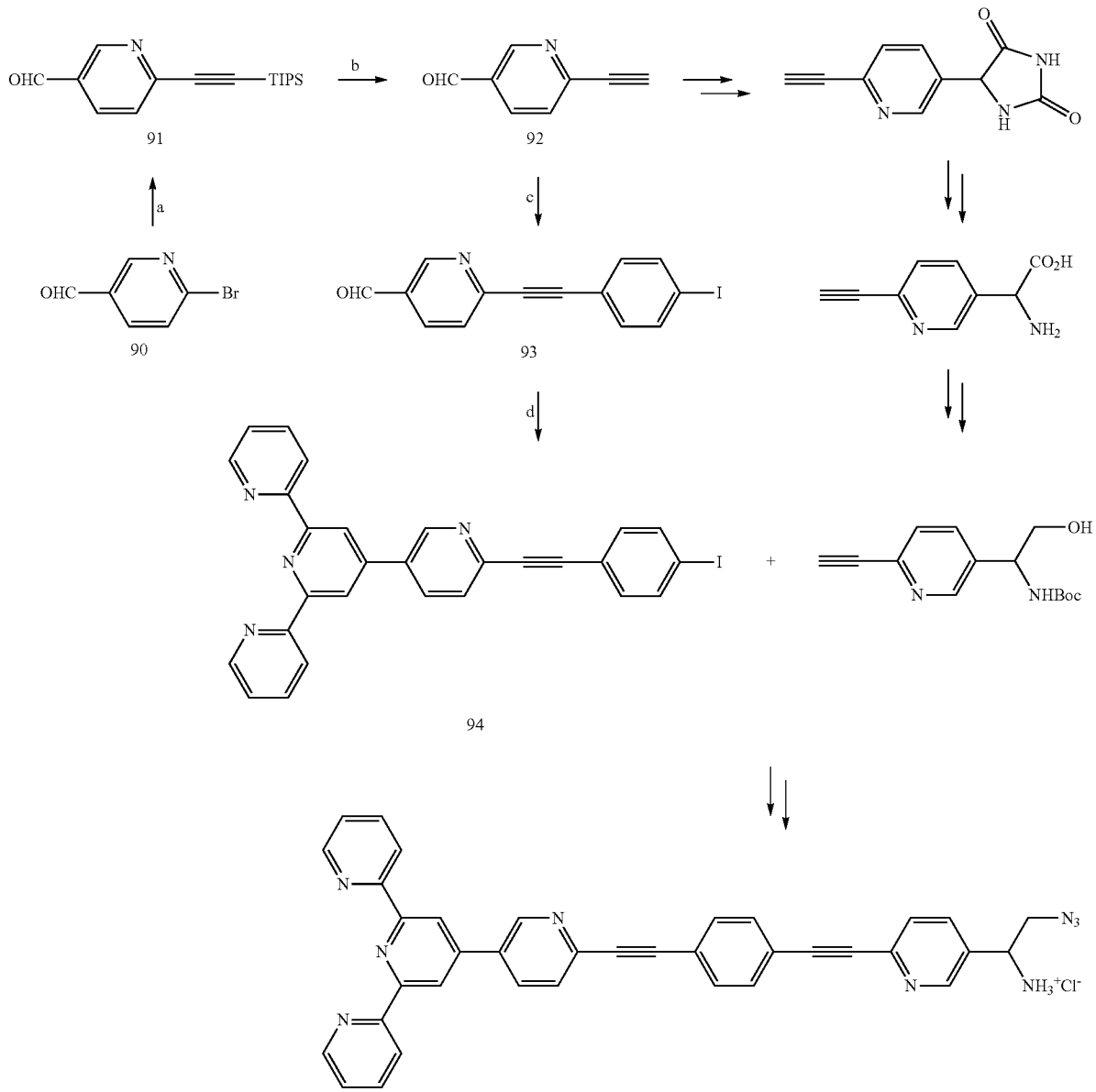

Scheme 24

6-(2-TIPS-ethynyl)pyridine-carboxaldehyde (Compound b, Scheme 24) was prepared from Compound 90 (6-bromopyridine-3-carboxydehyde) using $Pd^{II}$ cross-coupling reaction as described hereinabove with TIPS-acetylene in THF (2 ml/mmol). The residue was purified by chromatography using silica gel and hexane/ethyl acetate (10:1) as eluent to afford TIPS-ethynyl Compound 91 as thick brownish oil (85% yield).

$^1$H NMR (500 MHz, CDCl$_3$) –δ: 10.1 (s, CHO), 9.0 (d, J=2 Hz, 1H), 8.11 (dd, J=8 Hz, 1H), 7.6 (d, J=8 Hz, 1H), 1.18-1.12 (bm, 21H);

$^{13}$C NMR (125 MHz, CDCl$_3$) –δ: 190, 152, 148, 135.6, 130, 128, 105.2, 97.1, 18.6, 11.2;

MS (ESI), m/z: 288 MH$^+$.

6-Ethynylpyridine-3-carboxaldehyde (Compound 92, Scheme 24) was prepared by removing the TIPS protecting group from Compound 91 as described hereinabove. The residue was purified by chromatography using silica gel and hexane/ethyl acetate (3:1) as eluent to afford the ethynyl Compound 92 as white solid (82% yield).

$^1$H NMR (500 MHz, CDCl$_3$) –δ: 10.1 (s, CHO), 9.0 (s, 1H), 8.15 (dd, J=8 Hz, 1H), 7.64 (d, J=8 Hz, 1H), 3.39 (s, 1H);

MS (ESI), m/z: 132 MH$^+$.

6-(2-(4-Iodophenyl)ethynyl)pyridine-3-carboxaldehyde (Compound 93, Scheme 24) was prepared from ethynylpyridine Compound 92 by using $Pd^{II}$ cross-coupling reaction as described hereinabove with 1,4-di-iodobenzene in THF (2 ml, 7 mmol). The residue was purified by chromatography using silica gel and hexane/ethyl acetate (7:3) as eluent to afford the iodophenyl Compound 93 as a brownish solid (70% yield).

$^1$H NMR (500 MHz, CDCl$_3$) –δ: 10.1 (s, CHO), 9.0 (d, J=2 Hz, 1H), 8.17 (dd, J=8 Hz, 1H), 7.74 (d, J=10.5 Hz, 2H), 7.66 (d, J=8.5 Hz, 1H), 7.34 (d, J=8.5 Hz, 2H);

$^{13}$C NMR (125 MHz, CDCl$_3$) –δ: 189.8, 152.3, 148, 137.8, 135.9, 133.6, 129.9, 127.3, 121, 96.2, 92.3, 89.5.

6-(2-(4-Iodophenyl)ethynyl)pyridine-3-ter-pyridine (Compound 94, Scheme 24) was prepared by stirring a mixture of Compound 93 (500 mg, 1.5 mmol), 2-Acetylpyridine (550 mg, 4.5 mmol), KOH 85% (360 mg, 4.5 mmol, and NH$_4$OH 29% (7.5 ml, 6 mmol) in anhydrous ethyl alcohol (25 ml) and reflux for 14 hours. Thereafter the crude solid was collected by filtration, and washed with cold EtOH to produce the ter-pyridine Compound 94 as a brownish solid (65% yield).

$^1$H NMR (500 MHz, CDCl$_3$) –δ: 9.14 (d, J=1.5 Hz, 1H), 8.75-8.74 (m, 4H), 8.68 (d, J=8, 2H), 8.20 (dd, J=8 Hz, 1H), 7.9 (td, J=7.5 Hz, 2 Hz, 2H), 7.74 (d, J=6.5 Hz, 2H), 7.67 (d, J=8.5, 1H), 7.39-7.35 (m, 5H);

$^{13}$C NMR (125 MHz, CDCl$_3$) –δ: 156.3, 155.7, 149.2, 148.8, 146.4, 143.4, 137.6, 137, 134.8, 133.5, 133.3, 127.2, 124.1, 121.6, 121.4, 118.5, 95.4, 89.8, 89.6;

MS (ESI), m/z: 537 MH$^+$, 559 MNa$^+$.

Other various synthetic steps presented in Scheme 24 were as follows: a) TIPS-ethylyne, CuI, Pd(PPh$_3$)$_2$Cl$_2$, Et$_3$N, THF, 50° C., 16 h, 85% yield; b) TBAF (1 M in THF), THF, –78° C., 1 hour, 82% yield; c) 1,4-Diiodo-benzene, CuI, Pd(PPh$_3$)$_2$Cl$_2$, Et$_3$N, THF, 50° C., 10 h, 70% yield; d) 2-Acetylpyridine, NH$_4$OH, KOH, EtOH, reflux, 14 hours, 65% yield.

Construction of CB[6] Based Rotaxanes Using 1,3-Dipolar Cycloaddition 1,3-dipolar cycloaddition between a bulky aromatic azide derivative and a bulky aromatic alkynyl derivative is employed to construct a guest molecules inside the core of CB[6], as presented in Scheme 14 hereinabove, using CB[6], Compound 95 and Compound 96, as illustrated in Scheme 25 below.

A ternary Complex 97 comprising the azide Compound 95, the alkynyl Compound 96, and CB[6] Compound 1, is formed when the ammonium groups of Compound 95 and Compound 96 bind to the carbonyl oxygen rims of CB[6]. The reaction, conducted in water at 60° C. for 48 hours, proceeds through the transition state (TS) to the product Complex 98, where the product of the cycloaddition occupies the inner void of the CB[6] even at high pH due to the bulky groups. This complex can dissolve in water, DMSO, DMF, methanol and ethanol.

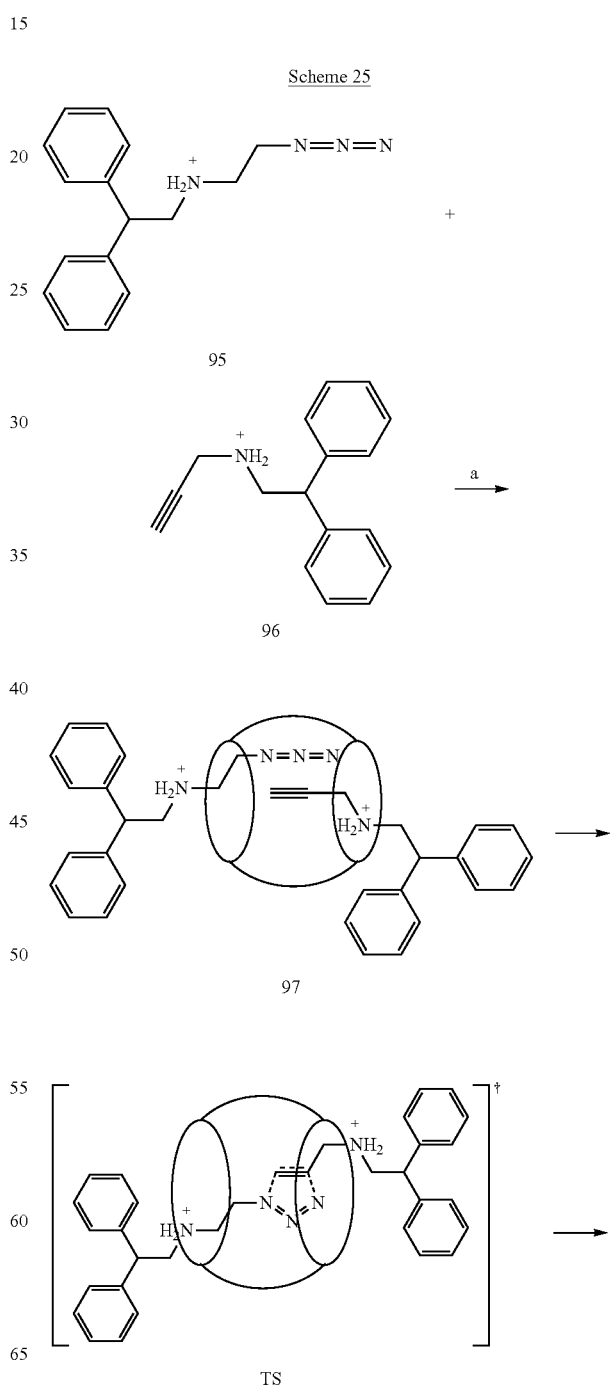

Scheme 25

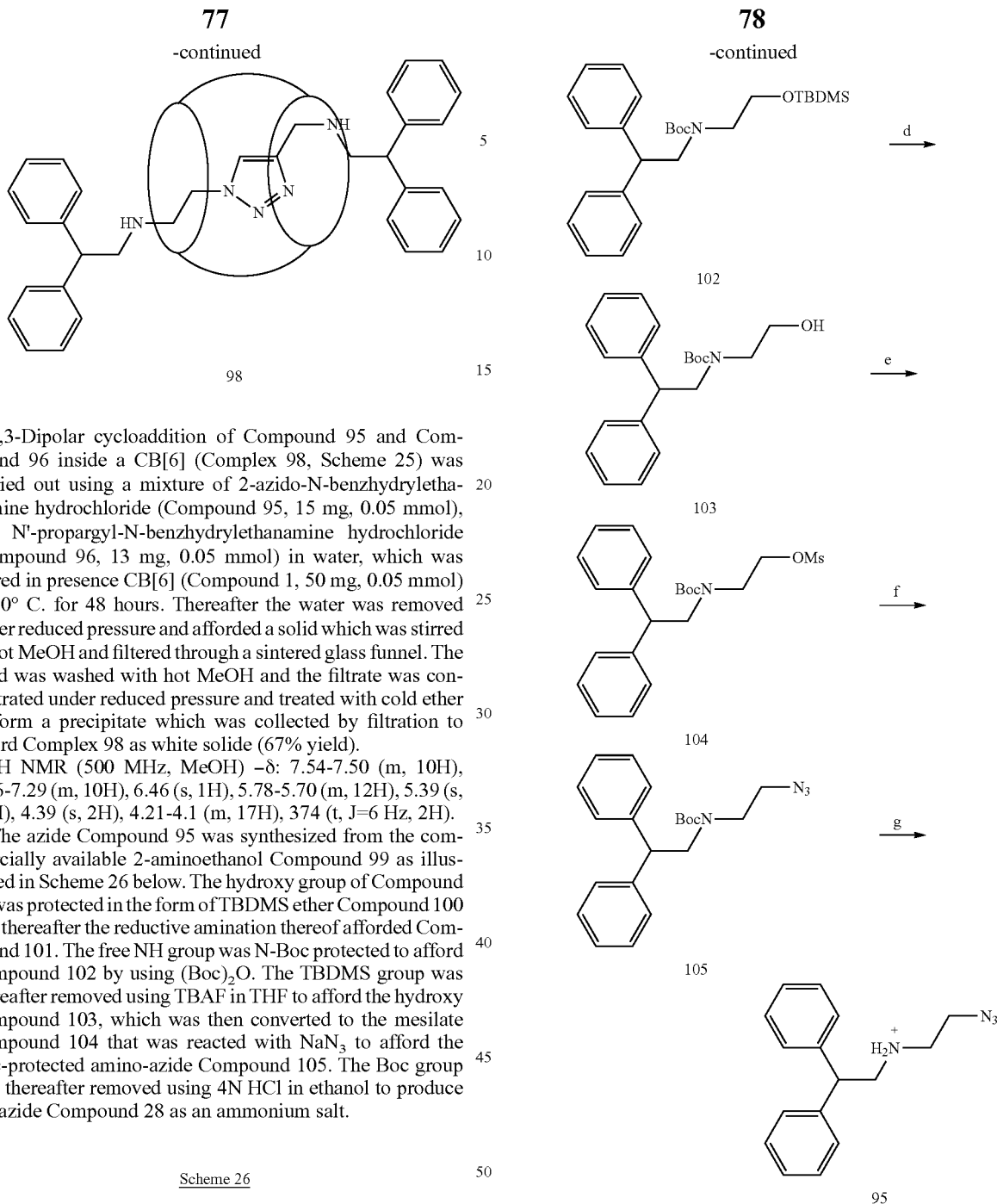

1,3-Dipolar cycloaddition of Compound 95 and Compound 96 inside a CB[6] (Complex 98, Scheme 25) was carried out using a mixture of 2-azido-N-benzhydrylethanamine hydrochloride (Compound 95, 15 mg, 0.05 mmol), and N'-propargyl-N-benzhydrylethanamine hydrochloride (Compound 96, 13 mg, 0.05 mmol) in water, which was stirred in presence CB[6] (Compound 1, 50 mg, 0.05 mmol) at 50° C. for 48 hours. Thereafter the water was removed under reduced pressure and afforded a solid which was stirred in hot MeOH and filtered through a sintered glass funnel. The solid was washed with hot MeOH and the filtrate was concentrated under reduced pressure and treated with cold ether to form a precipitate which was collected by filtration to afford Complex 98 as white solide (67% yield).

$^1$H NMR (500 MHz, MeOH) −δ: 7.54-7.50 (m, 10H), 7.36-7.29 (m, 10H), 6.46 (s, 1H), 5.78-5.70 (m, 12H), 5.39 (s, 12H), 4.39 (s, 2H), 4.21-4.1 (m, 17H), 374 (t, J=6 Hz, 2H).

The azide Compound 95 was synthesized from the commercially available 2-aminoethanol Compound 99 as illustrated in Scheme 26 below. The hydroxy group of Compound 99 was protected in the form of TBDMS ether Compound 100 and thereafter the reductive amination thereof afforded Compound 101. The free NH group was N-Boc protected to afford Compound 102 by using (Boc)$_2$O. The TBDMS group was thereafter removed using TBAF in THF to afford the hydroxy Compound 103, which was then converted to the mesilate Compound 104 that was reacted with NaN$_3$ to afford the Boc-protected amino-azide Compound 105. The Boc group was thereafter removed using 4N HCl in ethanol to produce the azide Compound 28 as an ammonium salt.

Scheme 26

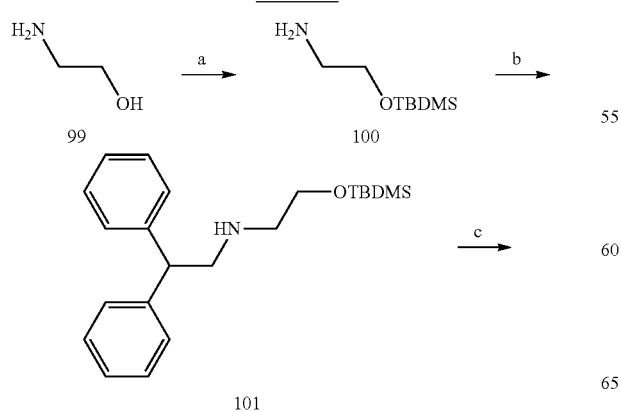

1-tert-Butyldimethylsilyloxy-2-amino ethane (Compound 100, Scheme 26) was prepared using TBSC1 (2.7 grams, 18.1 mmol) which was added to a stirred solution of 2-amino ethanol (Compound 99) (1 grams, 16.5 mmol), triethylamine (3.5 ml, 24.8 mmol), and DMAP (20 mg) in dry CH$_2$Cl$_2$ (30 ml). The reaction mixture was stirred overnight at room temperature and upon completion of the reaction as indicated by TLC, the reaction mixture was quenched with aqueous NH$_4$Cl, extracted with CH$_2$Cl$_2$, the combined organic layer was washed with water and dried over MgSO$_4$, and the solvents were removed under reduced pressure to afford Compound 100 as yellowish oil (2.8 grams, 96% yield).

$^1$H NMR (500 MHz, CDCl$_3$) −δ: 3.6 (t, J=5.5 Hz, 2H), 2.74 (t, J=5.5 Hz, 2H), 0.87 (s, 9H), 0.04 (s, 6H).

2-tert-Butyldimethylsilyloxy-N-benzhydrylethanamine (Compound 101, Scheme 26) was prepared using a mixture of di-phenyl acetaldehyde (Compound 106, 1.25 grams, 6.4 mmol), amino-ethane Compound 100 (1.35 grams, 7.7 mmol), AcOH (0.4 grams 6.4 mmol), sodium triacetoxy borohydride (4 grams, 19.2 mmol) in 1,2 dichloroethane (20 ml), which was stirred for 18 hours. Thereafter the reaction mixture was quenched with aqueous $NH_4Cl$, extracted with ethyl acetate, washed with $NaHCO_3$, brine, dried over $Na_2SO_4$, and the solvents were removed under reduced pressure to afford Compound 101 as white solid (2.1 grams, 91% yield).

$^1$H NMR (500 MHz, $CDCl_3$) –δ: 7.36-7.27 (m, 10H), 4.74 (t, J=8.5 Hz, 1H), 3.87 (t, J=5 Hz, 2H), 3.59 (d, J=8 Hz, 2H), 3.12 (t, J=5 Hz, 2H), 0.74 (s, 9H), 0.03 (s, 6H);

MS (ESI), m/z: 356 $MH^+$.

2-tert-butyldimethylsilyloxy-N'-boc-N-benzhydrylethanamine (Compound 102, Scheme 26) was prepared using a mixture of Compound 101 (2.9 grams, 8.2 mmol), Boc-anhydride (2.1 grams, 9.8 mmol), triethylamine (1.8 ml, 12.3 mmol), and DMAP (80 mg) in $CH_2Cl_2$ (50 ml), which was stirred overnight. Thereafter the resulting residue was purified by column chromatography using silica gel and ethyl acetate:hexane (1:9) as eluent to afford Compound 102 as colorless oil (3.6 grams, 97% yield).

$^1$H NMR (500 MHz, $CDCl_3$) –δ: 7.30-7.19 (m, 10H), 4.44-4.23 (td, J=8, 59 Hz, 1H), 3.93 (t, J=7 Hz, 2H), 3.65-3.50 (td, J=5.5, 62.5 Hz, 2H), 305-2.93 (td, J=5.5, 48.5 Hz, 2H), 1.41 (s, 9H0, 0.88 (s, 9H), 0.03 (s, 6H);

MS (ESI), m/z: 456 $MH^+$, 478 $MNa^+$.

2-Hydroxy-N'-boc-N-benzhydrylethanamine (Compound 103, Scheme 26) was prepared using TBAF (1 M in THF, 6.9 ml, 6.9 mmol) which was added to a solution of Compound 102 (2.6 grams, 2.9 mmol) in dry THF (30 ml) at 0° C. The reaction mixture was stirred for 4 hours at room temperature, and thereafter extracted with $CH_2Cl_2$/water followed by purification using silica gel and hexanes/ethyl acetate (6:4) as eluent to afford Compound 103 as colorless oil (1.8 grams, 93% yield).

$^1$H NMR (500 MHz, $CDCl_3$) –δ: 7.31-7.20 (m, 10H), 4.45-4.44 (m, 1H), 3.88 (d, J=6.5 Hz, 2H), 3.55 (s, 2H), 3.16-3.06 (m, 2H), 1.41 (s, 9H);

MS (ESI), m/z: 364 $MNa^+$.

2-Mesylate-N'-boc-N-benzhydrylethanamine (Compound 104, Scheme 26) was prepared by adding mesylate chloride (0.7 grams, 6.1 mmol) to a stirred solution of Compound 103 (1.7 grams, 5.1 mmol), triethylamine (1.1 ml, 7.7 mmol) in $CH_2Cl_2$ (20 ml) at 0° C., and then stirring the reaction mixture at room temperature for 2 hours. Upon completion of the reaction, as indicated by TLC, the reaction mixture was quenched with aqueous $NH_4Cl$, extracted with $CH_2Cl_2$, washed with water, dried over $MgSO_4$ and the solvent was removed to afford Compound 104 as yellowish oil (1.9 grams, 89% yield).

MS (ESI), m/z: 320 $MH^+$, 342 $MNa^+$.

2-Azido-N'-boc-N-benzhydrylethanamine (Compound 105, Scheme 26) was prepared by using a mixture of Compound 104 (1.9 grams, 4.5 mmol), and $NaN_3$ (360 mg, 5.5 mmol) in DMF (20 ml), which was stirred at 80° C. overnight. Thereafter the reaction mixture was quenched with aqueous $NH_4Cl$ extracted with ethyl ether, washed with brine, dried over $MgSO_4$, and the solvents were removed under reduced pressure to afford Compound 105 (50% yield).

$^1$H NMR (500 MHz, $CDCl_3$) –δ: 7.3-7.21 (m, 10H), 4.41-4.26 (m, 1H), 3.90 (d, J=8 Hz, 2H), 3.26-3.0 (m, 4H), 1.44 (s, 9H);

MS (ESI), m/z: 389 $MNa^+$.

2-Azido-N-benzhydrylethanamine hydrochloride (Compound 95, Scheme 26) was prepared by removing the Boc group from Compound 105 as described hereinabove to afford Compound 95 as white solid.

$^1$H NMR (500 MHz, $D_2O$) –δ: 7.48-7.37 (m, 10H), 4.50 (t, J=8 Hz, 1H), 3.9 (d, J=8 Hz, 2H), 3.77 (t, J=5.5 Hz, 2H), 3.31 (t, J=5.5 Hz, 2H)

MS (ESI), m/z: 267 $MH^+$.

Other synthetic steps presented in Scheme 26 were as follows: a) TBDMSCl, $Et_3N$, $CH_2Cl_2$, room temperature, 14 hours, 95% yield; b) Diphenyl acetaldehyde, Sodium triacetoxy borohydride, 1,2-dichloroethane, room temperature, 14 hours, 90% yiels; c) Boc anhydride, $Et_3N$, $CH_2Cl_2$, room temperature, 24 hours, 80% yield; d) TBAF, THF, room temperature, 2 hours, 93% yield; e) MsCl, $Et_3N$, $CH_2Cl_2$, 0° C., room temperature, 2 hours, 88% yield; f) $NaN_3$, DMF, 80° C., 14 h, 75% yield; g) 4N HCl, EtOH, room temperature, 16 hours, 80% yield.

The alkynyl ammonium salt, Compound 96, was synthesized from the commercially available diphenyl acetaldehade, Compound 106, as shown in Scheme 27 below, by reductive amination to afford Compound 107, which was thereafter converted to the ammonium salt form using 4N HCl in ethanol to afford Compound 96.

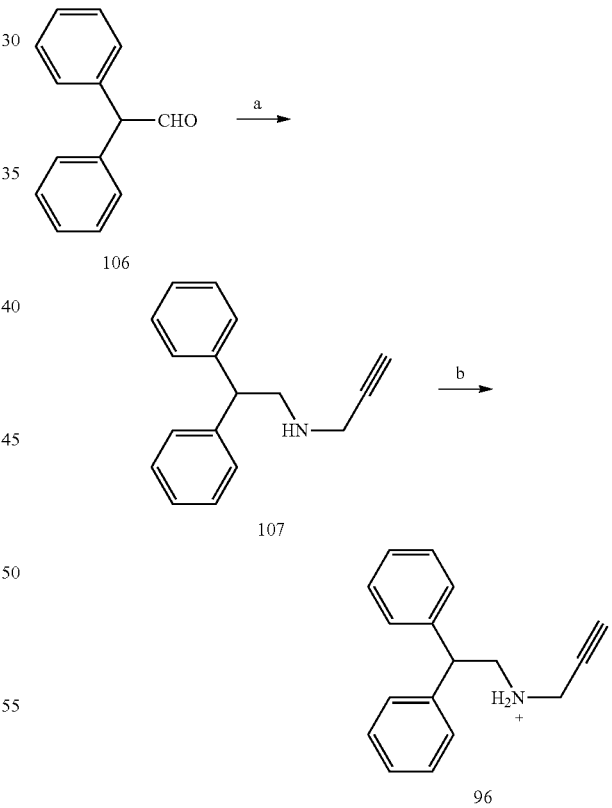

Scheme 27

N'-Propargyl-N-benzhydrylethanamine (Compound 107, Scheme 27) was prepared by using a mixture of diphenyl acetaldehyde (Compound 106, 250 mg, 1.3 mmol), propargyl amine (0.1 ml, 1.5 mmol), 3 Å molecular sieves (500 mg) in MeOH (5 ml), which was stirred for 1 hour at room temperature. Thereafter the reaction mixture was cooled to 0° C. while $NaBH_4$ (76 mg, 2 mmol) was added thereto in one portion. After 3 hours of continuous stirring, the reaction mixture was diluted with water and filtered through a plug of celite in a sintered glass funnel after the addition of five 10 ml portions of cold ethyl ether. The aqueous phase was separated and extracted three times with ether, and the combined organic phases was washed with brine, dried over $MgSO_4$ and the solvent was removed to afford Compound 107 as colorless oil (215 mg, 74% yield).

$^1$H NMR (500 MHz, $CDCl_3$) –δ: 7.34-7.2 (m, 10H), 4.22-4.17 (m, 1H), 3.45 (d, J=1.5 Hz, 2H), 3.34 (d, J=7.5 Hz, 2H), 2.23 (t, J=2 Hz, 1H).

N'-Propargyl-N-benzhydrylethanamine hydrochloride salt (Compound 96, Scheme 27) was prepared from Compound 107 which was converted to the ammonium salt as described hereinabove to afford Compound 96 as white solid.

$^1$H NMR (500 MHz, $D_2O$) –δ: 7.48-7.44 (m, 8H), 7.4-7.37 (m, 2H), 4.48 (t, J=8 Hz, 1H), 3.98-3.96 (m, 4H), 3.0 (t, J=3 Hz, 1H);

MS (ESI-TOF), m/z: 236.1439 MH$^+$.

Other various synthetic steps presented in Scheme 27 were as follows: a) 1.) Propargyl Amine, 3 Å molecular sieves, sodium borohydride, methanol, room temperature, 5 hours, 65% yield; b) 4N HCl, ethanol, room temperature, 2 hours, 80% yield.

Example 3

Isothermal Titration Calorimetry

Isothermal titration calorimetry (ITC) was previously employed to study complexation parameters of Compound 1 [63]. Measurement of the host-guest binding thermodynamic profile using ITC provides in a single experiment not only the binding constants ($K_b$) and binding stoichiometry (n), but also the differences of enthalpy (ΔH) and entropy (ΔS) of binding.

The experiment was carried out by loading the ITC sample cell with saturated aqueous solution of Compound 1 (1.4 ml) and titrating it with a neutral aqueous solution of the dicationic dihydrochloride salts of various exemplary guest molecules at concentrations that ranged from 3.3 mM to 5.0 mM. The heat generated during each injection was recorded (FIG. 1) and the thermodynamic parameters were acquired by non-linear least squares fit of the calorimetric titration data to a one-site binding model (Table 2).

A saturated solution of Compound 1 (0.4 mM) in water at pH=7 was prepared by stirring an excess of finely powdered Compound 1 overnight at 30° C. and filtering through a 100-μm micro-filter. Solutions of the guest molecules at concentrations of 3.3-6 mM, were prepared and filtered through a 100-μm micro-filter as well. Titration calorimetry measurements were performed with a VP-ITC calorimeter (Microcal, Northampton, Mass.) as previously described [86]. Repeat determinations indicated errors of 3-10% in n, ΔH, degree, and K values over the most favorable concentration range. A solution of Compound 1 was titrated by 29 injections of 6 μL of guest molecule solutions at 30° C. each, and the titration data were analyzed using Origin2000 software.

Figure 1B:
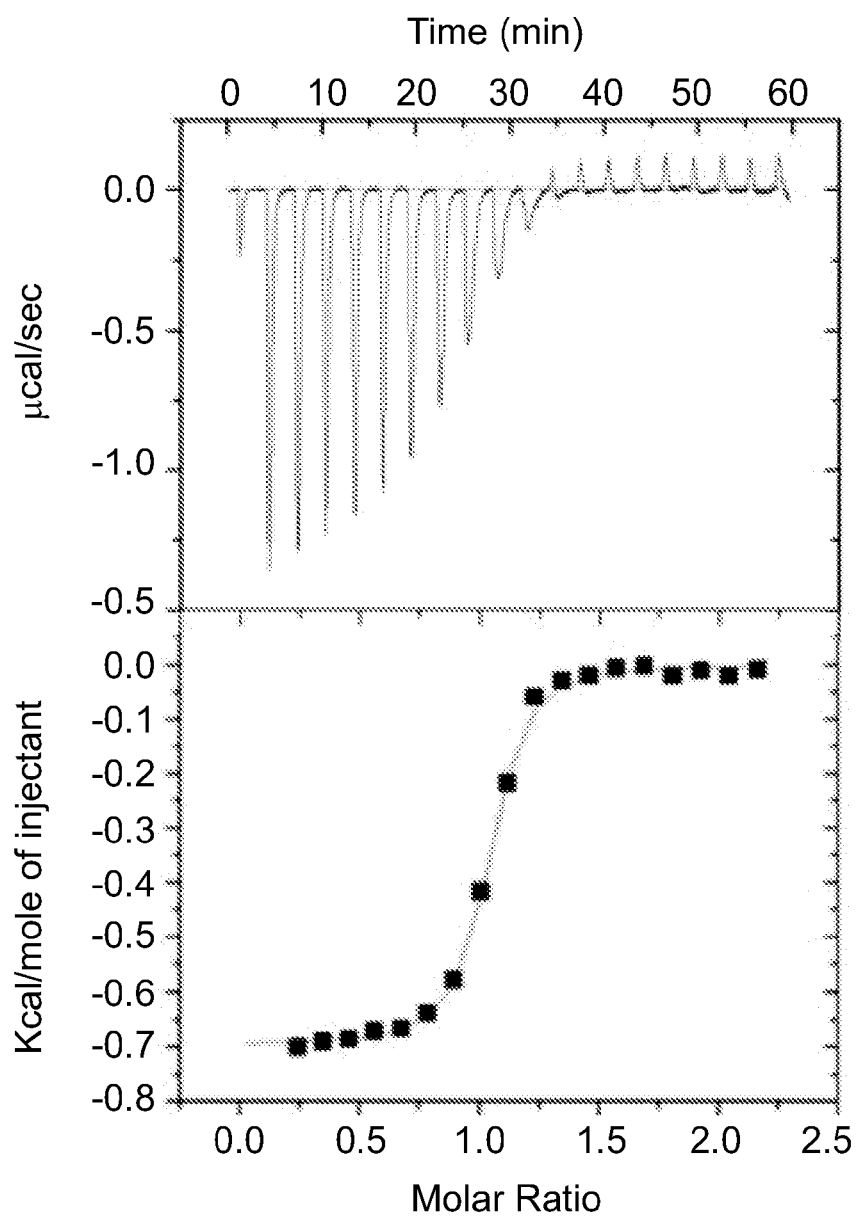
Figure 1C:
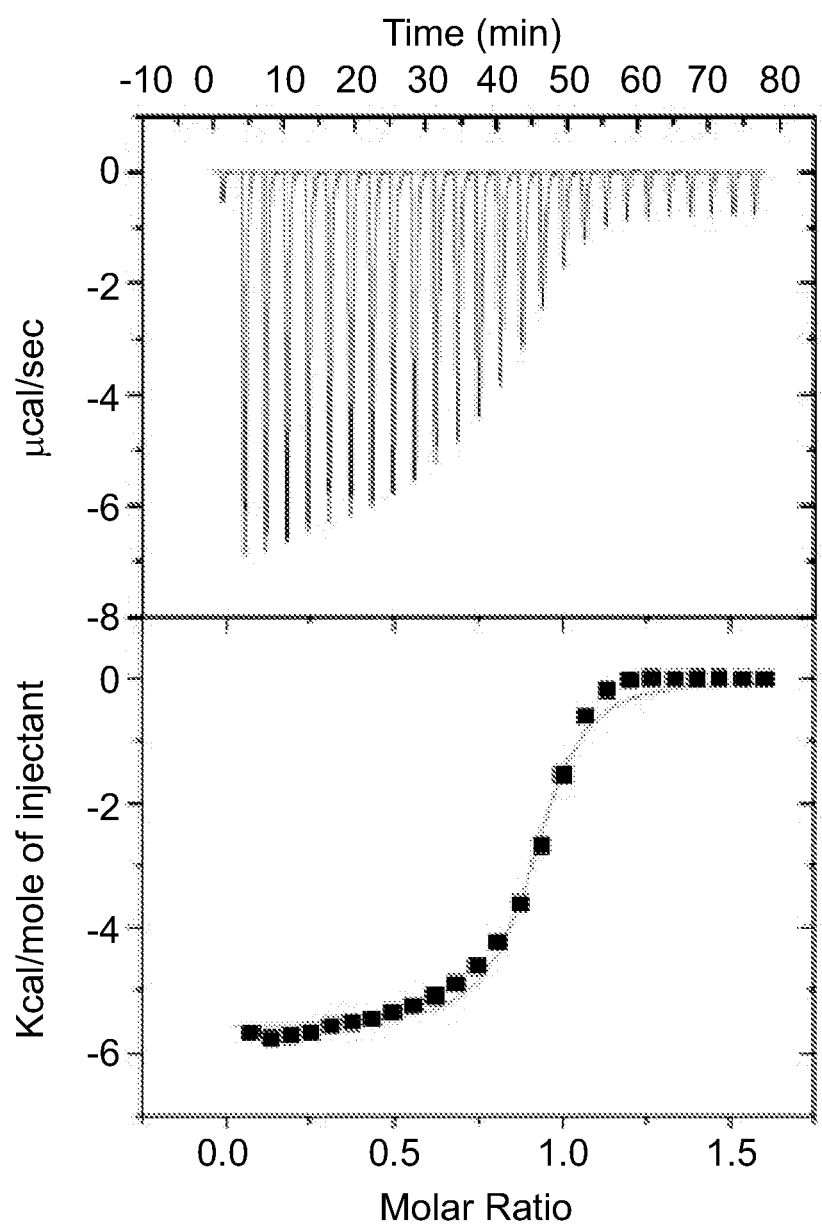
Figure 1D:
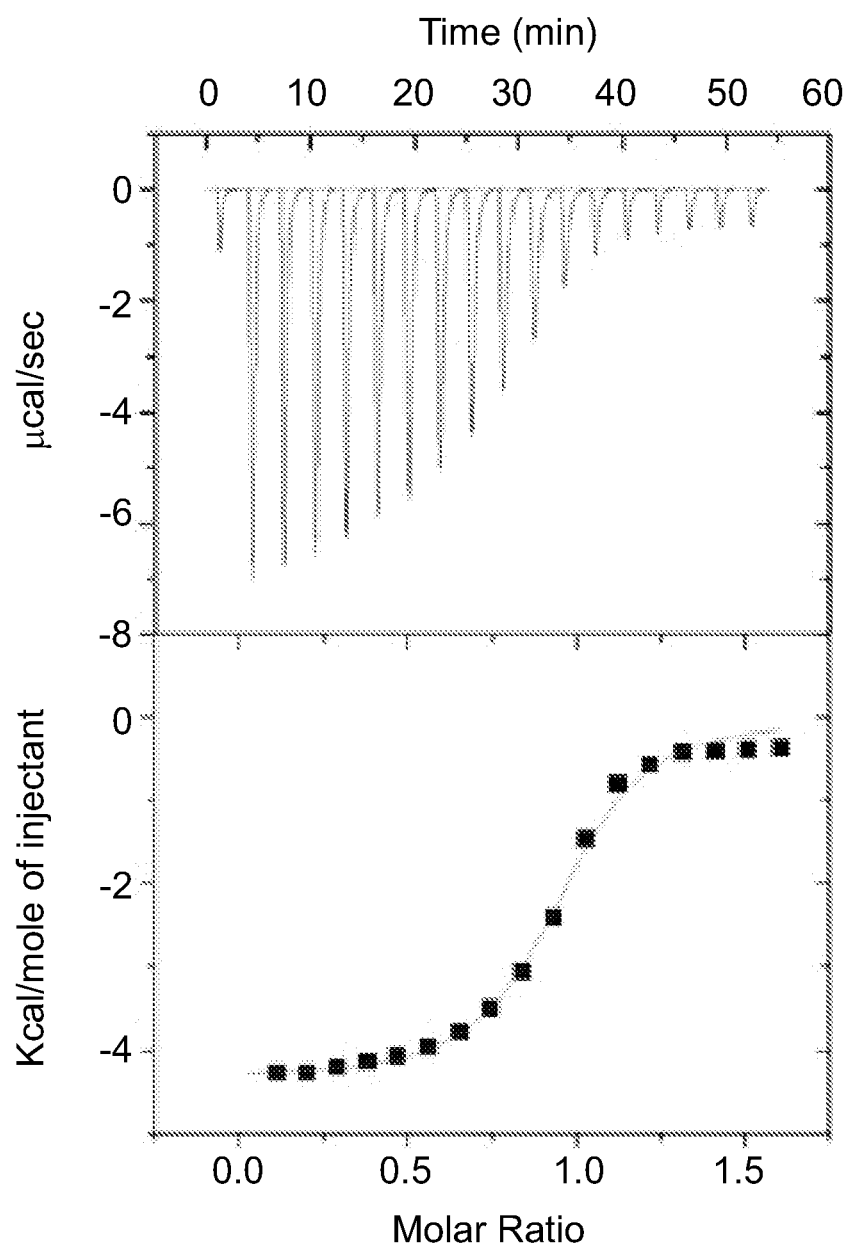

FIG. 1 presents the isothermal titration calorimetry (ITC) curves obtained for Compound 1 (0.4 mM in water) titrated with several exemplary positively charged guest molecules at 30° C., wherein FIG. 1A was obtained by titrating a solution of Compound 3' (3.33 mM), FIG. 1B was obtained by titrating a solution of Compound 4' (6 mM), FIG. 1C was obtained by titrating a solution of Compound 6' (3.3 mM) and FIG. 1D was obtained by titrating a solution of Compound 7' (5.0 mM).

Table 2 presents the results of the ITC experiments, namely the dissociation constants and thermodynamic data for CB[6]—guest complexes, measured in water at 30° C.

TABLE 2

| Guest | $K_d$ (μM) | ΔH (Kcal/mol) | ΔS (cal/mol) |
|---|---|---|---|
| Compound 3' | 3.53 ± 0.30 | −13.760 ± 0.090 | −20.45 |
| Compound 4' | 2.28 ± 0.25 | −0.696 ± 0.005 | 23.51 |
| Compound 5' | 6.80 ± 0.87 | −4.452 ± 0.057 | 9.29 |
| Compound 6' | 3.36 ± 0.56 | −3.718 ± 0.044 | 12.78 |

As can be seen in Table 2, although all four guest molecules exhibited similar dissociation constants within the range of 2-7 μM, their ΔH and ΔS of binding vary significantly. The significant gain of binding enthalpy in the case of Compound 3', in comparison with the smaller gains in the cases of Compounds 4', 6', and 7', is counterbalanced by the large negative entropy term of Compound 3' (ΔS=−85.77 J/mol.° K), as compared with the positive terms of Compounds 4', 6', and 7' (ΔS=98–39 J/mol.° K). Apparently, complexation of Compound 3' requires freezing multiple rotational and vibrational degrees of freedom, resulting in a large entropy penalty, which is not the case with the rigid guest molecules, Compounds 4', 6', and 7'.

The comparison between Compounds 3' and 4' is of particular interest because both guest molecules have two ammonium groups separated by a chain of six carbon atoms, yet their binding enthalpies are dramatically different (ΔH=−57.57 and −0.2.91 KJ/mol, respectively). It is postulated that this difference to result from a strong hydrophobic interaction between the hexamethylene chain of Compound 3' and the interior of Compound 1, which adds to the attractive interaction between the ammonium groups and the polar oculi of Compound 1. In the case of Compound 4', however, the interaction between the diyne rod and the interior of Compound 1 is assumed to be repulsive, resulting in a very small net enthalpy gain.

Example 4

Solid-State X-Ray Structures of Insertion Complexes

Further support to the underlying assumption of the special interaction between CB[n] and guest molecules based on bis-ammonium dialkynyl threading moieties was obtained using solid state X-ray crystallography. The experiments were conducted in order to verify that a polyalynyl (dialkynyl) threading moiety will position itself in the middle of the cucurbituril inner void regardless of the spatial position of the positively charged group attached to each of its ends, particularly when these are positioned away from the longitudinal-axis thereof.

Several exemplary insertion complexes were prepared as described hereinabove by adding Compound 1 to aqueous solutions of exemplary dicationic-dialkynyl salts, namely Compound 4', Compound 5', Compound 7', Compound 4 and Compound 8 to afford the corresponding Complex 4', Complex 5', Complex 7', Complex 4 and Complex 8 respectively. Formation of stable complexes was evident from their $^1$H NMR spectra as well as the MS (MALDI-TOF) data. All complexes were crystallized from the aqueous solution over 2-3 weeks and a single crystal was studied by X-ray crystallography.

Figure 2:
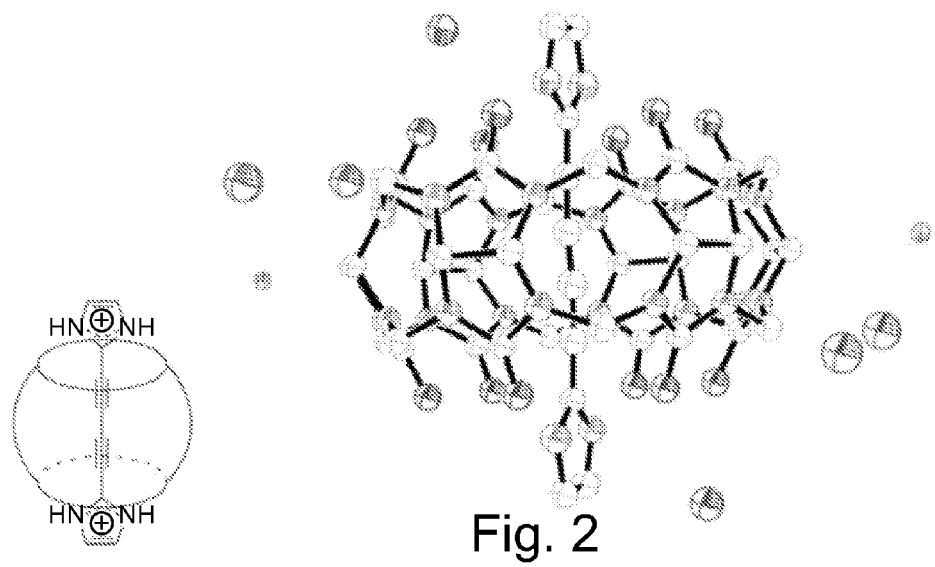
FIG. 2 presents an illustration of the crystal structure of an exemplary host-guest insertion complex according to some embodiments of the present invention, Complex 4a, featuring a bis-imidazole dialkyne (Compound 4) inserted in a CB[6] (Compound 1), showing the centrosymmetric positioning of the guest molecule inside the cucurbituril host in a top view and a side view of the complex (a schematic molecular illustration of the complex is added for clarity).

FIG. 2 presents a schematic illustration of the crystal structure of an exemplary host-guest insertion complex according to some embodiments of the present invention, Complex 4a, featuring a bis-imidazole dialkyne (Compound 4) inserted in a CB[6] (Compound 1), showing the centrosymmetric positioning of the guest molecule inside the cucurbituril host.

Figure 3:
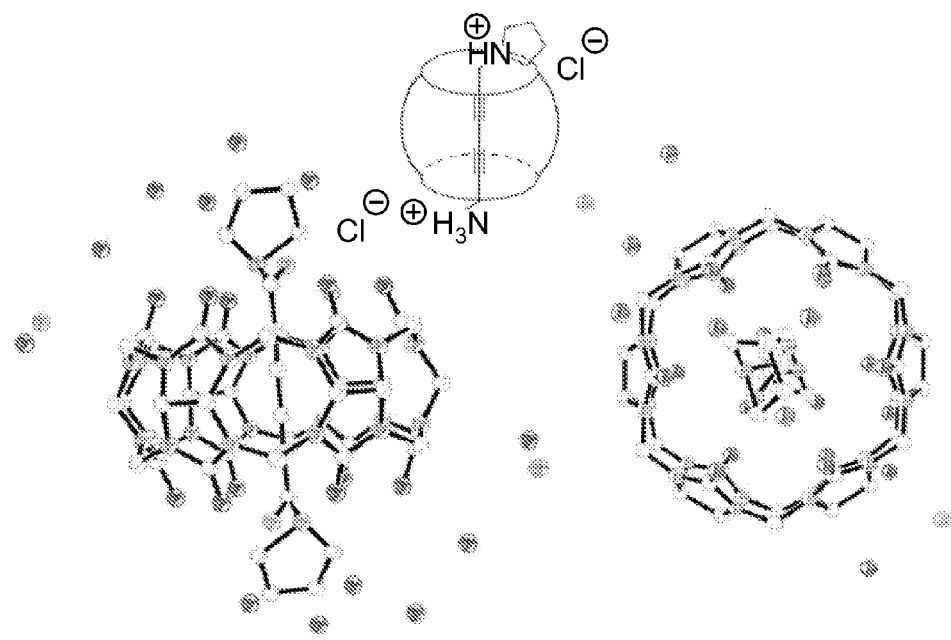
FIG. 3 presents an illustration of the crystal structure of an exemplary host-guest insertion complex according to some embodiments of the present invention, Complex 5', featuring N-6-pyrrolidinium-hexa-2,4-diynyl ammonium dichloride (Compound 5') inserted in a CB[6] (Compound 1), showing the centrosymmetric positioning of the guest molecule inside the cucurbituril host in a top view and a side view of the complex (a schematic molecular illustration of the complex is added for clarity).

FIG. 3 presents a schematic illustration of the crystal structure of an exemplary host-guest insertion complex according to some embodiments of the present invention, Complex 5', featuring N-6-pyrrolidinium-hexa-2,4-diynyl ammonium dichloride (Compound 5') inserted in a CB[6] (Compound 1).

As can be seen in FIG. 3, Complex 5' exhibits a centrosymmetric disordered structure with the dialkyne rod floating at the centre of the macrocyclic host with the unit cell containing two such complexes. The crystallographic data indicated that two chloride counteranions and nine water molecules, all interconnected by hydrogen bonds, are associated with each complex. The complex is located on an inversion center at unit cell position (0, 0, ½) but the ligand is disordered between two sites, with the pyrrolidinium and ammonium groups sharing both sites with 50% occupancy, thus forming an average centrosymmetric species. Each site at the CB oculi is occupied by either a pyrrolidinium ring (50%) or by an ammonium group accompanied by three hydrogen-bonded water molecules (altogether 50%). Only one hydrogen bond is formed between the pyrrolidinium nitrogen and the carbonyl oxygen of Compound 1 whereas the ammonium nitrogen creates one hydrogen bond with carbonyl oxygen of Compound 1 and two bonds with water molecules. There are water hydrogen bonds network that connects between water, carbonyl oxygens and anions.

Figure 4:
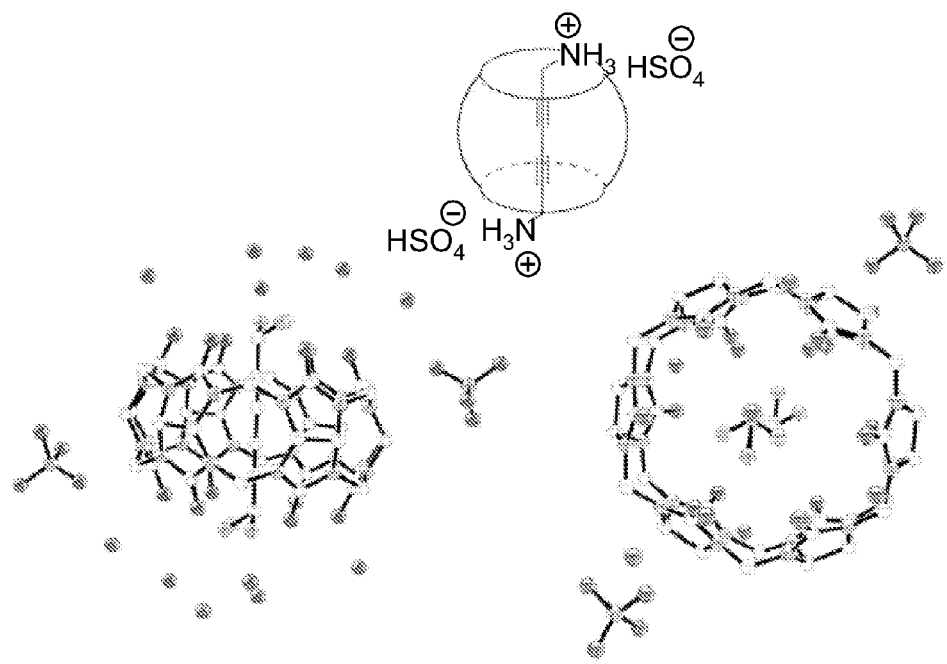
FIG. 4 presents an illustration of the crystal structure of an exemplary host-guest insertion complex according to some embodiments of the present invention, Complex 4', featuring Hexa-2,4-diyne-1,6-diammonium dihydrochloride salt (Compound 4') inserted in a CB[6] (Compound 1), showing the centrosymmetric positioning of the guest molecule inside the cucurbituril host in a top view and a side view of the complex (a schematic molecular illustration of the complex is added for clarity).

FIG. 4 presents a schematic illustration of the crystal structure of an exemplary host-guest insertion complex according to some embodiments of the present invention, Complex 4', featuring Hexa-2,4-diyne-1,6-diammonium dihydrochloride salt (Compound 4') inserted in a CB[6] (Compound 1).

As can be seen in FIG. 4, the crystal structure of Complex 4' exhibits a centrosymmetric structure with the unit cell containing one complex, twelve water molecules and two $HSO_4^-$ counteranions. The crystallographic data indicated that the complex is situated on an inversion center at unit cell position (½, ½, ½). The ammonium groups take up three different positions with corresponding occupancies of 0.50, 0.25 and 0.25. This observation of atomic disorder is attributed to the facile rotation around the guest longitudinal-axis. In any of the three positions the nitrogen atom forms hydrogen bonds with two water molecules and with four carbonyl oxygens at the oculi of Compound 1. Additional hydrogen bonds exist between water molecules and the $HSO_4^-$ oxygens. Most importantly, the diacetylene rod floats at the center of the macrocyclic host with no apparent van der Waals interactions therebetween. The existence of multiple rotamers with similar energy and similar steric demands suggests that rotation of the polyyne rotor within the CB stator is quite facile. Apparently, this motion is restricted in the solid state due to the fixed position of the counteranions and the network of hydrogen bonds that includes all water molecules, counteranions and ammonium cations.

Figure 5:
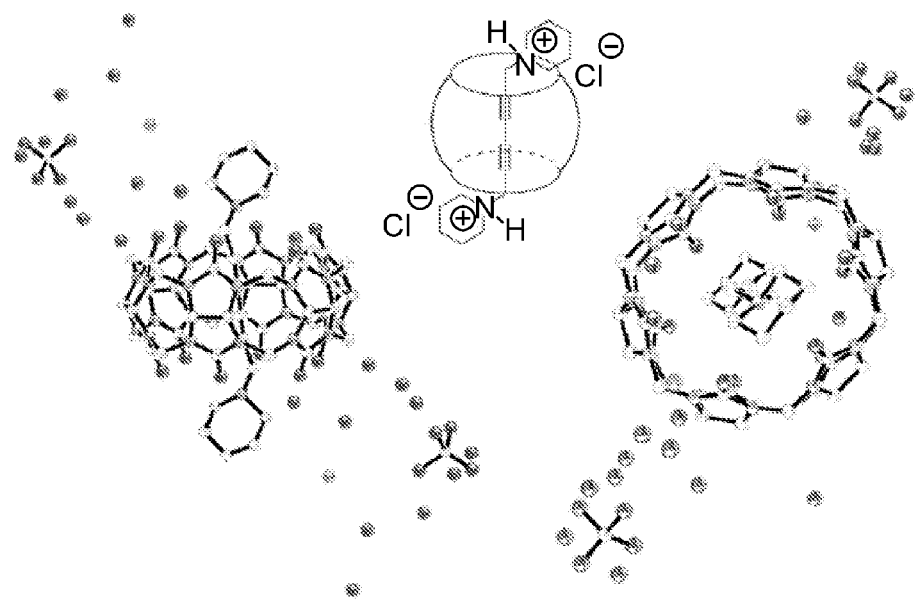
FIG. 5 presents an illustration of the crystal structure of an exemplary host-guest insertion complex according to some embodiments of the present invention, Complex 7', featuring 1,6-Dipiperidinium-2,4-hexadiyne dichloride salt (Compound 7') inserted in a CB[6] (Compound 1), showing the centrosymmetric positioning of the guest molecule inside the cucurbituril host in a top view and a side view of the complex (a schematic molecular illustration of the complex is added for clarity).
Figure 6:
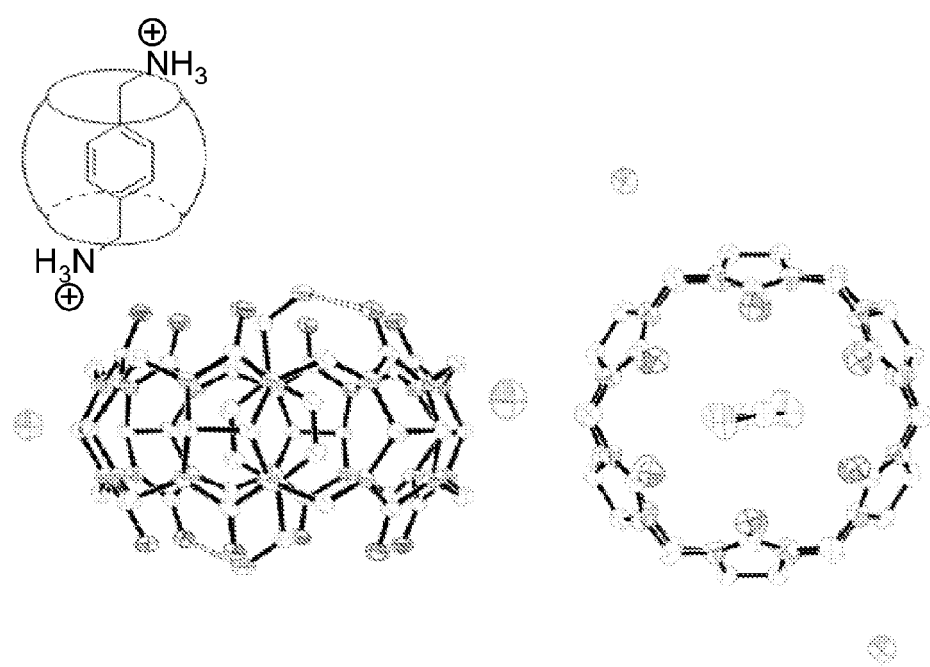
FIG. 6 presents an illustration of the crystal structure of an exemplary host-guest insertion complex according to some embodiments of the present invention, Complex 8, featuring p-xylylenediamine dihydrochloride (Compound 8) inserted in a CB[6] (Compound 1), showing the centrosymmetric positioning of the guest molecule inside the cucurbituril host in a top view and a side view of the complex (a schematic molecular illustration of the complex is added for clarity).

FIG. 5 presents a schematic illustration of the crystal structure of an exemplary host-guest insertion complex according to some embodiments of the present invention, Complex 7', featuring 1,6-Dipiperidinium-2,4-hexadiyne dichloride salt (Compound 7') inserted in a CB[6] (Compound 1).

As can be seen in FIG. 5, the crystal structure of Complex 7' contains two complexes in a unit cell. The asymmetric unit contains two complex unit halves A and B located on inversion centers at (1, ½, 0) and (½, 0, ½) respectively, one $HSO_4^-$ and one $Cl^-$ counteranions and nine molecules of water. Compound 7' is inserted in the cavity of Compound 1 with its piperidinium nitrogen hydrogen forming bonding to one of the carbonyl oxygens. Compound 7' takes only one rotational position inside the CB cavity for both A and B halves but binding differs with respect to the hydrogen bonds to the carbonyl oxygens of the CB oculi. Several carbonyl oxygens are hydrogen bonded to water molecules. In addition, there is a network of hydrogen bonded water molecules that includes the counteranions. Within the unit cell, the guest's axes in the complex molecules of type A or B are aligned in parallel through the inversion centers of the cell.

FIG. 3 presents a schematic illustration of the crystal structure of an exemplary host-guest insertion complex according to some embodiments of the present invention, Complex 8, featuring p-xylylenediamine dihydrochloride (Compound 8) inserted in a CB[6] (Compound 1).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED BY NUMERALS

Other References are Cited in the Text

1. Berg, J. M., et al., *Molecular Motors*, in *Biochemistry*. 2006, W.H. Freeman: New York.
2. Berg, H. C., Annu Rev Biochem, 2003. 72: p. 19-54.
3. Yasuda, R., et al., J Bioenerg Biomembr, 1997. 29(3): p. 207-9.
4. Boyer, P. D., 1998. 37: p. 2297-2307.
5. Kinosita, K., Jr., et al., Cell, 1998. 93(1): p. 21-4.
6. VanBuren, P., et al., Biophys J, 1995. 68(4 Suppl): p. 256S-258S; 258S-259S.
7. Kim, D. E., et al., J Mol Biol, 2002. 321(5): p. 807-19.
8. Davis, A. P., Nature, 1999. 401(6749): p. 120-1.
9. Kelly, T. R., Angew Chem Int Ed Engl, 2005. 44(27): p. 4124-7.
10. Vicario, J., et al., Chem Commun (Camb), 2005(31): p. 3936-8.
11. Crowley, J. D., et al., Chemistry, 2006. 12(35): p. 8935-51.
12. Kay, E. R., et al., Angew Chem Int Ed Engl, 2007. 46(1-2): p. 72-191.
13. Ugi, I., et al., Acc. Chem. Res., 1971.4: p. 288-296.
14. Gust, D., et al., Proc Natl Acad Sci USA, 1973. 70(12 Pt 1-2): p. 3445-3449.
15. Finocchiaro, P., et al., J. Am. Chem. Soc., 1974. 96: p. 3198-3205.
16. Finocchiaro, P., et al., J. Am. Chem. Soc., 1974. 96: p. 3205-3213.

17. Mislow, K., Acc. Chem. Res., 1976. 9: p. 26-33.
18. Cozzi, F., et al., J. Am. Chem. Soc., 1981. 103: p. 957-958.
19. Johnson, C. A., et al., J. Am. Chem. Soc., 1981. 103: p. 6240-6242.
20. Kawada, Y. I. H., J. Am. Chem. Soc., 1981. 103: p. 958-960.
21. Bedard, T. C., et al., J. Am. Chem. Soc., 1995. 117: p. 10662-10671.
22. Vacek, J., et al., New J. Chem., 1997. 21: p. 1259.
23. Clayden, J., et al., Angew. Chem., Int. Ed., 1998. 37: p. 1937-1939.
24. Gimzewski, J. K., et al., Science, 1998. 281(5376): p. 531-3.
25. Sauvage, J.-P., 99, 2001. Special issue.
26. Vacek, J., et al., Proc Natl Acad Sci USA, 2001. 98(10): p. 5481-6.
27. Michl, J., et al., Proc Natl Acad Sci USA, 2002. 99(8): p. 4788-92.
28. Godinez, C. E., et al., J. Am. Chem. Soc., 2002. 124: p. 4701-4707.
29. Horinek, D., et al., Proc Natl Acad Sci USA, 2005. 102(40): p. 14175-80.
30. Karlen, S. D., et al., Organic Letters, 2006. 8: p. 3417-3420.
31. Wang, L., et al., Angew. Chem. Int. Ed. Eng., 2006. 45: p. 4372-4375.
32. Khuong, T.-A. V., et al., J. Am. Chem. Soc., 2007. 129: p. 839-845.
33. Vacek, J., et al., Adv. Functional Mat., 2007. 17: p. 730-739.
34. Schalley, C. A., et al., Acc Chem Res, 2001. 34(6): p. 465-76.
35. Leigh, D. A., et al., Nature, 2003. 424(6945): p. 174-9.
36. Koumura, N., et al., Nature, 1999. 401(6749): p. 152-5.
37. Fletcher, S. P., et al., Science, 2005. 310(5745): p. 80-2.
38. van Delden, R. A., et al., Nature, 2005. 437(7063): p. 1337-40.
39. Kelly, T. R., et al., Nature, 1999. 401(6749): p. 150-2.
40. Kelly, T. R., et al., Am. Chem. Soc., 2000. 122: p. 6935.
41. Bermudez, V. V., et al., Nature, 2000. 406(6796): p. 608-11.
42. Vicario, J., et al., Chem Commun (Camb), 2005(47): p. 5910-2.
43. Vicario, J., et al., J Am Chem Soc, 2006. 128(15): p. 5127-35.
44. Morin, J. F., et al., Org Lett, 2006. 8(8): p. 1713-6.
45. Schill, G., *Catenanes, Rotaxanes, and Knots*. 1971, New York: Academic Press.
46. Felder, T., et al., Highlights in Bioorg. Chem., 2004: p. 526-539.
47. Carella, A., et al., Dalton Trans., 2007: p. 177-86.
48. Saha, S., et al., Chem. Soc. Rev., 2007. 36: p. 77-92.
49. Leigh, D. A., et al., Angew. Chem., Int. Ed., 2000. 39: p. 350-353.
50. Livoreil, A. S., et al., J. Am. Chem. Soc., 1994. 116: p. 9399-9400.
51. Benniston, A. C., Chem. Soc. Rev., 1996. 25: p. 427-437.
52. Livoreil, A. S., et al., J. Am. Chem. Soc., 1997. 119: p. 12114-12124.
53. Ashton, P. R., et al., J. Am. Chem. Soc., 1998. 120: p. 11190-11191.
54. Brouwer, A. M., et al., Science, 2001. 291(5511): p. 2124-8.
55. Behrend, R., et al., Jus. Lieb. Annal Chem., 1905. 339: p. 1-37.
56. Mock, W. L., Top. Curr. Chem., 1995. 175: p. 1-24.
57. Gerasko, O. A., et al., Russ. Chem. Rev., 2002. 71(9): p. 741-760.
58. Kim, K., Chem Soc Rev, 2002. 31(2): p. 96-107.
59. Lee, J. W., et al., Acc Chem Res, 2003. 36(8): p. 621-30.
60. Lagona, J., et al., Angew Chem Int Ed Engl, 2005. 44(31): p. 4844-70.
61. Freeman, W. A., et al., J. Am. Chem. Soc., 1981. 103(24): p. 7367-7368.
62. Fujiwara, H., et al., Bull. Chem. Soc. Jpn., 1987. 60: p. 3891-4.
63. Buschmann, H.-J., et al., Thermochim. Acta, 2000. 346: p. 33-36.
64. Izatt, R. M., et al., J. Am. Chem. Soc., 1976. 98: p. 7620-6.
65. Buschmann, H.-J., et al., Inorg. Chim. Acta, 1992. 193: p. 93-97.
66. Hoffmann, R., et al., J. Chem. Soc. Faraday Trans., 1994. 90: p. 1507.
67. Buschmann, H.-J., et al., J. Sol. Chem., 1998. 27: p. 135-140.
68. Zhang, G.-L., et al., Wuji Huaxue Xuebao 2003. 19: p. 655-659.
69. Mock, W. L., et al., J. Org. Chem., 1986. 51(23): p. 4440-6.
70. Buschmann, H.-J., et al., J. Incl. Phenom., 2006. 54: p. 85.
71. Buschmann, H.-J., et al., Acta Chim. Slov., 1999. 46(3): p. 405-411.
72. Jansen, K., et al., Thermochim. Acta, 2002. 385(1-2): p. 177-184.
73. Sindelar, V., et al., Chem. Commun., 2006(20): p. 2185-2187.
74. Kimoon, K., *Self-Assembly of Interlocked Structures with Cucurbituril, Metal Ions and Metal Complexes*, in *Perspectives in Supramolecular Chemistry*, S. Jean-Pierre, Editor. 2007. p. 371-402.
75. Sindelar, V., et al., Advanced Functional Materials, 2007. 17(5): p. 694-701.
76. Gerber, P. R., et al., J Comput Aided Mol Des, 1995. 9(3): p. 251-68.
77. Gerber, P. R., J Comput Aided Mol Des, 1998. 12(1): p. 37-51.
78. Jeon, H. B., et al., Biochem Biophys Res Commun, 2003. 304(4): p. 788-94.
79. Cowell, A., et al., J. Am. Chem. Soc., 1980. 102: p. 4193-4198.
80. Alami, M., et al., Tetrahedron Lett., 1996. 37: p. 2763-2766.
81. Dallanoce, C., et al., Bioorg Med Chem, 1999. 7(8): p. 1539-47.
82. Soroka, M., Synthesis 1989: p. 547-548.
83. Biel, J. H., et al., J. Am. Chem. Soc., 1958. 80: p. 4609-4614.
84. Fabiano, E., et al., Synthesis, 1987: p. 190-192.
85. Huisgen, R., *1,3-Dipolar cycloaddition—introduction, survey, mechanism*, in *1,3-Dipolar Cycloaddition Chemistry*, A. Padwa, Editor. 1984, Wiley. p. 1-176.
86. Wiseman, T., et al., Anal. Biochem., 1989(179): p. 131-137.

What is claimed is:

1. A rotaxane comprising a host molecule and a guest molecule, said host molecule being a cucurbit[n]uril (CB[n]), and said guest molecule having the general Formula I:

$$U-B_1-L_1-[A]_m-L_2-B_2-Y \qquad \text{Formula I}$$

wherein:

n is an integer that ranges from 5 to 20;

$B_1$ and $B_2$ are each independently an uncharged stopper moiety;

$L_1$ and $L_2$ are each independently an uncharged linking moiety or absent;

$[A]_m$ is a linear and rigid threading moiety having a neutral net charge at a pH that ranges from 6-8;

whereas A is selected from the group consisting of a 1,2-ethyn-di-yl, substituted or unsubstituted cyclobuta-1,3-diene-1,3-di-yl, substituted or unsubstituted pentalene-2,5-di-yl, substituted or unsubstituted pyrene-2,7-di-yl, C-substituted or unsubstituted pyridine-2,5-di-yl, C-substituted or unsubstituted pyrimidine-2,5-di-yl, C-substituted or unsubstituted pyrazine-3,6-di-yl and 1,2,4,5-tetrazine-3,6-diyl, and m is an integer that ranges from 1 to 50; and U and Y are each independently selected from the group consisting of an anchoring group, an effector moiety, a detectible moiety, a biomolecule, or absent.

2. The rotaxane of claim 1, wherein n ranges from 5 to 8.

3. The rotaxane of claim 1, wherein A is a 1,2-ethyn-di-yl.

4. The rotaxane of claim 1, wherein said stopper moiety is selected from the group consisting of a branched alkyl moiety, a branched cycloalkyl moiety, a branched heteroalicyclic moiety, a branched polyaryl moiety, a branched polyheteroaryl moiety, an adamantly moiety, a branched organophosphorous, a branched organoboron, a branched organosilicon and a branched carboranes.

5. The rotaxane of claim 1, wherein said linking moiety is selected from the group consisting of alkyl, alkenyl, alkynyl, cycloalkyl, heteroalicyclic, aryl, heteroaryl, ether, thioether, amide, ester, carbamate, thioamide, thiocarbamate, imine, aza, organophosphorous, organoboron and organosilicon.

6. The rotaxane of claim 1, wherein said effector moiety is selected from the group consisting of a charged moiety, a metal ion complex moiety, a magnetic moiety and a light absorbing moiety.

7. The rotaxane of claim 1, wherein said cucurbit[n]uril further comprises at least one functionality attached thereto selected from the group consisting of an anchoring group, an effector moiety, a detectible moiety and a biomolecule.

* * * * *